(12) United States Patent
Beaulieu et al.

(10) Patent No.: US 6,841,566 B2
(45) Date of Patent: Jan. 11, 2005

(54) VIRAL POLYMERASE INHIBITORS

(75) Inventors: Pierre Louis Beaulieu, Laval (CA); Gulrez Fazal, Laval (CA); Sylvie Goulet, Laval (CA); George Kukolj, Laval (CA); Martin Poirier, Laval (CA); Youla S. Tsantrizos, Laval (CA)

(73) Assignee: Boehringer Ingelheim, Ltd., Laval (CA)

( * ) Notice: Subject to any disclaimer, the term of this patent is extended or adjusted under 35 U.S.C. 154(b) by 38 days.

(21) Appl. No.: 10/198,259

(22) Filed: Jul. 18, 2002

(65) Prior Publication Data

US 2003/0236251 A1 Dec. 25, 2003

Related U.S. Application Data

(60) Provisional application No. 60/306,669, filed on Jul. 20, 2001, and provisional application No. 60/338,324, filed on Dec. 7, 2001.

(51) Int. Cl.[7] .................. A61K 31/4184; C07D 405/04
(52) U.S. Cl. .................. 514/394; 548/304.7; 548/305.1; 548/306.1; 548/181; 546/199; 546/273.4; 544/139; 544/333; 514/338; 514/370
(58) Field of Search .................. 514/394, 338, 514/370; 548/304.7, 305.1, 306.1, 181, 304.4; 546/199, 273.4; 544/139, 333

(56) References Cited

U.S. PATENT DOCUMENTS 6,448,281 B1    9/2002    Beaulieu et al.

FOREIGN PATENT DOCUMENTS

| EP | 1 162 196 A1 | 12/2001 |
|---|---|---|
| WO | WO 00/06529 A1 | 2/2000 |
| WO | WO 00/10573 A1 | 3/2000 |
| WO | WO 00/13708 A1 | 3/2000 |
| WO | WO 00/18231 A1 | 4/2000 |
| WO | WO 01/47883 A1 | 7/2001 |

OTHER PUBLICATIONS

Beaulieu, P. L. et al; "Viral Polymerase Inhibitors"; USSN 10/198,384; filed Jul. 18, 2002; attorney docket No. 13/090.
Beaulieu, P. L. et al; "Viral Polyerase Inhibitors"; USSN 10/198,680; filed Jul. 18, 2002; attorney docket No. 13/095.

Hashimoto, et al; "Fused–Ring Compounds And Use Thereof As Drugs"; Pub. No. US 2003/0050320 A1; Mar. 13, 2003.

Primary Examiner—Charanjit S. Aulakh
(74) Attorney, Agent, or Firm—Robert P. Raymond; Michael Morris; Philip I. Datlow

(57) ABSTRACT

An isomer, enantiomer, diastereoisomer, or tautomer of a compound, represented by formula I:

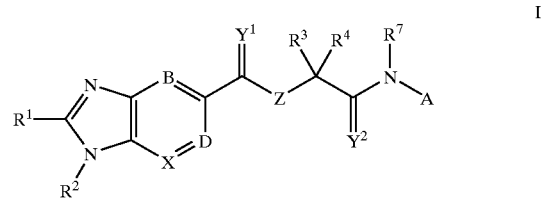

wherein $R^1$ is selected from: H, haloalkyl, $(C_{1-6})$alkyl, $(C_{2-6})$alkenyl, $(C_{3-7})$cycloalkyl, $(C_{2-6})$alkynyl, $(C_{5-7})$ cycloalkenyl, 6 or 10-membered aryl, Het all optionally substituted;
$R^2$ is selected from $(C_{1-6})$alkyl, $(C_{3-7})$cycloalkyl, $(C_{6-10})$ bicycloalkyl, 6- or 10-membered aryl, or Het all optionally substituted;
B is N or $CR^5$, wherein $R^5$ is H, halogen, haloalkyl, $(C_{1-6})$alkyl, $(C_{3-7})$cycloalkyl or $(C_{1-6})$alkyl-$(C_{3-7})$ cycloalkyl; X is N or $CR^5$; D is N or $CR^5$; each of $Y_1$ and $Y_2$ is independently O or S; Z is O, N, or $NR^Z$ wherein $R^Z$ is H, $(C_{1-6})$alkyl, $(C_{3-7})$cycloalkyl or $(C_{1-6})$ alkyl-$(C_{3-7})$cycloalkyl; $R^3$ and $R^4$ are each independently H, $(C_{1-6})$alkyl, first $(C_{3-7})$cycloalkyl or 6- or 10-membered aryl, Het $(C_{1-6})$alkyl-6- or 10-membered aryl, $(C_{1-6})$alkyl-Het; or each $R^3$ and $R^4$ are independently covalently bonded together to form second $(C_{3-7})$cycloalkyl, or heterocycle, all optionally substituted; or when Z is N, either $R^3$ or $R^4$ are independently covalently bonded thereto to form a nitrogen-containing heterocycle; $R^7$ is H, $(C_{1-6}$alkyl), $(C_{3-7})$ cycloalkyl or $(C_{1-6})$alkyl-$(C_{3-7})$cycloalkyl; or $R^7$ is covalently bonded to either of $R^3$ or $R^4$ to form a heterocycle; A is $(C_{1-6})$alkyl-$CONHR^8$ wherein $R^8$ is -6- or 10-membered aryl, or Het; or A is a 6- or 10-membered aryl, or Het said aryl or Het being optionally substituted; or a salt or a derivative thereof; such compounds being potent inhibitors of HCV NS5B polymerase.

62 Claims, No Drawings

VIRAL POLYMERASE INHIBITORS

RELATED APPLICATIONS

Benefit of U.S. Provisional application Serial No. U.S. 60/306,669 filed on Jul. 20, 2001, and U.S. Provisional application Serial No. U.S. 60/338,324 filed on Dec. 7, 2001 is hereby claimed. These Provisional Applications are herein incorporated by reference in their entirety.

TECHNICAL FIELD OF THE INVENTION

The invention relates to inhibitors of RNA dependent RNA polymerases, particularly those viral polymerases within the Flaviviridae family, more particularly HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046-2051*). HCV is not easily cleared by the hosts' immunological defences; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S–20S*). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection. Prolonged treatment of chronically infected patients with interferon or interferon and ribavirin is the only currently approved therapy, but it achieves a sustained response in fewer than 50% of cases (Lindsay, K. L.; 1997; *Hepatology* 26: 71S–77S*, and Reichard, O.; Schvarcz, R.; Weiland, O.; 1997 *Hepatology* 26: 108S–111S*).
* incorporated herein by reference HCV belongs to the family *Flaviviridae*, genus *hepacivirus*, which comprises three genera of small enveloped positive-strand RNA viruses (Rice, C. M.; 1996; *"Flaviviridae*: the viruses and their replication"; pp. 931–960 in Fields Virology; Fields, B. N.; Knipe, D. M.; Howley, P. M. (eds.); Lippincott-Raven Publishers, Philadelphia Pa.*). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274–288*). The HCV polyprotein is cleaved co- and post-translationally into at least 10 individual polypeptides (Reed, K. E.; Rice, C. M.; 1999; *Curr. Top. Microlbiol. Immunol.* 242: 55–84*). The structural proteins result from signal peptidase induced cleavage in the N-terminal portion of the polyprotein. Two viral proteases mediate downstream cleavages to produce non-structural (NS) proteins that function as components of the HCV RNA replicase. The NS2–3 protease spans the C-terminal half of the NS2 and the N-terminal one-third of NS3 and catalyses cis cleavage of the NS2/3 site. The same portion of NS3 also encodes the catalytic domain of the NS3–4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12–22*; and Lohmann, V.; Körner, F.; Herian, U.; Bartenschlager, R.; 1997; *J. Virol.* 71: 8416–8428*). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046–2051*).
* incorporated herein by reference The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics.

WO 00/06529 reports inhibitors of NS5B which are α, γ-diketoacids.

WO 00/13708, WO 00/10573, WO 00/18231, and WO 01/47883 report inhibitors of NS5B proposed for treatment of HCV.

SUMMARY OF THE INVENTION

It is therefore an object of the invention to provide a novel series of compounds having improved inhibitory activity against HCV polymerase.

In a first aspect of the invention, there is provided an isomer, enantiomer, diastereoisomer, or tautomer of a compound, represented by formula I:

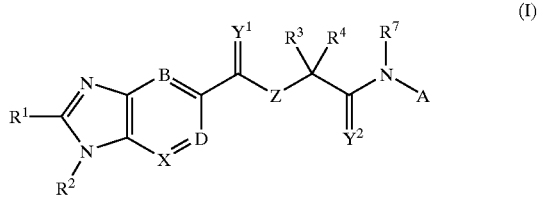

(I)

wherein
R$^1$ is selected from: R$^{11}$, OR$^{11}$, SR$^{11}$, COOR$^{11}$, SO$_2$N(R$^{12}$)$_2$, N(R$^{12}$)$_2$, CON(R$^{12}$)$_2$, NR$^{12}$C(O)R$^{12}$ or NR$^{12}$C(O)NR$^{12}$ wherein R$^{11}$ and each R$^{12}$ is independently H, (C$_{1-6}$)alkyl, haloalkyl, (C$_{2-6}$)alkenyl, (C$_{3-7}$)cycloalkyl, (C$_{2-6}$)alkynyl, (C$_{5-7}$)cycloalkenyl, 6 or 10-membered aryl or Het, said R$^{11}$ and R$^{12}$ being optionally substituted with R$^{10}$; or both R$^{12}$ are bonded together to form a 5, 6 or 7-membered saturated heterocycle with the nitrogen to which they are attached;

R$^2$ is selected from (C$_{1-6}$)alkyl, haloalkyl, (C$_{3-7}$)cycloalkyl, (C$_{5-7}$)cycloalkenyl, (C$_{6-10}$)bicycloalkyl, (C$_{6-10}$)bicycloalkenyl, 6- or 10-membered aryl, Het, (C$_{1-6}$)alkyl-aryl or (C$_{1-6}$)alkyl-Het, said alkyl, cycloalkyl, cycloalkenyl, bicycloalkyl, bicycloalkenyl, aryl, Het, alkyl-aryl and alkyl-Het being optionally substituted with from 1 to 4 substituents selected from: halogen, or
  a) (C$_{1-6}$)alkyl optionally substituted with:
    OR$^{21}$ or SR$^{21}$ wherein R$^{21}$ is H, (C$_{1-6}$alkyl), (C$_{3-7}$)cycloalkyl, (C$_{1-6}$)alkyl-(C$_{3-7}$)cycloalkyl, aryl, Het, (C$_{1-6}$)alkyl-aryl or (C$_{1-6}$)alkyl-Het; or
    N(R$^{22}$)$_2$ wherein each R$^{22}$ is independently H, (C$_{1-6}$)alkyl, (C$_{3-7}$)cycloalkyl, (C$_{1-6}$)alkyl- ($C_{3-7}$)cycloalkyl, aryl, Het, ($C_{1-6}$)alkyl-aryl or ($C_{1-6}$)alkyl-Het; or both $R^{22}$ are covalently bonded together and to the nitrogen to which they are attached to form a 5, 6 or 7-membered saturated heterocycle;

b) $OR^{23}$ wherein $R^{23}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$)alkyl-aryl or ($C_{1-6}$)alkyl-Het;

c) $SR^{24}$ wherein $R^{24}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$)alkyl-aryl or ($C_{1-6}$)alkyl-Het; and d) $N(R^{25})_2$ wherein each $R^{25}$ is independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or both $R^{25}$ are covalently bonded together and to the nitrogen to which they are attached to form a 5, 6 or 7-membered saturated heterocycle;

B is N or $CR^5$, wherein $R^5$ is H, halogen, ($C_{1-6}$)alkyl, haloalkyl, ($C_{3-7}$)cycloalkyl or ($C_{1-6}$)alkyl-($C_{3-7}$)cycloalkyl; or $R^5$ is $OR^{51}$ or $SR^{51}$, $COR^{51}$ or $NR^{51}COR^{51}$ wherein each $R^{51}$ is independently H, ($C_{1-6}$)alkyl), ($C_{3-7}$)cycloalkyl or ($C_{1-6}$)alkyl-($C_{3-7}$)cycloalkyl; or $R^5$ is $NR^{52}R^{53}$ wherein $R^{52}$ and $R^{53}$ are each independently H, ($C_{1-6}$)alkyl, ($C_{3-7}$)cycloalkyl, ($C_{1-6}$)alkyl-($C_{3-7}$)cycloalkyl, or both $R^{52}$ and $R^{53}$ are covalently bonded together and to the nitrogen to which they are attached to form a 5, 6 or 7-membered saturated heterocycle;

X is N or $CR^5$, wherein $R^5$ is as defined above;

D is N or $CR^5$, wherein $R^5$ is as defined above;

each of $Y_1$ and $Y_2$ is independently O or S;

Z is O, N, or $NR^6$ wherein $R^6$ is H, ($C_{1-6}$)alkyl, ($C_{3-7}$)cycloalkyl or ($C_{1-6}$)alkyl-($C_{3-7}$)cycloalkyl;

$R^3$ and $R^4$ are each independently H, ($C_{1-6}$)alkyl, haloalkyl, ($C_{3-7}$)cycloalkyl, 6- or 10-membered aryl, Het, ($C_{1-6}$)alkyl-aryl, ($C_{1-6}$)alkyl-Het, wherein said alkyl, cycloalkyl, aryl, Het, ($C_{1-6}$)alkyl-aryl, ($C_{1-6}$)alkyl-Het are optionally substituted with $R^{30}$; or $R^7$ and $R^8$ are covalently bonded together to form second ($C_{3-7}$)cycloalkyl or a 4, 5- or 6-membered heterocycle having from 1 to 3 heteroatom selected from O, N, and S; or when Z is $NR^6$, either of $R^7$ or $R^8$ is covalently bonded to $R^6$ to form a nitrogen-containing 5- or 6-membered heterocycle;

$R^7$ is H, ($C_{1-6}$alkyl), ($C_{3-7}$)cycloalkyl or ($C_{1-6}$)alkyl-($C_{3-7}$)cycloalkyl, aryl, Het, ($C_{1-6}$)alkyl-aryl or ($C_{1-6}$)alkyl-Het, all of which optionally substituted with $R^{70}$; or $R^7$ is covalently bonded to either of $R^3$ or $R^4$ to form a 5- or 6-membered heterocycle;

A is a 6- or 10-membered aryl, Het, ($C_{1-6}$)alkyl-aryl, ($C_{1-6}$)alkyl-Het, ($C_{1-6}$)alkyl-CONH-aryl or ($C_{1-6}$)alkyl-CONH-Het, all of which being optionally substituted with:

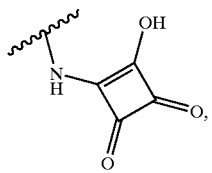

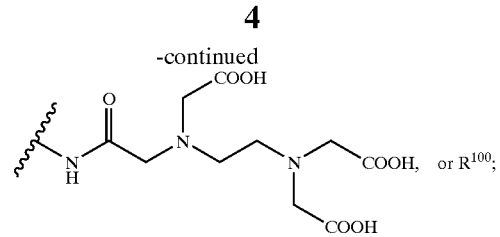

or a salt or a derivative thereof;

wherein Het is defined as:

5- or 6-membered heterocycle having 1 to 4 heteroatoms selected from O, N, and S, or a 9- or 10-membered heterobicycle having 1 to 5 heteroatoms selected from O, N and S; and $R^{10}$, $R^{30}$, $R^{70}$ and $R^{100}$ are defined as:

1 to 4 substituents selected from: halogen, $OPO_3H$, $NO_2$, cyano, azido, $C(=NH)NH_2$, $C(=NH)NH(C_{1-6})$alkyl or $C(=NH)NHCO(C_{1-6})$alkyl; or 1 to 4 substituents selected from:

a) ($C_{1-6}$)alkyl or haloalkyl, ($C_{3-7}$)cycloalkyl, $C_{3-7}$ spirocycloalkyl optionally containing 1 or 2 heteroatom, ($C_{2-6}$)alkenyl, ($C_{2-8}$)alkynyl, ($C_{1-6}$)alkyl-($C_{3-7}$)cycloalkyl, all of which optionally substituted with $R^{150}$;

b) $OR^{104}$ wherein $R^{104}$ is H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{150}$;

c) $OCOR^{105}$ wherein $R^{105}$ is ($C_{1-6}$)alkyl, ($C_{3-7}$)cycloalkyl, ($C_{1-6}$)alkyl-($C_{3-7}$)cycloalkyl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{150}$;

d) $SR^{108}$, $SO_2N(R^{108})_2$ or $SO_2N(R^{108})C(O)R^{108}$ wherein each $R^{108}$ is independently H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het or heterocycle being optionally substituted with $R^{150}$;

e) $NR^{111}R^{112}$ wherein $R^{111}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, and $R^{112}$ is H, CN, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl, ($C_{1-6}$alkyl)Het, $COOR^{115}$ or $SO_2R^{115}$ wherein $R^{115}$ is ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het, or heterocycle being optionally substituted with $R^{150}$;

f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het being optionally substituted with $R^{150}$;

g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$)alkyl- ($C_{3-7}$)cycloalkyl, aryl, Het, ($C_{1-6}$alkyl)aryl or ($C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, ($C_{1-6}$)alkyl-($C_{3-7}$)cycloalkyl, aryl, Het, ($C_{1-6}$alkyl)aryl or ($C_{1-6}$alkyl)Het or heterocycle being optionally substituted with $R^{150}$;

h) $NR^{121}COCOR^{122}$ wherein $R^{121}$ and $R^{122}$ is each H, ($C_{1-6}$)alkyl, ($C_{3-7}$)cycloalkyl, ($C_{1-6}$)alkyl-($C_{3-7}$)cycloalkyl, a 6- or 10-membered aryl, Het, ($C_{1-6}$alkyl)aryl or ($C_{1-6}$alkyl)Het, said alkyl, cycloalkyl, alkyl-cycloalkyl, aryl, Het, ($C_{1-6}$alkyl)aryl or ($C_{1-6}$alkyl)Het being optionally substituted with $R^{150}$; or $R^{122}$ is $OR^{123}$ or $N(R^{124})_2$ wherein $R^{123}$ and each $R^{124}$ is independently H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or $R^{124}$ is OH or O($C_{1-6}$alkyl) or both $R^{124}$ are covalently bonded together to form a 5, 6 or 7-membered saturated heterocycle, said alkyl, cycloalkyl, alkyl-cycloalkyl, aryl, Het, ($C_{1-6}$alkyl)aryl or ($C_{1-6}$alkyl)Het and heterocycle being optionally substituted with $R^{150}$;

i) $COR^{127}$ wherein $R^{127}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{150}$;

j) $COOR^{128}$ wherein $R^{128}$ is H, ($C_{1-6}$)alkyl, ($C_{3-7}$)cycloalkyl, or($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, or($C_{1-6}$)alkyl-($C_{3-7}$)cycloalkyl, aryl, Het, ($C_{1-6}$alkyl)aryl and ($C_{1-6}$alkyl)Het being optionally substituted with $R^{150}$;

k) $CONR^{129}R^{130}$ wherein $R^{129}$ and $R^{130}$ are independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$alkyl)aryl, ($C_{1-6}$alkyl)Het and heterocycle being optionally substituted with $R^{150}$;

l) aryl, Het, ($C_{1-6}$alkyl)aryl or ($C_{1-6}$alkyl)Het, all of which being optionally substituted with $R^{150}$; and wherein $R^{150}$ is defined as:

1 to 3 substituents selected from: halogen, $OPO_3H$, $NO_2$, cyano, azido, C(=NH)$NH_2$, C(=NH)NH($C_{1-6}$)alkyl or C(=NH)NHCO($C_{1-6}$)alkyl;

or 1 to 3 substituents selected from:

a) ($C_{1-6}$)alkyl or haloalkyl, ($C_{3-7}$)cycloalkyl, $C_{3-7}$ spirocycloalkyl optionally containing 1 or 2 heteroatom, ($C_{2-6}$)alkenyl, ($C_{2-8}$)alkynyl, ($C_{1-6}$)alkyl-($C_{3-7}$)cycloalkyl, all of which optionally substituted with $R^{160}$;

b) $OR^{104}$ wherein $R^{104}$ is H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{160}$;

c) $OCOR^{105}$ wherein $R^{105}$ is ($C_{1-6}$alkyl), ($C_{3-7}$)cycloalkyl, ($C_{1-6}$)alkyl-($C_{3-7}$)cycloalkyl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{160}$;

d) $SR^{108}$, $SO_3H$, $SO_2N(R^{108})_2$ or $SO_2N(R^{108})C(O)R^{108}$ wherein each $R^{108}$ is independently H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het or heterocycle being optionally substituted with $R^{160}$;

e) $NR^{111}R^{112}$ wherein $R^{111}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, and $R^{112}$ is H, CN, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl, ($C_{1-6}$alkyl)Het, $COOR^{115}$ or $SO_2R^{115}$ wherein $R^{115}$ is ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het, or heterocycle being optionally substituted with $R^{160}$;

f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het being optionally substituted with $R^{160}$;

g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or $R^{118}$ is covalently bonded to $R^{119}$ and to the nitrogen to which they are attached to form a 5, 6 or 7-membered saturated heterocycle, or $R^{119}$ and $R^{120}$ are covalently bonded together and to the nitrogen to which they are attached to form a 5, 6 or 7-membered saturated heterocycle, said alkyl, cycloalkyl, ($C_{1-6}$)alkyl-($C_{3-7}$)cycloalkyl, aryl, Het, ($C_{1-6}$alkyl)aryl or ($C_{1-6}$alkyl)Het or heterocycle being optionally substituted with $R^{160}$;

h) $NR^{121}COCOR^{122}$ wherein $R^{121}$ and $R^{122}$ is each H, ($C_{1-6}$)alkyl, ($C_{3-7}$)cycloalkyl, ($C_{1-6}$)alkyl-($C_{3-7}$)cycloalkyl, a 6- or 10-membered aryl, Het, ($C_{1-6}$alkyl)aryl or ($C_{1-6}$alkyl)Het, said alkyl, cycloalkyl, alkyl-cycloalkyl, aryl, Het, ($C_{1-6}$alkyl)aryl or ($C_{1-6}$alkyl)Het being optionally substituted with $R^{160}$, or $R^{122}$ is $OR^{123}$ or $N(R^{124})_2$ wherein $R^{123}$ and each $R^{124}$ is independently H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or $R^{124}$ is OH or O($C_{1-6}$alkyl) or both $R^{124}$ are covalently bonded together to form a 5, 6 or 7-membered saturated heterocycle, said alkyl, cycloalkyl, alkyl-cycloalkyl, aryl, Het, ($C_{1-6}$alkyl)aryl or ($C_{1-6}$alkyl)Het and heterocycle being optionally substituted with $R^{160}$;

i) $COR^{127}$ wherein $R^{127}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{160}$;

j) tetrazole, $COOR^{128}$ wherein $R^{128}$ is H, ($C_{1-6}$)alkyl, ($C_{3-7}$)cycloalkyl, or($C_{1-6}$)alkyl-($C_{3-7}$)cycloalkyl, aryl, Het, (C$_{1-6}$alkyl)aryl or (C$_{1-6}$alkyl)Het, said (C$_{1-6}$)alkyl, (C$_{3-7}$)cycloalkyl, or(C$_{1-6}$)alkyl-(C$_{3-7}$)cycloalkyl, aryl, Het, (C$_{1-6}$alkyl)aryl and (C$_{1-6}$alkyl)Het being optionally substituted with R$^{160}$; and k) CONR$^{129}$R$^{130}$ wherein R$^{129}$ and R$^{130}$ are independently H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or both R$^{129}$ and R$^{130}$ are covalently bonded together and to the nitrogen to which they are attached to form a 5, 6 or 7-membered saturated heterocycle, said alkyl, cycloalkyl, alkyl-cycloalkyl, aryl, Het, (C$_{1-6}$alkyl)aryl, (C$_{1-6}$alkyl)Het and heterocycle being optionally substituted with R$^{160}$;

wherein R$^{160}$ is defined as 1 or 2 substituents selected from:

tetrazole, halogen, CN, C$_{1-6}$alkyl, haloalkyl, COOR$^{161}$, SO$_3$H, SR$^{161}$, SO$_2$R$^{161}$, OR$^{161}$, N(R$^{162}$)$_2$, SO$_2$N(R$^{162}$)$_2$, NR$^{162}$COR$^{162}$ or CON(R$^{162}$)$_2$, wherein R$^{161}$ and each R$^{162}$ is independently H, (C$_{1-6}$)alkyl, (C$_{3-7}$)cycloalkyl or (C$_{1-6}$)alkyl-(C$_{3-7}$)cycloalkyl; or both R$^{162}$ are covalently bonded together and to the nitrogen to which they are attached to form a 5, 6 or 7-membered saturated heterocycle, Alternatively, there is provided a compound of formula Ia:

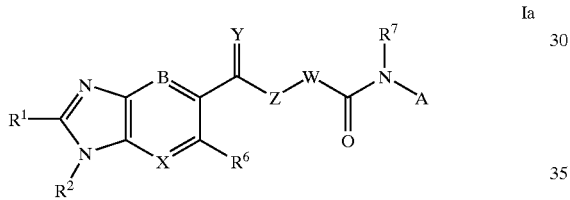

Ia wherein R$^1$ is selected from: 5- or 6-membered heterocycle having 1 to 4 heteroatoms selected from O, N, and S and phenyl, said heterocycle and phenyl being optionally substituted with from 1 to 4 (C$_{1-4}$)alkyl substituents;

R$^2$ is selected from: (C$_{3-7}$)cycloalkyl, (C$_{3-7}$)cycloalkyl(C$_{1-3}$)alkyl, and norbornane;

X is CH or N;

R$^6$ is H or (C$_{1-6}$alkyl);

Y is O or S;

B is N or CR$^5$, wherein R$^5$ is H or (C$_{1-6}$)alkyl with the proviso that X and B are not both N;

Z is O, N, or NH;

W is CR$^3$R$^4$ wherein R$^3$ and R$^4$ are each independently H, (C$_{1-6}$alkyl), (C$_{3-7}$cycloalkyl), (C$_{1-6}$alkyl)phenyl, (C$_{1-6}$alkyl)-(C$_{3-7}$cycloalkyl), (C$_{3-7}$cycloalkyl)-(C$_{1-6}$alkyl) (C$_{3-7}$cycloalkyl)-(C$_{2-4}$alkenyl), (C$_{1-6}$alkyl)-OH, phenyl, CH$_2$biphenyl, 5- or 6-membered heterocycle having from 1 to 4 heteroatoms selected from O, N, and S, 9- or 10-membered heterobicycle having 1 to 4 heteroatoms selected from O, N, and S, (C$_{1-6}$alkyl)-5- or 6-membered heterocycle having from 1 to 4 heteroatoms selected from O, N, and S, or (C$_{1-6}$alkyl)-9- or 10-membered heterobicycle having 1 to 4 heteroatoms selected from O, N, and S, or R$^3$ and R$^4$ are covalently bonded together to form (C$_{3-7}$cycloalkyl), 4-, 5- or 6-membered heterocycle having from1 to 4 heteroatoms selected from O, N, and S; or when Z is N, either R$^3$ or R$^4$ is covalently bonded thereto to form a 5-membered heterocycle;

wherein said alkyl, cycloalkyl, heterocycle, heterobicycle, phenyl are optionally substituted with from 1 to 4 substituents selected from: OH, COOH, (C$_{1-6}$alkyl), (C$_{2-4}$alkenyl), CONH$_2$, NH$_2$, NH(C$_{1-6}$alkyl), N(C$_{1-6}$alkyl)$_2$, NHCOCOOH, NHCOCON(C$_{1-6}$alkyl)$_2$, NHCOCONH(C$_{1-6}$alkyl), SH, S(C$_{1-6}$alkyl), NHC(=NH)NH$_2$, and COO(C$_{1-6}$alkyl);

R$^7$ is H or (C$_{1-6}$alkyl);

A is selected from: (C$_{1-3}$alkyl)CONHaryl, 6- or 10-membered aryl, biphenyl, 5- or 6-atom heterocycle having 1 to 4 heteroatoms selected from O, N and S, 9- or 10-membered heterobicycle having 1 to 4 heteroatoms selected from O, N and S;

wherein said aryl, biphenyl, first heterocycle, and heterobicycle are all optionally substituted with from 1 to 4 substituents selected from: OH, COOH, COO(C$_{1-6}$)alkyl, (C$_{1-6}$)alkyl, (C$_{1-6}$)alkylCOOH, (C$_{1-6}$alkyl)(C$_{2-4}$alkynyl), (C$_{1-6}$)alkyl-hydroxy, phenyl, benzyloxy, halogen, (C$_{2-4}$)alkenyl, (C$_{2-4}$)alkenyl-(C$_{1-6}$)alkyl-COOH, 5- or 6-membered second heterocycle having 1 to 4 heteroatoms selected from O, N and S, NH-5- or 6-membered heterocycle having 1 to 4 heteroatoms selected from O, N, and S, wherein said second heterocycle and phenyl being optionally substituted with from 1 to 4 substituents selected from: (C$_{1-6}$alkyl), CF$_3$, OH, (C$_{1-6}$alkyl) COOH, O(C$_{1-6}$alkyl)COOH, (C$_{1-6}$alkyl)COO(C$_{1-6}$alkyl), CH$_2$phenyl, COO(C$_{1-6}$alkyl), (C$_{1-6}$alkyl)O(C$_{1-6}$alkyl), COOH, NCH(C$_{1-6}$alkyl)$_2$, NCO(C$_{1-6}$alkyl), NH$_2$, NH(C$_{1-6}$alkyl), and N(C$_{1-6}$alkyl)$_2$;

halogen, OPO$_3$H, benzyl, sulfonamido, SH, SOCH$_3$, SO$_3$H, SO$_2$CH$_3$, S(C$_{1-6}$alkyl)COOH, —CONH$_2$, —COCH$_3$, (C$_{1-3}$)alkyl, (C$_{2-4}$alkenyl)COOH wherein said alkenyl is optionally substituted with from 1 to 2 (C$_{1-6}$alkyl) substituents, (C$_{2-4}$alkenyl)COO(C$_{1-6}$alkyl), tetrazolyl, COOH, triazolyl, OH, NO$_2$, NH$_2$, —O(CH$_2$)$_p$COOH, hydantoin, benzoyleneurea, (C$_{1-4}$)alkoxy, (C$_{1-4}$)alkoxy(C$_{1-6}$alkyl)COOH, cyano, azido, —O—(C$_{1-6}$)alkyl COOH, —O—(C$_{1-6}$)alkyl COO—(C$_{1-6}$)alkyl, —NHCOCOOH, —NHCOCONHOH, —NHCOCONH$_2$, —NHCOCONHCH$_3$, —NHCO(C$_{1-6}$)alkyl-COOH, —NHCOCONH(C$_{1-6}$)alkyl-COOH, —NHCO(C$_{3-7}$)cycloalkyl-COOH, —NHCONH(C$_{6-10}$)aryl-COOH, —NHCONH(C$_{6-10}$)aryl-COO(C$_{1-6}$)alkyl, —NHCONH(C$_{1-6}$)alkyl-COOH, —NHCONH(C$_{1-6}$)alkyl-COO(C$_{1-6}$)alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$)alkyl COOH, —NH(C$_{1-6}$)alkyl-(C$_{6-10}$)aryl-COOH, —NHCH$_2$COOH, —NHCONH$_2$, —NHCO(C$_{1-6}$)hydroxyalkyl COOH, —OCO(C$_{1-6}$)hydroxyalkyl COOH, (C$_{3-6}$)cycloalkyl COOH,

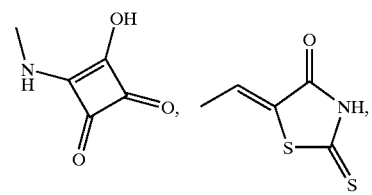

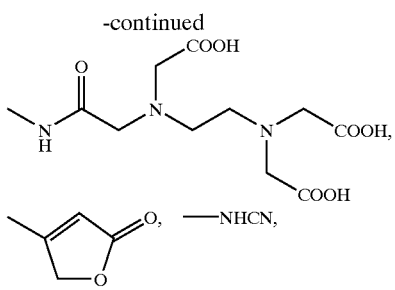

—NHCHO, —NHSO$_2$CH$_3$, —NHSO$_2$CF$_3$, coumarin, (C$_{1-6}$)alkyl-amino, di-(C$_{1-6}$)alkyl-amino, C(halogen)$_3$, —NH(C$_{2-4}$)acyl, —NH(C$_{6-10}$)aroyl, —CONH(C$_{1-6}$alkyl), —CO(C$_{1-6}$)alkyl-COOH, —CONH(C$_{1-6}$)alkyl-COOH, —CO—NH-alanyl, —CONH(C$_{2-4}$)alkylN(C$_{1-6}$alkyl)$_2$, —CONH(C$_{2-4}$)alkyl-Het —CONH(C$_{2-4}$)alkyl-(COOH)-Het-CONH(C$_{1-2}$alkyl)(OH)(C$_{1-2}$alkyl) OH, —CONH(C$_{1-6}$) alkyl-COOH, —CONH(C$_{6-10}$ aryl), —CONH-Het —CONH(C$_{6-10}$)aryl-COOH, —CONH(C$_{6-10}$)aryl-COO (C$_{1-6}$)alkyl, —CONH(C$_{1-6}$)alkyl-COO(C$_{1-6}$)alkyl, —CONH(C$_{6-10}$)aryl-(C$_{1-6}$)alkyl-COOH, —CONH(C$_{6-10}$) aryl-(C$_{2-6}$)alkenyl-COOH, or salt thereof.

In a second aspect of the invention, there is provided a compound of the Formula I, or a pharmaceutically acceptable salt thereof, as an inhibitor of RNA dependent RNA polymerase activity of the enzyme NS5B, encoded by HCV.

In a third aspect of the invention, there is provided a compound of the formula I, or a pharmaceutically acceptable salt thereof, as an inhibitor of HCV replication.

In a fourth aspect of the invention, there is provided a method of treating or preventing HCV infection in a mammal, comprising administering to the mammal an effective amount of a compound of formula I, or a pharmaceutically acceptable salt thereof.

In a fifth aspect of the invention, there is provided a pharmaceutical composition for the treatment or prevention of HCV infection, comprising an effective amount of a compound of formula I, or a pharmaceutically acceptable salt thereof, and a pharmaceutically acceptable carrier.

In a sixth aspect of the invention, there is provided a method of treating or preventing HCV infection in a mammal, comprising administering to the mammal an effective amount of a compound of formula I, or a pharmaceutically acceptable salt thereof in combination with another anti-HCV agent.

In a seventh aspect of the invention, there is provided a use of a compound of formula I, for the manufacture of a medicament for the treatment of HCV infection.

In a eighth aspect of the invention, there is provided a use of a compound of formula I, to prevent HCV infection.

In an ninth aspect of the invention, there is provided a use of a compound of formula I, as an HCV polymerase inhibitor.

In an tenth aspect of the invention, there is provided an intermediate compound of formula (i):

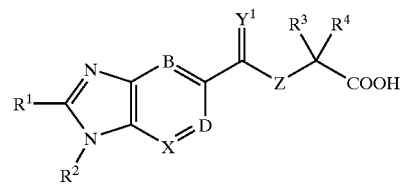

wherein $R^1$, $R^2$, $R^3$, $R^4$, B, D, X, $Y^1$, and Z are as defined herein, or a derivative thereof.

In a eleventh aspect of the invention, there is provided an intermediate compound of formula I(ii):

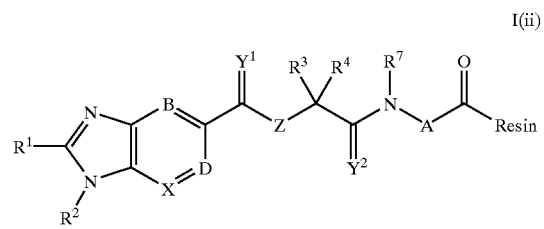

wherein $R^1$, $R^2$, $R^3$, $R^4$, $R^7$, A, B, D, X, $Y^1$, $Y^2$ and Z are as defined herein, or a derivative thereof.

In a twelfth aspect of the invention, there is provided a process for producing compounds of formula I,

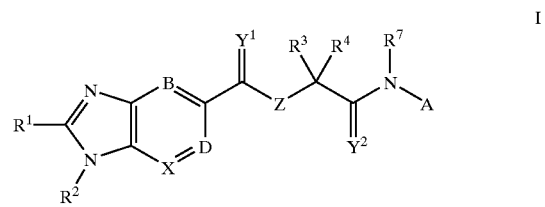

wherein $R^1$, $R^2$, $R^3$, $R^4$, $R^7$, A, B, D, X, $Y^1$, $Y^2$ and Z are as defined herein, comprising:

a) removing, in a mixture of an aqueous base or an aqueous acid in a co-solvent, the protecting group (PG) from:

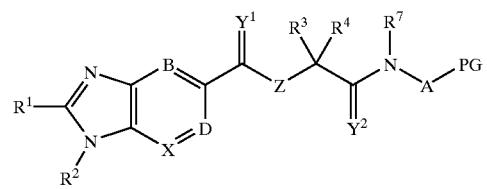

wherein $R^1$, $R^2$, $R^3$, $R^4$, $R^7$, A, B, D, X, $Y^1$, $Y^2$ and Z are as defined herein, and wherein PG is a carboxylic acid protecting group, so as to produce compounds of formula I.

In a thirteenth aspect of the invention, there is provided a process for producing compounds of formula I,

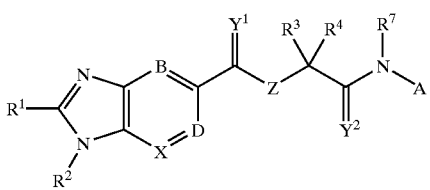

wherein $R^1, R^2, R^3, R^4, R^7, A, B, D, X, Y^1, Y^2$ and $Z$ are as defined herein, comprising:

a) cleaving, under acidic conditions, intermediate compound I(ii)

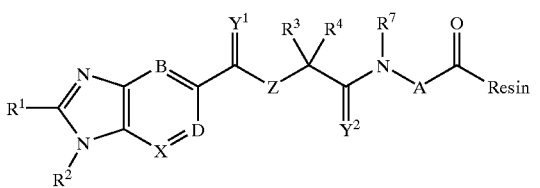

so as to produce compounds of formula I, where $R^1, R^2, R^3, R^4, R^7, A, B, D, X, Y^1$ and $Y^2$ are as defined herein.

In a fourteenth aspect of the invention, there is provided a process for producing compounds of formula I,

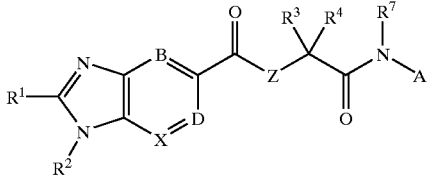

wherein $R^1, R^2, R^3, R^4, R^7, A, B, D, X$ and $Z$ are as defined herein, comprising:

i) coupling intermediate compound of formula (i):

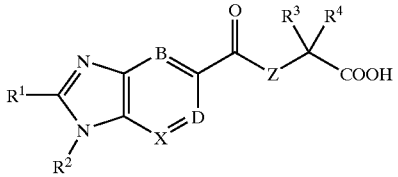

wherein $R^1, R^2, R^3, R^4, B, D, X,$ and $Z$ are as defined herein, or a derivative thereof, with $HN(R^7)$-A wherein $R^7$ and A are as defined herein, to produce compound of formula I.

DETAILED DESCRIPTION OF THE INVENTION

Definitions

The following definitions apply unless otherwise noted:

As used herein, the terms "$(C_{1-3})$alkyl", "$(C_{1-4})$alkyl" or "$(C_{1-6})$alkyl", either alone or in combination with another radical, are intended to mean acyclic straight or branched chain alkyl radicals containing up to three, four and six carbon atoms respectively. Examples of such radicals include methyl, ethyl, propyl, butyl, hexyl, 1-methylethyl, 1-methylpropyl, 2-methylpropyl, 1,1-dimethylethyl.

As used herein, the term "$(C_{2-6})$alkenyl", either alone or in combination with another radical, is intended to mean an unsaturated, acyclic straight chain radical containing two to six carbon atoms.

As used herein, the term "$(C_{2-6})$alkynyl" either alone or in combination with another group, is intended to mean an unsaturated, acyclic straight chain sp hybridized radical containing 2 to six carbon atoms.

As used herein, the term "$(C_{3-7})$cycloalkyl", either alone or in combination with another radical, means a cycloalkyl radical containing from three to seven carbon atoms and includes cyclopropyl, cyclobutyl, cyclopentyl, cyclohexyl and cycloheptyl.

As used herein, the term "$(C_{5-7})$cycloalkenyl", either alone or in combination with another radical, means an unsaturated cyclic radical containing five to seven carbon atoms.

As used herein, the term "carboxy protecting group" defines protecting groups that can be used during coupling and are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

As used herein, the term "aryl", or "6- or 10-membered aryl" either alone or in combination with another radical means aromatic radical containing six or ten carbon atoms, for example phenyl or naphthyl.

As used herein the term heteroatom means O, S or N.

As used herein, the term "heterocycle", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "heterobicyclic" as used herein, means a heterocycle as defined above fused to one or more other cycle, be it a heterocycle or any other cycle. Examples of such heterocycles include, but are not limited to, pyrrolidine, tetrahydrofuran, thiazolidine, pyrrole, thiophene, coumarin, hydantoin, diazepine, 1H-imidazole, isoxazole, thiazole, tetrazole, piperidine, 1,4-dioxane, 4-morpholine, pyridine, pyridine-N-oxide, pyrimidine, thiazolo[4,5-b]-pyridine, quinoline, or indole, or the following heterocycles:

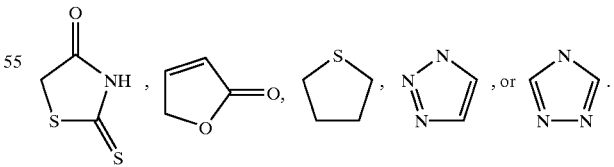

As used herein, the term "9- or 10-membered heterobicycle" or "heterobicycle" either alone or in combination with another radical, means a heterocycle as defined above fused to one or more other cycle, be it a heterocycle or any other cycle. Examples of such heterobicycles include, but are not limited to, thiazolo[4,5-b]-pyridine, quinoline, or indole, or the following:

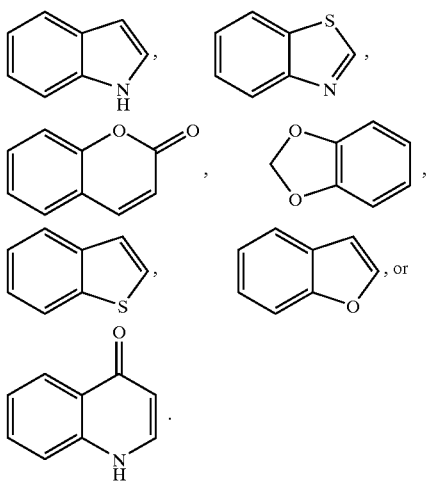

As used herein, the term "Het" defines a 5- or 6-membered heterocycle having 1 to 4 heteroatoms selected from O, N, and S, or a 9- or 10-membered heterobicycle having 1 to 5 heteroatoms wherever possible, selected from O, N and S.

As used herein, the term "halo" means a halogen atom and includes fluorine, chlorine, bromine and iodine.

As used herein, the term "haloalkyl" is intended to mean an alkyl that is described above in which each hydrogen atom may be successively replaced by a halogen atom, for example $CH_2Br$ or $CF_3$.

As used herein, the term "metal halide" is intended to mean any metal that is bonded to a halogen atom for use in a metal-catalyzed cross-coupling reaction. Examples of such metal halides include, but are not limited to, —MgCl, —CuCl, or —ZnCl and the like.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as SOR, $SO_2R$, or $SO_3R$.

It is intended that the term "substituted" when applied in conjunction with a radical having more than one moiety such as $C_{1-6}$alkyl-aryl, or $C_{1-6}$alkyl-Het, such substitution applies to both moieties i.e. both the alkyl and aryl or Het moieties can be substituted with the defined substituents.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, boronic acids or tetrazole.

As used herein, the term "functional group equivalent" is intended to mean an element or a substituted derivative thereof, that is replaceable by another element that has similar electronic, hybridization or bonding properties.

As used herein, the term "metal catalyst" is intended to mean a metal such as palladium (0) or palladium (2) that is bonded to a leaving group for use in a cross-coupling reaction. Examples of such palladium catalysts include, but are not limited to, $Pd(Ph_3)_4$, Pd/C, $Pd(OAc)_2$, $PdCl_2$, and the like. Alternative metals that can catalyze cross-coupling reactions include, but are not limited to: $Ni(acac)_2$, $Ni(OAc)_2$, or $NiCl_2$.

As used herein, the term "derivative" is intended to mean "detectable label", "affinity tag" or "photoreactive group". The term "detectable label" refers to any group that may be linked to the polymerase or to a compound of the present invention such that when the compound is associated with the polymerase target, such label allows recognition either directly or indirectly of the compound such that it can be detected, measured and quantified. Examples of such "labels" are intended to include, but are not limited to, fluorescent labels, chemiluminescent labels, colorimetric labels, enzymatic markers, radioactive isotopes and affinity tags such as biotin. Such labels are attached to the compound or to the polymerase by well known methods. The term "affinity tag" means a ligand (that is linked to the polymerase or to a compound of the present invention) whose strong affinity for a receptor can be used to extract from a solution the entity to which the ligand is attached. Examples of such ligands include biotin or a derivative thereof, a histidine polypeptide, a polyarginine, an amylose sugar moiety or a defined epitope recognizable by a specific antibody. Such affinity tags are attached to the compound or to the polymerase by well-known methods.

The term "photoreactive group" means a group that is transformed, upon activation by light, from an inert group to a reactive species, such as a free radical. Examples of such groups include, but are not limited to, benzophenones, azides, and the like.

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1–19, incorporated herein by reference).

Preferred Embodiments

Preferably, compounds of the present invention have the following formula I as defined above, wherein preferably:

$R^1$ is selected from: $(C_{3-7})$cycloalkyl, $(C_{5-7})$cycloalkenyl, 6 or 10-membered aryl, or Het each of which being optionally substituted with 1 or 2 halogen or from 1 or 2 substituents selected from:
a) $(C_{1-6})$alkyl, $(C_{3-7})$cycloalkyl, $(C_{2-6})$alkenyl, each optionally substituted with $OR^{11}$, $SR^{11}$, wherein $R^{11}$ is H, $(C_{1-6}$alkyl$)$, $(C_{3-7})$cycloalkyl, or $(C_{1-6})$alkyl-$(C_{3-7})$cycloalkyl;
b) $OR^{13}$ wherein $R^{13}$ is H, $(C_{1-6}$alkyl$)$, $(C_{3-7})$cycloalkyl, $(C_{1-6})$alkyl-$(C_{3-7})$cycloalkyl, a 6- or 10-membered aryl, or Het; and
f) a 6- or 10-membered aryl, or Het said aryl or Het being optionally substituted with $(C_{1-6})$alkyl, $(C_{3-7})$cycloalkyl or $(C_{1-6})$alkyl-$(C_{3-7})$cycloalkyl.

More preferably, $R^1$ is selected from: 6 or 10-membered aryl, or Het each of which being optionally substituted with 1 or 2 halogen or with 1 or 2 $(C_{1-6})$alkyl or $(C_{2-6})$alkenyl.

Most preferably, $R^1$ is phenyl or Het optionally substituted with $(C_{1-6})$alkyl.

Even most preferably, R¹ is:

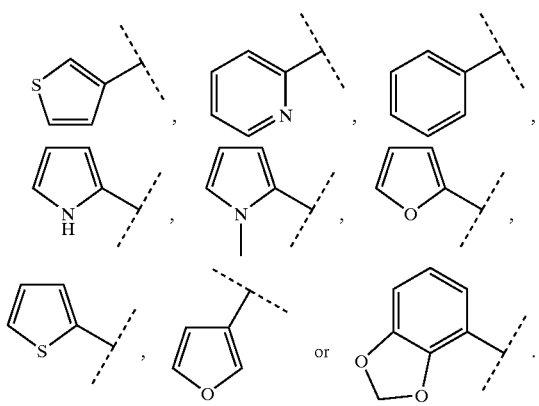

Still, even most preferably, R¹ is:

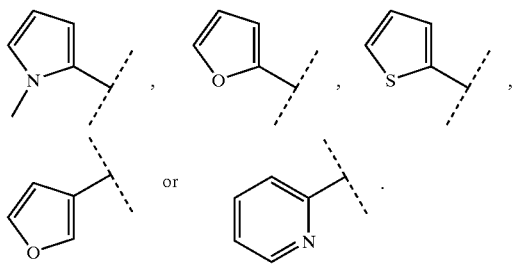

Preferably, R² is selected from (C$_{3-7}$)cycloalkyl, (C$_{6-10}$) bicycloalkyl, each optionally substituted with 1 or 2 substituents selected from:
a) halogen, (C$_{1-6}$)alkyl, OH and (C$_{1-6}$)alkoxy.
More preferably, R² is selected from (C$_{3-7}$)cycloalkyl, (C$_{6-10}$)bicycloalkyl, each optionally mono- or di-substituted with halogen or (C$_{1-6}$)alkyl. Most preferably, R² is selected from (C$_{3-7}$)cycloalkyl or (C$_{6-10}$)bicycloalkyl. Even most preferably, R² is cyclopentyl, cyclohexyl, or

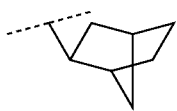

Still, even most preferably, R² is cyclopentyl or cyclohexyl. or cyclohexyl.

Preferably, B is N or CR⁵, wherein R⁵ is H, halogen, haloalkyl or (C$_{1-6}$)alkyl. More preferably, B is N, CH or C—(C$_{1-6}$)alkyl). Most preferably, B is N, CH or C(Me). Even most preferably B is CH.

Preferably, X is N, CH or C(C$_{1-6}$)alkyl. More preferably, X is N, CH or C(Me). Most preferably, X is N or CH. Even most preferably, X is CH.

Preferably, D is CR⁵, wherein R⁵ is H, halogen, haloalkyl, or (C$_{1-6}$)alkyl. More preferably, D is CH or C(Me). Most preferably, D is CH.

Preferably, Y¹ is O.
Preferably, Y² is O.
More preferably both Y¹ and Y² are O.
Preferably, Z is N, or NH or O. More preferably, Z is NH or O. Most preferably, Z is NH.

Preferably, R³ and R⁴ are each independently H, (C$_{1-6}$) alkyl, first (C$_{3-7}$)cycloalkyl, 6- or 10-membered aryl, Het (C$_{1-6}$)alkyl-6- or 10-membered aryl, (C$_{1-6}$)alkyl-Het; or R³ and R⁴ are covalently bonded together to form second (C$_{3-7}$)cycloalkyl or a 5- or 6-membered heterocycle having from 1 to 4 heteroatom selected from O, N, and S;

wherein said alkyl, first and second cycloalkyl, aryl, Het (C$_{1-6}$)alkyl-aryl, (C$_{1-6}$)alkyl-Het or heterocycle are optionally substituted with: 1 or 2 substituents selected from:
a) (C$_{1-6}$)alkyl, (C$_{3-7}$)cycloalkyl or (C$_{2-4}$)alkenyl; and
c) OR³¹ or COOR³¹, wherein R³¹ is H or (C$_{1-6}$)alkyl;

or when Z is N, both R³ or R⁴ are covalently bonded thereto to form a nitrogen-containing 5- or 6-membered heterocycle.

More preferably, R³ and R⁴ are each independently H, (C$_{1-6}$)alkyl, (C$_{3-7}$)cycloalkyl, phenyl, Het (C$_{1-6}$)alkyl-aryl or (C$_{1-6}$)alkyl-Het;

or R³ and R⁴ are covalently bonded together to form cyclopropyl, cyclobutyl, cyclopentyl or cyclohexyl, 5- or 6-membered heterocycle having from 1 or 2 heteroatom selected from N or S;
wherein said alkyl, cycloalkyl, aryl, Het (C$_{1-6}$)alkyl-aryl, (C$_{1-6}$)alkyl-Het cyclopropyl, cyclobutyl, cyclopentyl or cyclohexyl or heterocycle are optionally substituted with from 1 or 2 substituents selected from:
a) (C$_{1-6}$)alkyl, (C$_{3-7}$)cycloalkyl, or (C$_{2-4}$)alkenyl; and
c) OH or COO(C$_{1-6}$)alkyl.

Most preferably, R³ and R⁴ are each independently H, (C$_{1-6}$)alkyl, (C$_{3-7}$)cycloalkyl, (C$_{1-6}$)alkyl-(C$_{3-7}$)cycloalkyl, phenyl, Het (C$_{1-6}$)alkyl-phenyl, (C$_{1-6}$)alkyl-Het; or R³ and R⁴ are covalently bonded together to form cyclopropyl, cyclobutyl, cyclopentyl or cyclohexyl all optionally substituted with OH, (C$_{1-6}$alkyl) or (C$_{2-4}$)alkenyl; or R³ and R⁴ form a piperidine or a pyrrolidine both optionally substituted with (C$_{1-6}$alkyl) or COO(C$_{1-6}$)alkyl.

Even most preferably, R³ is H or (C$_{1-6}$)alkyl and R⁴ is H, (C$_{1-6}$)alkyl, (C$_{3-7}$)cycloalkyl, (C$_{1-6}$)alkyl-phenyl, phenyl, (C$_{1-6}$)alkyl-(C$_{3-7}$)cycloalkyl, or (C$_{1-6}$)alkyl-biphenyl.

Still most preferably R³ and R⁴ are both H or both CH₃;
or R³ is H and R⁴ is selected from:

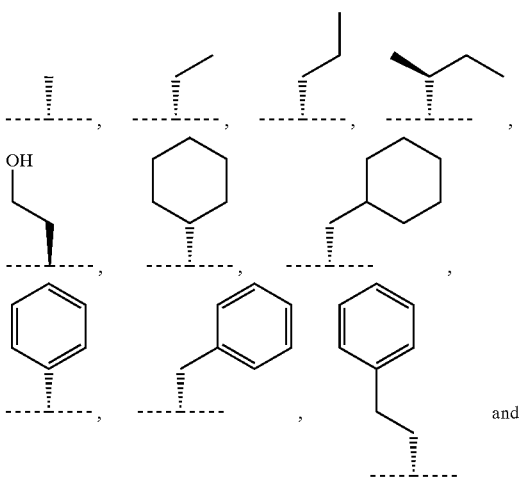

and

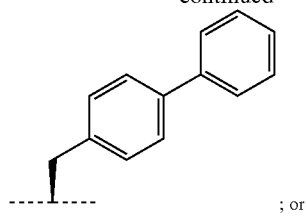
; or

R³ and R⁴ are bonded together and form:

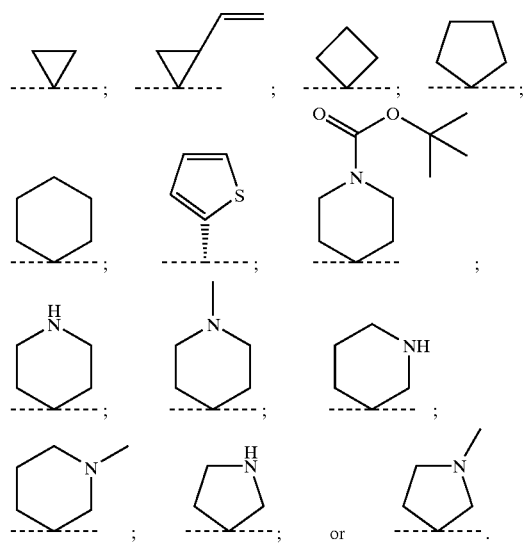

Preferably, R⁷ is H or ($C_{1-6}$alkyl). More preferably, R⁷ is H or Me. Most preferably, R⁷ is H.

Preferably, A is 6- or 10-membered aryl, Het or ($C_{1-6}$) alkyl-CONH-aryl, said aryl and Het being optionally substituted with:

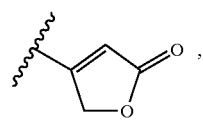

halogen, or 1 to 2 substituents selected from:
  a) ($C_{1-6}$)alkyl, ($C_{1-6}$) haloalkyl, ($C_{3-7}$)cycloalkyl, ($C_{2-6}$) alkenyl, ($C_{2-8}$)alkynyl, all of which are optionally substituted with:
    ($C_{1-6}$)alkyl or ($C_{3-7}$)cycloalkyl, both optionally substituted with a 6 or 10-membered aryl or Het;
    $OR^{101}$ or $COOR^{101}$ wherein each $R^{101}$ is independently H or ($C_{1-6}$)alkyl;
  b) $OR^{104}$ wherein $R^{104}$ is H or ($C_{1-6}$alkyl) optionally substituted with: COOH or COO($C_{1-6}$)alkyl;
  d) $SR^{108}$, wherein $R^{108}$ is H or ($C_{1-6}$)alkyl optionally substituted with COOH or COO($C_{1-6}$)alkyl;
  e) $NR^{111}R^{112}$ wherein $R^{111}$ and $R^{112}$ are both H; or $R^{111}$ is H and $R^{112}$ is Het optionally substituted with ($C_{1-6}$)alkyl or $COOR^{115}$ wherein $R^{115}$ is H, ($C_{1-6}$) alkyl, ($C_{3-7}$)cycloalkyl, or ($C_{1-6}$)alkyl-($C_{3-7}$) cycloalkyl;
  j) tetrazole, COOH or COO($C_{1-6}$)alkyl;
  k) $CONR^{129}R^{130}$ wherein $R^{129}$ and $R^{130}$ are each independently H or ($C_{1-6}$)alkyl optionally substituted with COOH or COO($C_{1-6}$)alkyl; and
  l) 6- or 10-membered aryl or Het said aryl or Het being optionally substituted with from 1 to 4 substituents selected from:
    i) ($C_{1-6}$)alkyl or haloalkyl;
    ii) $OR^{104}$, wherein $R^{104}$ is H, or ($C_{1-6}$)alkyl) optionally substituted with COOH or COO($C_{1-6}$)alkyl; and
    iii) $COOR^{128}$ $NR^{111}R^{112}$ or $CON(R^{129}R^{130})_2$, wherein $R^{128}$, $R^{111}$, $R^{112}$, $R^{129}$ and $R^{130}$ are independently H or ($C_{1-6}$)alkyl.

More preferably A is a 6- or 10-membered aryl, or Het said aryl or Het being optionally substituted with:

halogen, or 1 to 2 substituents selected from:
  a) ($C_{1-6}$)alkyl, ($C_{2-6}$)alkenyl, ($C_{2-8}$)alkynyl, said alkyl and alkenyl being optionally substituted with:
    OH, ($C_{1-6}$)alkoxy, or COOH;
  b) OH or O($C_{1-6}$alkyl)COOH;
  d) SH or S($C_{1-6}$)alkylCOOH;
  j) tetrazole or COOH; and
  l) furan or thiazole mono or di-substituted with:
    i) ($C_{1-6}$)alkyl; or
    iii) COOH or $CONH_2$.

Most preferably, A is phenyl, indole, benzofuran, benzothiophene, coumarin or quinolone, all of which being optionally substituted with:

iodine, or 1 to 2 substituents selected from:
  a) ($C_{1-6}$)alkyl, ($C_{2-6}$)alkenyl, ($C_{2-8}$)alkynyl, said alkyl and alkenyl being optionally substituted with:
    OH, ($C_{1-6}$)alkoxy, or COOH;
  b) OH or O($C_{1-6}$alkyl)COOH;
  d) SH or S($C_{1-6}$)alkylCOOH;
  j) COOH; and
  l) furan or thiazole mono or di-substituted with:
    i) ($C_{1-6}$)alkyl; or
    iii) COOH or $CONH_2$.

Even most preferably A is

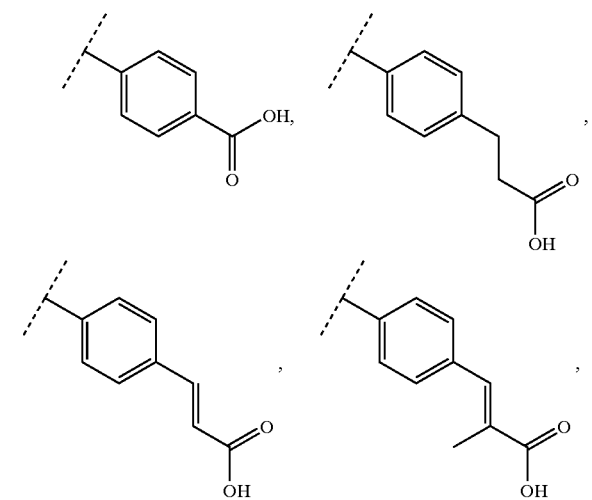

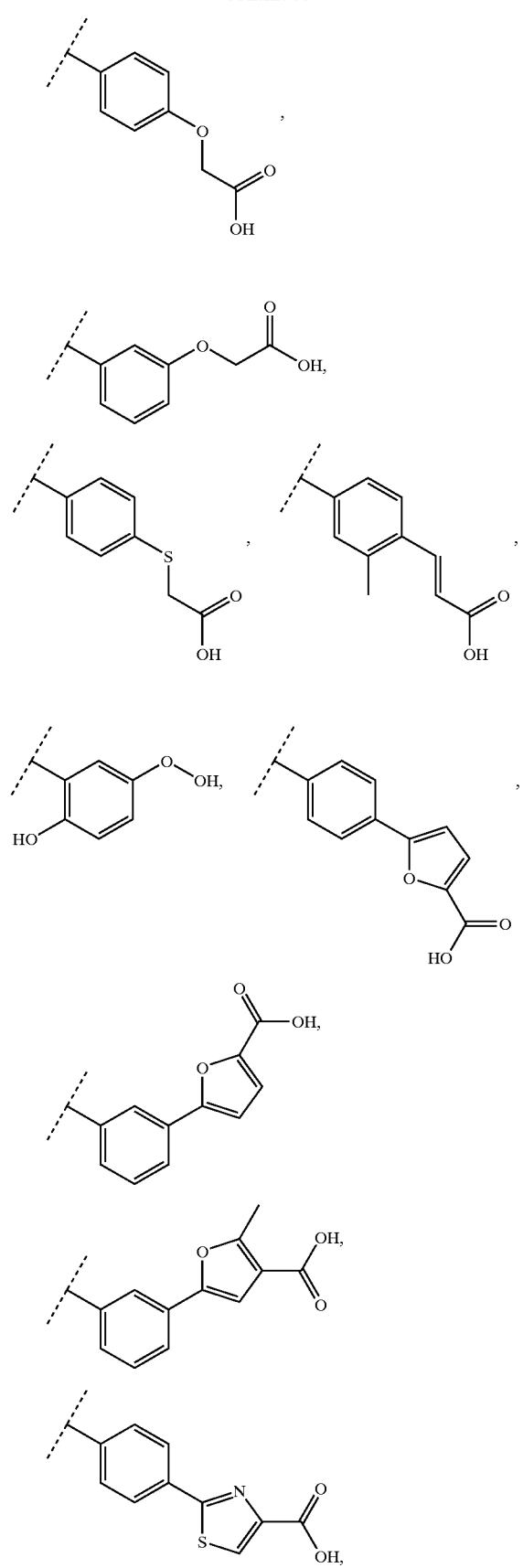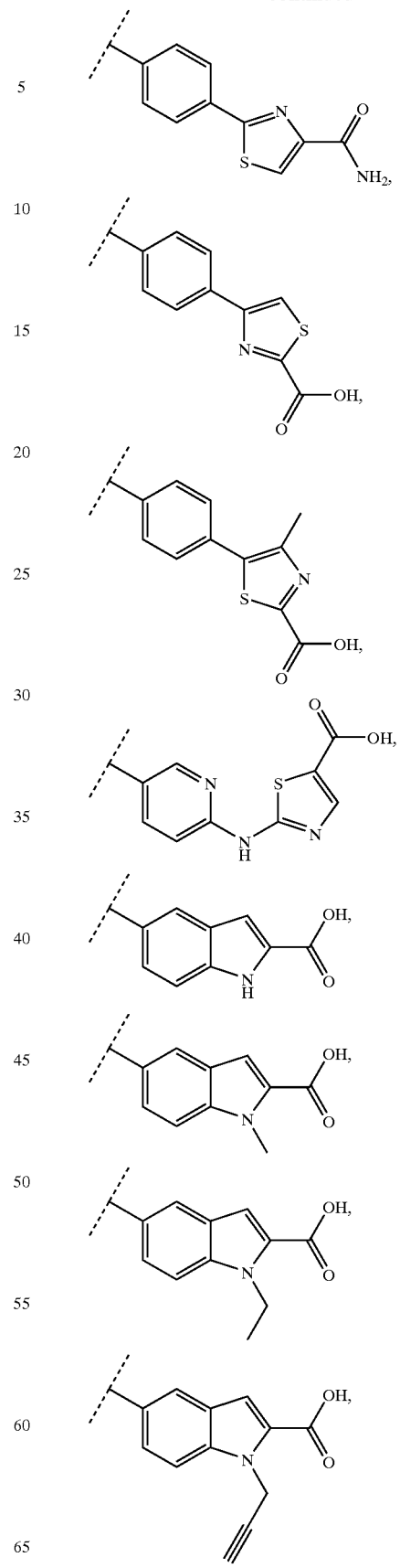

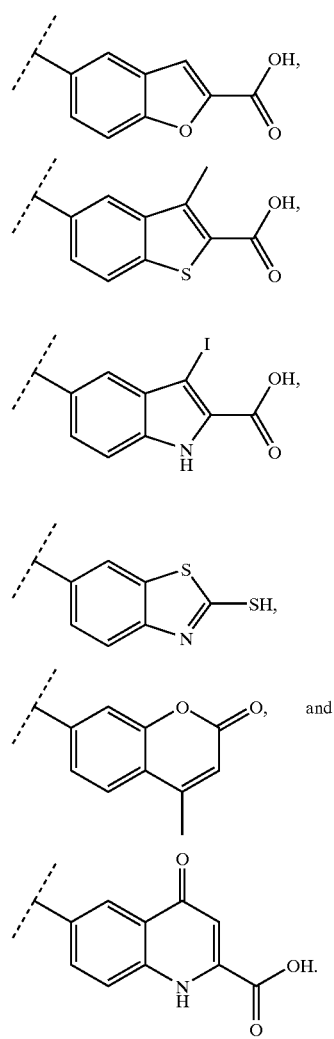
Sill, even most preferably A is selected from:
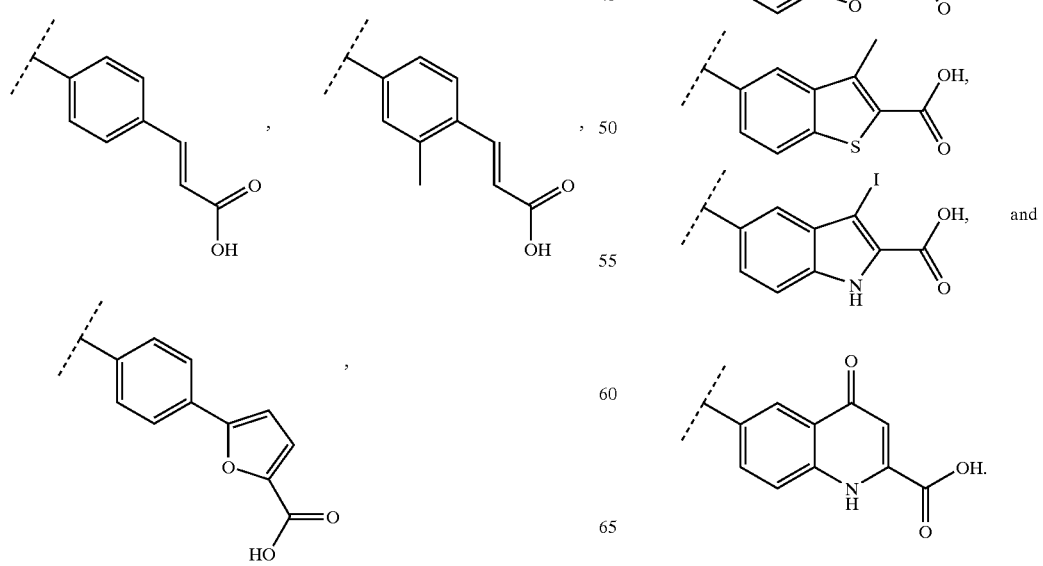

Preferably, compounds of the invention have the following formula:

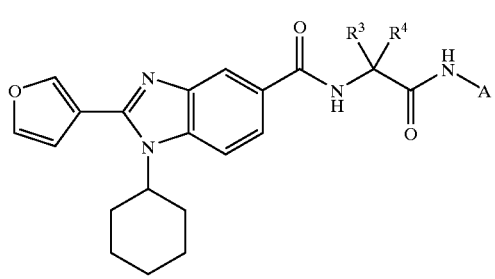

II wherein $R^3$ and $R^4$ are each independently H, $(C_{1-6})$alkyl, first $(C_{3-7})$cycloalkyl, 6- or 10-membered aryl, Het $(C_{1-6})$alkyl-6- or 10-membered aryl, $(C_{1-6})$alkyl-Het;
or $R^3$ and $R^4$ are covalently bonded together to form second $(C_{3-7})$cycloalkyl or a 5- or 6-membered heterocycle having from 1 to 4 heteroatom selected from O, N, and S;
wherein said alkyl, first and second cycloalkyl, aryl, Het $(C_{1-6})$alkyl-aryl, $(C_{1-6})$alkyl-Het or heterocycle are optionally substituted with from 1 or 2 substituents selected from:
a) $(C_{1-6})$alkyl, $(C_{3-7})$cycloalkyl or $(C_{2-4})$alkenyl; and
c) $OR^{31}$ or $COOR^{31}$, wherein each $R^{31}$ is independently H or $(C_{1-6})$alkyl; and A is a 6- or 10-membered aryl, Het, or $(C_{1-6})$alkyl-CONH-aryl, said aryl or Het being optionally substituted with:

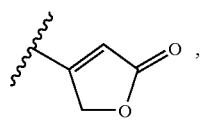

halogen, or
1 to 2 substituents selected from:
a) $(C_{1-6})$alkyl, haloalkyl, $(C_{3-7})$cycloalkyl, $(C_{2-6})$alkenyl, $(C_{2-8})$alkynyl, all of which are optionally substituted with:
$(C_{1-6})$alkyl, $(C_{3-7})$cycloalkyl, both optionally substituted with a 6 or 10-membered aryl, or Het;
b) $OR^{101}$, or $COOR^{101}$ wherein $R^{101}$ is H or $(C_{1-6})$alkyl;
b) $OR^{104}$ wherein $R^{104}$ is H or $(C_{1-6}$alkyl) optionally substituted with: COOH or $COO(C_{1-6})$alkyl;
c) $SR^{108}$ wherein $R^{108}$ is H or $(C_{1-6})$alkyl optionally substituted with COOH or $COO(C_{1-6})$alkyl;
d) $NR^{111}R^{112}$ wherein both $R^{111}$ and $R^{112}$ are H; or $R^{111}$ is H and $R^{112}$ is Het optionally substituted with $(C_{1-6})$alkyl or $COOR^{115}$ wherein $R^{115}$ is H, $(C_{1-6})$alkyl, $(C_{3-7})$cycloalkyl, or $(C_{1-6})$alkyl-$(C_{3-7})$cycloalkyl;
e) COOH or $COO(C_{1-6})$alkyl; and
f) $CONR^{129}R^{130}$ wherein $R^{129}$ and $R^{130}$ are independently H or $(C_{1-6})$alkyl optionally substituted with COOH or $COO(C_{1-6})$alkyl; and
g) 6- or 10-membered aryl or Het said aryl or Het being optionally substituted with from 1 to 4 substituents selected from:
i) $(C_{1-6})$alkyl or haloalkyl;
ii) $OR^{104}$. wherein $R^{104}$ is H or $(C_{1-6})$alkyl) optionally substituted with COOH or $COO(C_{1-6})$alkyl; and
iii) $COOR^{128}$, $NR^{111}R^{112}$ or $CON(R^{129}R^{130})_2$, wherein $R^{128}$, $R^{111}$, $R^{112}$, $R^{129}$ and $R^{130}$ are independently H or $(C_{1-6})$alkyl.

Preferably, compounds of the invention have the following formula:

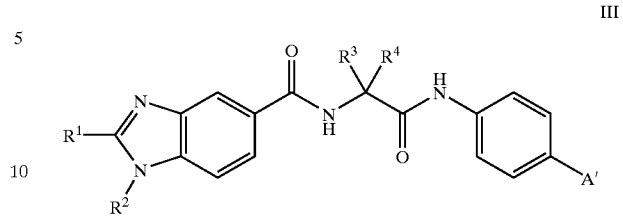

III wherein
$R^1$ is selected from: $(C_{3-7})$cycloalkyl, $(C_{5-7})$cycloalkenyl, 6 or 10-membered aryl or Het each of which being optionally substituted with 1 or 2 halogen or from 1 or 2 substituents selected from:
a) $(C_{1-6})$alkyl, $(C_{2-6})$alkenyl, $(C_{3-7})$cycloalkyl, each optionally substituted with $OR^{11}$ or $SR^{11}$ wherein $R^{11}$ is H, $(C_{1-6}$alkyl), $(C_{3-7})$cycloalkyl, or $(C_{1-6})$alkyl-$(C_{3-7})$cycloalkyl;
b) $OR^{13}$ wherein $R^{13}$ is H, $(C_{1-6}$alkyl), $(C_{3-7})$cycloalkyl, $(C_{1-6})$alkyl-$(C_{3-7})$cycloalkyl, a 6- or 10-membered aryl, or Het; and
f) a 6- or 10-membered aryl, or Het said aryl or Het being optionally substituted with $(C_{1-6})$alkyl, $(C_{3-7})$cycloalkyl or $(C_{1-6})$alkyl-$(C_{3-7})$cycloalkyl;

$R^2$ is selected from $(C_{3-7})$cycloalkyl, $(C_{6-10})$bicycloalkyl, each optionally substituted with 1 or 2 substituents selected from: halogen, $(C_{1-6})$alkyl, OH, and $(C_{1-6})$alkoxy;

$R^3$ and $R^4$ are each independently H, $(C_{1-6})$alkyl, first $(C_{3-7})$cycloalkyl, 6- or 10-membered aryl, Het $(C_{1-6})$alkyl-6- or 10-membered aryl, $(C_{1-6})$alkyl-Het;
or $R^3$ and $R^4$ are covalently bonded together to form second $(C_{3-7})$cycloalkyl, 5- or 6-membered heterocycle having from 1 to 4 heteroatom selected from O, N, and S;
wherein said alkyl, first and second cycloalkyl, aryl, Het $(C_{1-6})$alkyl-aryl, $(C_{1-6})$alkyl-Het or heterocycle are optionally substituted with from 1 or 2 substituents selected from:
a) $(C_{1-6})$alkyl, $(C_{3-7})$cycloalkyl or $(C_{2-4})$alkenyl; and
c) $OR^{31}$ or $COOR^{31}$, wherein $R^{31}$ is H or $(C_{1-6})$alkyl; and A' is a 6- or 10-membered aryl, Het, or $(C_{1-6})$alkyl-CONH-aryl, said aryl or Het being optionally substituted with:

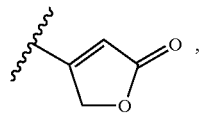

halogen, or
1 to 2 substituents selected from:
a) $(C_{1-6})$alkyl, $(C_{1-6})$ haloalkyl, $(C_{3-7})$cycloalkyl, $(C_{2-6})$alkenyl, $(C_{2-8})$alkynyl, all of which are optionally substituted with:
second $(C_{1-6})$alkyl or second $(C_{3-7})$cycloalkyl, said second alkyl or second cycloalkyl being optionally substituted with a 6 or 10-membered aryl or Het;

b) OR$^{104}$ wherein R$^{104}$ is H or (C$_{1-6}$alkyl) optionally substituted with: COOH or COO(C$_{1-6}$)alkyl;
c) SR$^{108}$, wherein R$^{108}$ is H or (C$_{1-6}$)alkyl optionally substituted with COOH or COO(C$_{1-6}$)alkyl;
d) NR$^{111}$R$^{112}$ wherein R$^{111}$ and R$^{112}$ are both H; or R$^{111}$ is H and R$^{112}$ is Het optionally substituted with (C$_{1-6}$)alkyl or COOR$^{115}$ wherein R$^{115}$ is H, (C$_{1-6}$)alkyl, (C$_{3-7}$)cycloalkyl, or (C$_{1-6}$)alkyl-(C$_{3-7}$)cycloalkyl; COOH or COO(C$_{1-6}$)alkyl;
e) CONR$^{129}$R$^{130}$ wherein R$^{129}$ and R$^{130}$ are each independently H or (C$_{1-6}$)alkyl optionally substituted with COOH or COO(C$_{1-6}$)alkyl; and
f) 6- or 10-membered aryl or Het, said aryl or Het being optionally substituted with from 1 to 4 substituents selected from:
  i) (C$_{1-6}$)alkyl or haloalkyl;
  ii) OR$^{104}$ wherein R$^{104}$ is H, or (C$_{1-6}$)alkyl) optionally substituted with COOH or COO(C$_{1-6}$)alkyl; and
  iii) COOR$^{128}$, NR$^{111}$R$^{112}$ or CON(R$^{129}$R$^{130}$)$_2$, wherein R$^{128}$, R$^{111}$, R$^{112}$, R$^{129}$ and R$^{130}$ are independently H or (C$_{1-6}$)alkyl.

Preferably, compounds of the invention have the following formula:

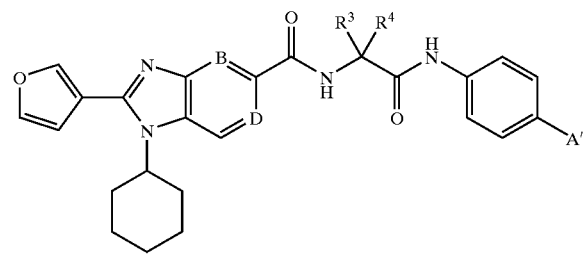

IV wherein
D is CH or C(C$_{1-6}$)alkyl;
B is N, CH, or C(C$_{1-6}$)alkyl;
R$^3$ and R$^4$ are each independently H, (C$_{1-6}$)alkyl, first (C$_{3-7}$)cycloalkyl, 6- or 10-membered aryl, Het (C$_{1-6}$)alkyl-6- or 10-membered aryl, (C$_{1-6}$)alkyl-Het;
or R$^3$ and R$^4$ are covalently bonded together to form second (C$_{3-7}$)cycloalkyl, 5- or 6-membered heterocycle having from 1 to 4 heteroatom selected from O, N, and S;
  wherein said alkyl, first and second cycloalkyl, aryl, Het (C$_{1-6}$)alkyl-aryl, (C$_{1-6}$)alkyl-Het or heterocycle are optionally substituted with from 1 or 2 substituents selected from:
  a) (C$_{1-6}$)alkyl, (C$_{3-7}$)cycloalkyl or (C$_{2-4}$)alkenyl; and
  c) OR$^{31}$ or COOR$^{31}$, wherein R$^{31}$ is H or (C$_{1-6}$)alkyl; and
A' is a 6- or 10-membered aryl, Het or (C$_{1-6}$)alkyl-CONH-aryl, said aryl or Het being optionally substituted with:

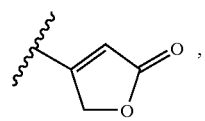

halogen, or
1 to 2 substituents selected from:
  a) (C$_{1-6}$)alkyl, (C$_{1-6}$) haloalkyl, (C$_{3-7}$)cycloalkyl, (C$_{2-6}$)alkenyl, (C$_{2-8}$)alkynyl, all of which are optionally substituted with:

second (C$_{1-6}$)alkyl or second (C$_{3-7}$)cycloalkyl, said second alkyl or second cycloalkyl being optionally substituted with a 6 or 10-membered aryl or Het;
OR$^{101}$ or COOR$^{101}$ wherein each R$^{101}$ is independently H or (C$_{1-6}$)alkyl;
b) OR$^{104}$ wherein R$^{104}$ is H or (C$_{1-6}$alkyl) optionally substituted with: COOH or COO(C$_{1-6}$)alkyl;
d) SR$^{108}$, wherein R$^{108}$ is H or (C$_{1-6}$)alkyl optionally substituted with COOH or COO(C$_{1-6}$)alkyl;
e) NR$^{111}$R$^{112}$ wherein R$^{111}$ and R$^{112}$ are both H; or R$^{111}$ is H and R$^{112}$ is Het optionally substituted with (C$_{1-6}$)alkyl or COOR$^{115}$ wherein R$^{115}$ is H, (C$_{1-6}$)alkyl, (C$_{3-7}$)cycloalkyl, or (C$_{1-6}$)alkyl-(C$_{3-7}$)cycloalkyl;
f) COOH or COO(C$_{1-6}$)alkyl;
g) CONR$^{129}$R$^{130}$ wherein R$^{129}$ and R$^{130}$ are each independently H or (C$_{1-6}$)alkyl optionally substituted with COOH or COO(C$_{1-6}$)alkyl; and
h) 6- or 10-membered aryl or Het said aryl or Het being optionally substituted with from 1 to 4 substituents selected from:
  i) (C$_{1-6}$)alkyl or haloalkyl;
  ii) OR$^{104}$ wherein R$^{104}$ is H, or (C$_{1-6}$)alkyl) optionally substituted with COOH or COO(C$_{1-6}$)alkyl; and
  iii) COOR$^{128}$, NR$^{111}$R$^{112}$ or CON(R$^{129}$R$^{130}$)$_2$, wherein R$^{128}$, R$^{111}$, R$^{112}$, R$^{129}$ and R$^{130}$ are independently H or (C$_{1-6}$)alkyl.

Specific Embodiments

Included within the scope of this invention are all compounds of formula I as presented in Tables 1 to 3.

Polymerase Activity

The ability of the compounds of formula I to inhibit RNA synthesis by the RNA dependent RNA polymerase of HCV can be demonstrated by any assay capable of measuring RNA dependent RNA polymerase activity. A suitable assay is described in the examples.

Specificity for RNA Dependent DNA Polymerase Activity

To demonstrate that the compounds of the invention act by specific inhibition of HCV polymerase, the compounds may be tested for inhibitory activity in a DNA dependent RNA polymerase assay.

When a compound of formula I or one of its therapeutically acceptable salts, is employed as an antiviral agent, it is administered orally, topically or systemically to mammals, e.g. humans, rabbits or mice, in a vehicle comprising one or more pharmaceutically acceptable carriers, the proportion of which is determined by the solubility and chemical nature of the compound, chosen route of administration and standard biological practice.

For oral administration, the compound of formula I or a therapeutically acceptable salt thereof can be formulated in unit dosage forms such as capsules or tablets each containing a predetermined amount of the active ingredient, ranging from about 25 to 500 mg, in a pharmaceutically acceptable carrier.

For topical administration, the compound of formula I can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula I is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound of formula I or a therapeutically acceptable salt is administered in the range of 10 to 200 mg per kilogram of body weight per day, with a preferred range of 25 to 150 mg per kilogram.

For systemic administration, the compound of formula I is administered at a dosage of 10 mg to 150 mg per kilogram of body weight per day, although the aforementioned variations will occur. A dosage level that is in the range of from about 10 mg to 100 mg per kilogram of body weight per day is most desirably employed in order to achieve effective results.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV polymerase or to treat or prevent HCV virus infection. Such treatment may also be achieved using the compounds of this invention in combination with agents which include, but are not limited to: immunomodulatory agents, such as α-, β-, δ-, or γ-interferons; other antiviral agents such as ribavirin, amantadine; other inhibitors of HCV NS5B polymerase; inhibitors of other targets in the HCV life cycle, which include but are not limited to, helicase, NS2/3 protease, NS3 protease, or internal ribosome entry site (IRES); or combinations thereof. The additional agents may be combined with the compounds of this invention to create a single dosage form. Alternatively these additional agents may be separately administered to a mammal as part of a multiple dosage form.

Methodology and Synthesis

Benzimidazole derivatives or analogs according to the present invention can be prepared from known starting materials by following Scheme 1, shown below wherein $R^1$, $R^2$, $R^3$, $R^4$, $R^7$, and A are as described herein.

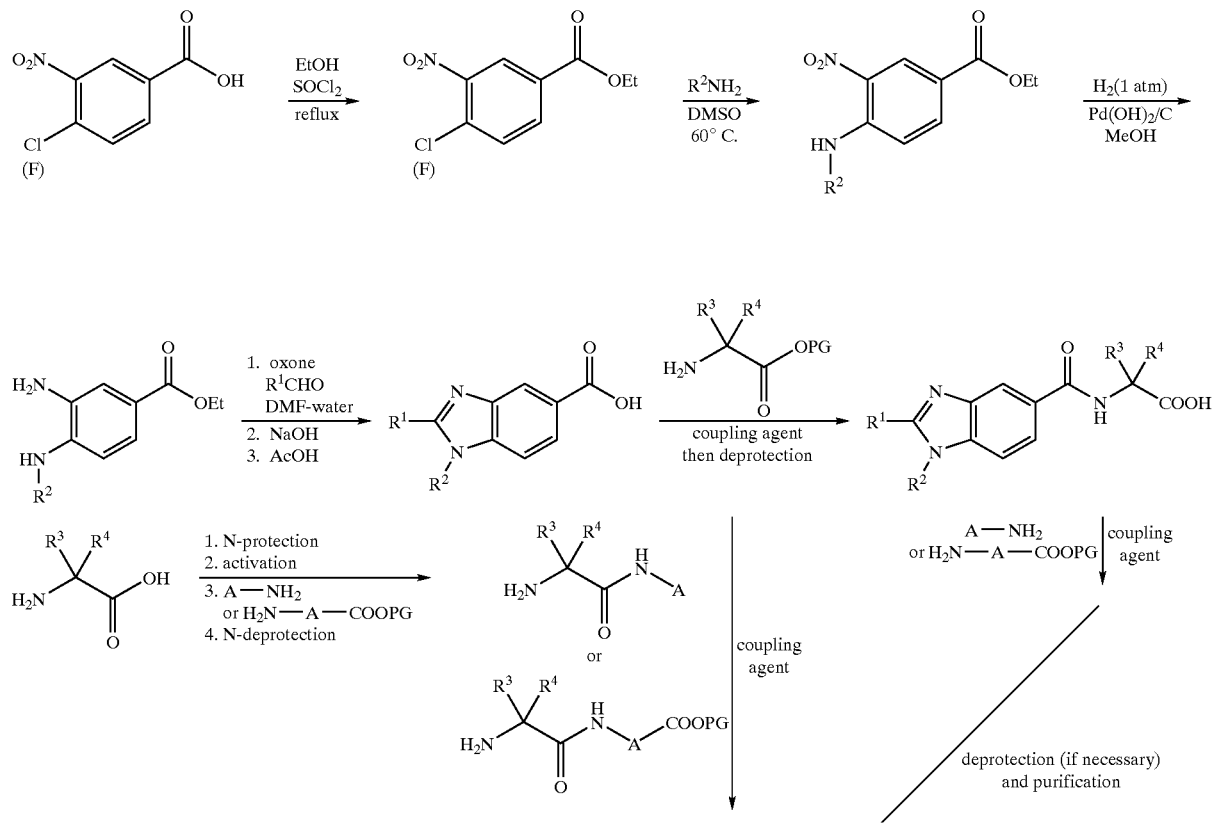

In carrying out the route illustrated in Scheme 1, a suitably protected form of 4-chloro-3-nitrobenzoic acid or 4-fluoro-3-nitrobenzoic acid is reacted with a primary amine $R^2NH_2$. Amines are of commercial sources or can be prepared by literature methods. This reaction is carried out in a suitable solvent such as DMSO, DMF or the like, at temperatures ranging from 20° C. to 170° C., or alternatively without solvent by heating the two components together. The nitro group of these derivatives is subsequently reduced to the corresponding aniline, using a reducing agent such as hydrogen gas or a formate salt in the presence of a catalyst (e.g. Pd metal and the like), metals in the presence of mineral acids (e.g. Fe or Zn with aqueous HCl), or metal salts ($SnCl_2$). The diamino derivatives that are obtained are condensed with commercially available aldehydes $R^2CHO$ in the presence of an oxidizing agent (e.g. air, oxygen, iodine, oxone®, quinones, peroxides etc.) to give benzimidazole 5-carboxylates.

Alternatively, other methods for benzimidazole ring construction can be employed, such as condensation of the diamino derivatives with carboxylic acids, nitriles or amides, in the presence or absence of a catalyst. Such methods are well known in the literature to those skilled in the art. Saponification of the ester protecting group of such derivatives using alkali metal hydroxides, followed by neutralization with weak acids (e.g. AcOH) generates free 5-carboxybenzimidazoles. Alternatively, 5-carboxybenzimidazole derivatives such as those described above can be prepared on a solid support as described in Scheme 2:

Scheme 2

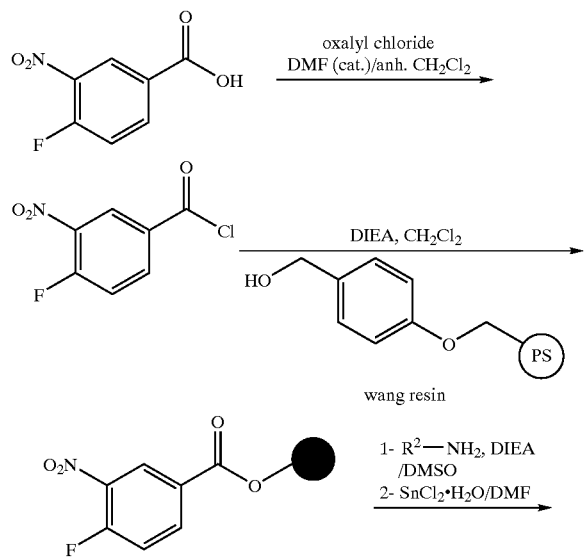

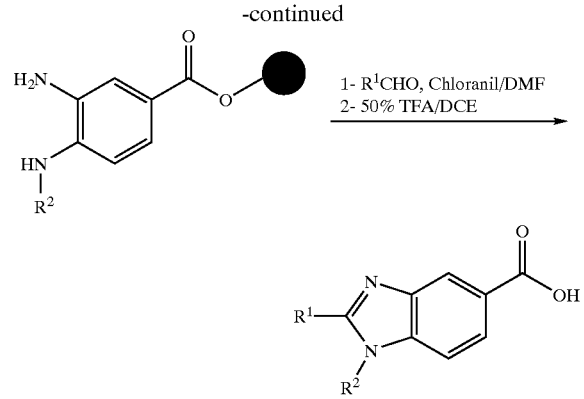

In carrying out the synthetic route illustrated in Scheme 2, 4-fluoro-3-nitrobenzoic acid is converted to the acid chloride derivative using standard procedures (e.g. thionyl chloride, oxalyl chloride, phosgene and the like in the presence of a catalytic amount of DMF) in an inert solvent such as DCM. Wang resin is esterified with this acid chloride by condensation in the presence of an organic tertiary amine such as $Et_3N$, N-methylmorpholine, DIEA and the like. Other types of resins are well known to those skilled in the art, for example Rink resin, which may be functionalized without deviating from the scope of the invention. The functionalized resin thus obtained is then elaborated to resin-bound benzimidazole carboxylate derivatives as described above for the solution-phase chemistry. Cleavage of the benzimidazole from the resin is carried out with strong acids (e.g. trifluoroacetic acid) to give benzimidazole 5-carboxylic acids.

Derivatives of formula I may be obtained by condensation of 5-carboxybenzimidazole derivatives such as those described above with suitably protected forms of an amino acid derivative $H_2NCR^3R^4COOPG$ (where PG serves as a carboxylic acid protecting group, e.g. Me, Et, tBu etc.) through formation of an amide bond. Condensation of the carboxylic acid with $H_2NCR^3R^4COOPG$ can be accomplished using standard peptide bond forming reagents such as TBTU, HATU, BOP, BroP, EDAC, DCC, isobutyl chloroformate, $PCl_5$ and the like, or by activation of the carboxyl group by conversion to the corresponding acid chloride prior to condensation with the amino acid derivative. This coupling reaction is then followed by deprotection of the ester (COOPG) to a free carboxylic acid group which is then condensed with amine derivatives of formula $H_2N$—A to provide compounds of formula I after removal of any remaining protecting groups.

Alternatively, N-protected amino acid derivatives of formula $P'HNCR^3R^4COOH$ (where P' is a nitrogen protecting group such as Boc, Cbz, Fmoc and the like) are coupled to amine derivatives of formula $H_2N$—A using standard amide bond forming reagents as described above. Following removal of the nitrogen protecting group from the amide derivative thus obtained, the free amine can be coupled to 5-carboxybenzimidazole derivatives through formation of a second amide linkage as described above. Following removal of any remaining protecting groups, compounds of formula 1 are obtained.

Alternatively, compounds of formula 1 according to the present invention can be prepared on a solid support as described in Scheme 3.

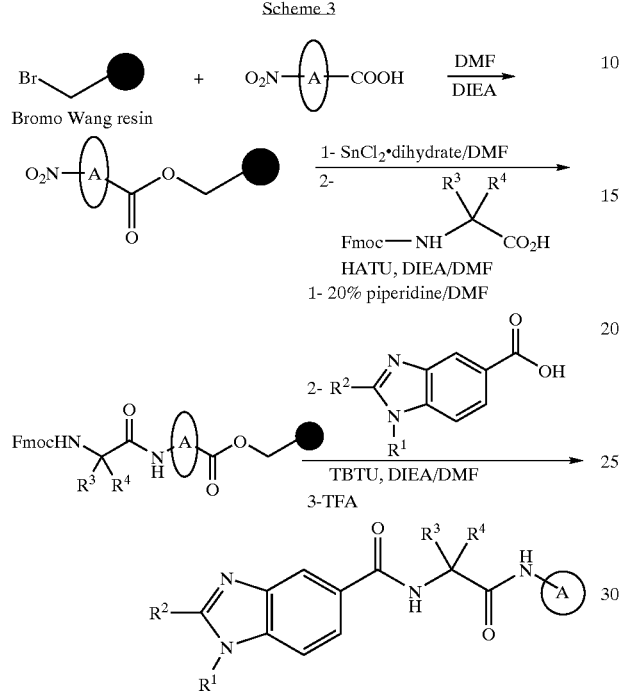

In carrying out the synthetic route illustrated in Scheme 3, derivatives of formula O$_2$N—A (where A contains a free carboxyl group) are anchored on a solid support. Such support includes bromo Wang resin, and attachment is carried out using a suitable base such as DIEA, CsF or others well known to those trained in the field of peptide synthesis on solid supports. Following reduction of the nitro group to a free amine using reducing agents such as hydrogen gas or formate salts in the presence of a catalyst (e.g. Pd metal and the like), metals in the presence of mineral acids (e.g. Fe or Zn with aqueous HCl), or metal salts (SnCl$_2$), the free amine is coupled to a suitably N-protected form of an amino acid of formula P'HNCR$^3$R$^4$COOH (P' is an amino acid N-protecting group such as Fmoc). Suitable coupling reagents include HATU, TBTU, BOP, EDAC, DCC, isobutyl chloroformate and others, in presence of an organic tertiary base such as DIEA, Et$_3$N, NMM and the like. Acid chlorides can also be used in the case of hindered amino acid derivatives. Following removal of the nitrogen-protecting group, the resulting amine is coupled to 5-carboxybenzimidazole derivatives with standard amide bond forming reagents as described previously. Compounds of formula 1 where A contains a free carboxylic acid group are obtained after cleavage from the resin under acidic conditions (TFA, MsOH, TfOH and the like).

EXAMPLES

The present invention is illustrated in further detail by the following non-limiting examples. All reactions were performed in a nitrogen or argon atmosphere. Temperatures are given in degrees Celsius. Solution percentages or ratios express a volume to volume relationship, unless stated otherwise. Flash chromatography was carried out on silica gel. Mass spectral analyses were recorded using electrospray mass spectrometry. Abbreviations or symbols used herein include:

DIEA: diisopropylethylamine;
DMAP: 4-(dimethylamino)pyridine;
DMSO: dimethylsulfoxide;
DMF: N,N-dimethylformamide;
Et: ethyl;
EtOAc: ethyl acetate;
Et$_2$O: diethyl ether;
HPLC: high performance liquid chromatography;
$^i$Pr: isopropyl
Me: methyl;
MeOH: methanol;
MeCN: acetonitrile;
Ph: phenyl;
TBE: tris-borate-EDTA;
TBTU: 2-(1H-benzotriazol-1-yl)-N,N,N',N'-tetramethyluronium tetrafluoroborate;
TFA: trifluoroacetic acid;
THF: tetrahydrofuran;
MS (ES): electrospray mass spectrometry;
PFU: plaque forming units;
DEPC: diethyl pyrocarbonate;
DTT: dithiothreitol
EDTA: ethylenediaminetetraacetate
HATU: O-(7-azabenzotriazol-1-yl)-N,N,N',N'-tetramethyluronium hexafluorophosphate
BOP: benzotriazole-1-yloxy-tris(dimethylamino) phosphonium hexafluorophosphate
BroP: bromotris(dimethylamino)-phosphonium hexafluorophosphate
EDAC: see EDC
DCC: 1,3-Dicyclohexyl carbodiimide
DCE: 1,2-dichloroethane
HOBt: 1-Hydroxybenzotriazole
ES$^+$: electrospray (positive ionization)
ES$^-$: electrospray (negative ionization)
DCM: dichloromethane
TBME: tert-butylmethyl ether
TLC: thin layer chromatography
CSA: camphorsulfonic acid
AcOH: acetic acid
EtOH: ethanol
DBU: 1,8-diazabicyclo[5.4.0]under-7-ene
BOC: tert-butyloxycarbonyl
Cbz: carbobenzyloxy carbonyl
$^i$PrOH: isopropanol
NMP: N-methylpyrrolidone
NMM: N-methylmorpholine
EDC: 1-(3-dimethylaminopropyl)-3-ethyl carbodiimide hydrochloride
RNAsin: A ribonuclease inhibitor marketed by Promega Corporation
Tris: 2-amino-2-hydroxymethyl-1,3-propanediol
UMP: uridine 5'-monophosphate
UTP: uridine 5'-triphosphate Examples 1–21 illustrate methods of synthesis of representative compounds of this invention.

Example 1
1-Cyclohexyl-2-pyridin-2-yl-1H-benzoimidazole-5-carboxylic acid

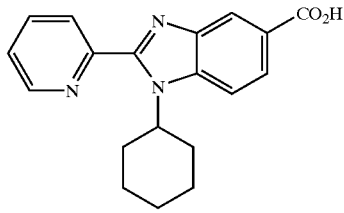

4-Chloro-3-nitrobenzoic acid, ethyl ester

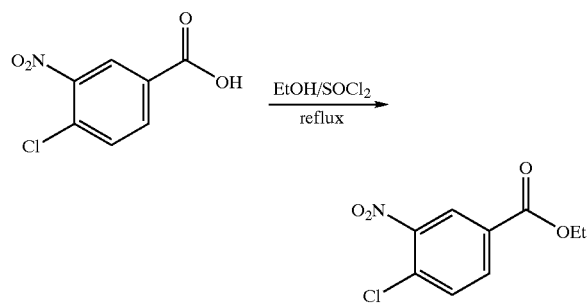

4-Chloro-3-nitrobenzoic acid (100.0 g, 0.496 mole) was suspended in EtOH (250 mL) and thionyl chloride (54 mL, 0.74 mole) was added drop-wise over 15 min. The mixture was then reflux for 2 h. After cooling to ambient temperature, volatiles were removed under reduced pressure and the residue was co-evaporated twice with EtOH (2×250 mL). The residue was crystallized from hot EtOH to give the desired ethyl ester as light yellow needles (109.8 g, 96% yield).

4-Cyclohexylamino-3-nitrobenzoic acid ethyl ester

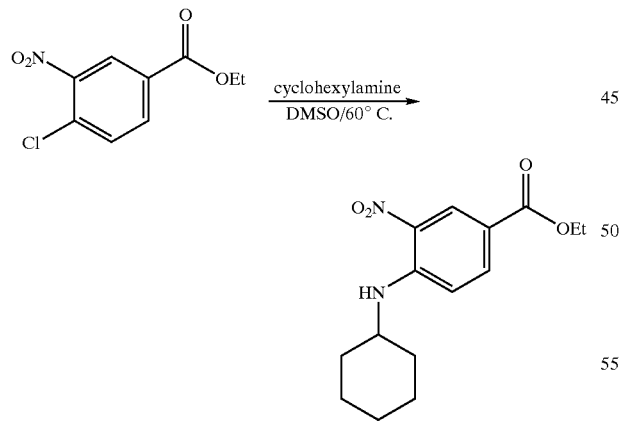

Ethyl 4-chloro-3-nitrobenzoate (20.00 g, 87 mmol) was dissolved in DMSO (50 mL) and cyclohexylamine (2.1 equiv. 21 mL, 183 mmol) was added and the mixture stirred at 60° C. for 5 h. After cooling to ambient temperature, the reaction mixture was added drop-wise with vigorous stirring to water (500 mL). After stirring for an additional 15 min, the precipitated solid was collected by filtration, washed with water and dried. The title compound (25.67 g, 100% yield) was obtained as a bright yellow solid.

3-Amino-4-cyclohexylamino benzoic acid ethyl ester

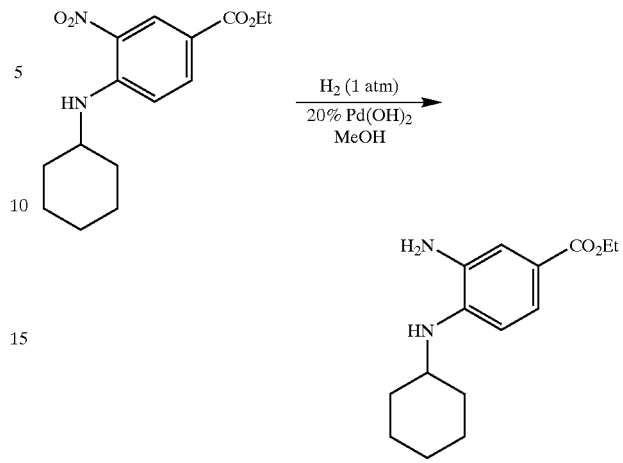

The nitro derivative from above (24.28 g, 83 mmol) was hydrogenated (1 atm $H_2$) over 20% $Pd(OH)_2$ on carbon (200 mg) in MeOH (150 mL) for 3 days. The catalyst was removed by filtration and volatiles removed under reduced pressure to give the title diamine (21.72 g, 100% yield) as a dark purple solid.

1-Cyclohexyl-2-pyridin-2-yl-1H-benzoimidazole-5-carboxylic acid

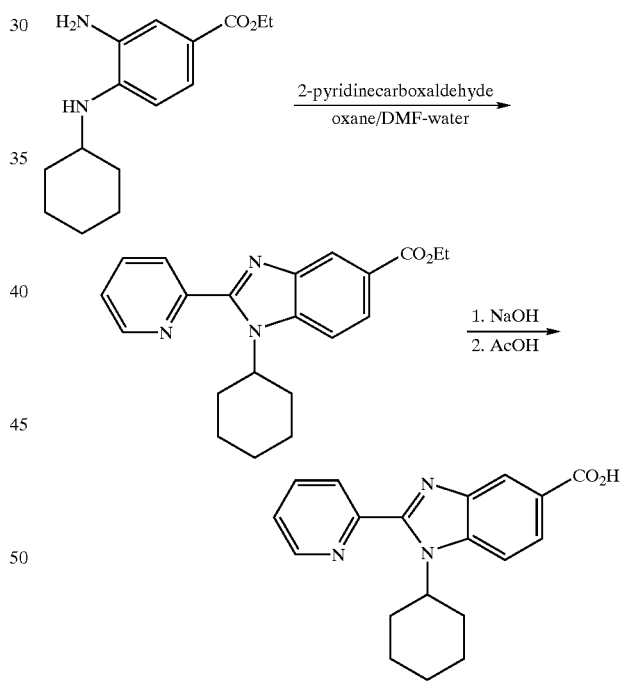

The diamine from above (3.20 g, 12.2 mmol) was dissolved in DMF (15 mL) and water (0.5 mL). 2-Pyridine carboxaldehyde (1.45 mL, 15 mmol) was added followed by oxone® (0.65 equivalent, 8 mmol, 4.92 g). The mixture was stirred 1 h at room temperature. Water (60 mL) was added, and the pH of the reaction mixture was brought up to 9 by addition of 1 N NaOH. The brown precipitate that formed was collected by filtration, washed with water and dried. The crude benzimidazole ethyl ester was obtained in 80% yield (3.43 g).

The ester from above (2.36 g, 7.53 mmol) was dissolved in MeOH (15 mL) and 2 N NaOH (20 mmol, 10 mL) was added. The mixture was stirred at 60° C. for 2 h and then cooled to room temperature. MeOH was removed under reduced pressure and the residue acidified to pH 4 with glacial AcOH. The precipitated carboxylic acid was collected by filtration, washed with water and dried to give the free acid as a beige solid (2.20 g, 91% yield).

Example 2

1-Cyclohexyl-2-(4-{[2-({1-[4-(1-phenyl-methanoyl)-phenyl]-methanoyl}-amino)-ethylcarbamoyl]-methoxy}-phenyl)1H-benzimidazole-5-carboxylic acid

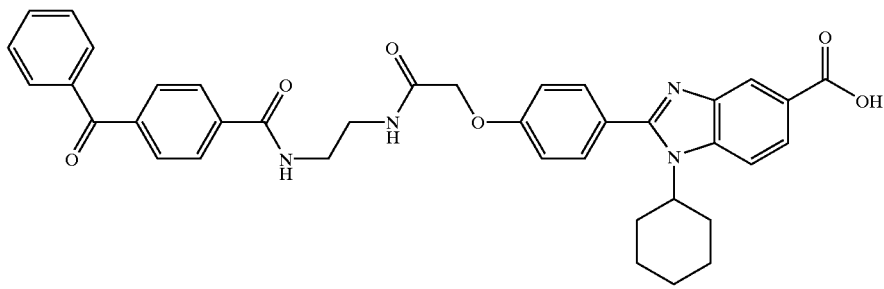

4-Formylphenoxyacetic acid (1.50 g, 8.32 mmol) in $CH_2Cl_2$ (25 ml) was stirred at RT with TBTU (2.75 g, 8.56 mmol) and DIPEA (2.8 g, 3.8 ml, 20 mmol) before addition of tert-butyl N-(2-aminoethyl)carbamate (1.38 g, 8.60 mmol). After stirring for 2.5 h, the solution was concentrated and the residue dissolved in EtOAc. The solution was successively washed with 5% water, 5% $KHSO_4$, brine and organic phase dried ($MgSO_4$). The dried solution was concentrated under reduced pressure to give a beige solid, which after purification using flash chromatography on silica gel with EtOAc gave the aldehyde as a white solid (2.0 g, 75%).

The aldehyde derivative from above (3.30 g, 10.23 mmol) and the diamine derivative of example 1 (0.052 g, 0.1 mmol) were condensed with Oxone using a procedure similar to that described in Example 1 above. After removal of the Boc group under standard acidic conditions, benzoylbenzoic acid (900 mg, 3.98 mmol) and an amide bond coupling agent, such as TBTU, were used to form the title compound after saponification, under standard conditions, of the carboxyl protecting group.

Example 3

Solid phase synthesis of 5-carboxybenzimidazole derivatives from aldehydes

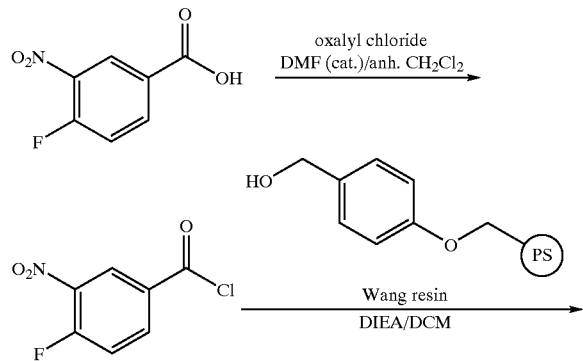

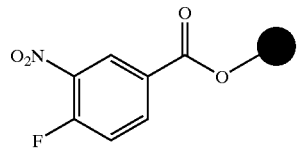

To a solution of the 4-fluoro-3-nitrobenzoic acid (0.12 mol, 22.2 g) in 100 mL of anhydrous DCM was added 10 drops of anhydrous DMF. To this solution was added drop wise over 60 min, oxalyl chloride (0.144 mol, 12.6 mL). During the addition, the solid slowly dissolved to give rise to a yellow solution. The mixture was stirred for an additional 4 h and the solvent was stripped down to give a yellow oil. This oil was distilled under vacuum (110° C., 1.5 mm Hg) to give 4-fluoro-3-nitrobenzoyl chloride as a light yellow liquid (22.0 g, 90% yield).

On a solid phase synthesizer (Advanced Chemtech ACT 90), Wang resin (Nova Biochem, loading: 1.2 mmol/g, 20 mmol, 16.7 g) was washed twice with DCM (100 mL), twice with i-PrOH (100 mL) and was dried overnight under high vacuum over $P_2O_5$. The following day, the resin was washed with anhydrous DCM (2×100 mL) and was suspended in anhydrous DCM (100 mL). To the suspension was added DIEA (30 mmol, 5.2 mL) followed by a solution of 4-fluoro-3-nitrobenzoyl chloride (22 mmol, 4.48 g) dissolved in 10 ml of anhydrous DCM. The slurry was shaken for 3 h, the solution was drained and the resin was washed twice with 100 mL-portions of anhydrous DCM. The resin was then suspended in anhydrous DCM (100 mL) and was treated with DIEA (30 mmol, 5.2 mL) followed by acetic anhydride (24 mmol, 2.3 mL). After shaking for 2 h, the solution was drained and the resin was washed successively with DCM (2×100 mL), i-PrOH (2×100 mL), DCM (2×100 mL) and finally with i-PrOH (3×100 mL). The resin was dried overnight under high vacuum.

To calculate the level of incorporation, the resin (45.9 mg) was treated with a 1:1 mixture of TFA/1,2-DCE (1.5 mL) for 1 h. The resin was filtered and was washed twice with 1,2-DCE (1.5 mL). The filtrates were combined and concentrated under vacuum. The residue was lyophilized from $MeCN/H_2O$ to give 4-fluoro-3-nitro benzoic acid as a yellow solid (6.3 mg, 0.033 mmol). Based on recovered compound, the loading was calculated to be 0.74 mmol/g.

The following steps were performed on a solid-phase synthesizer (ACT 496 from Advanced Chemtech), using the 96-well reaction block:

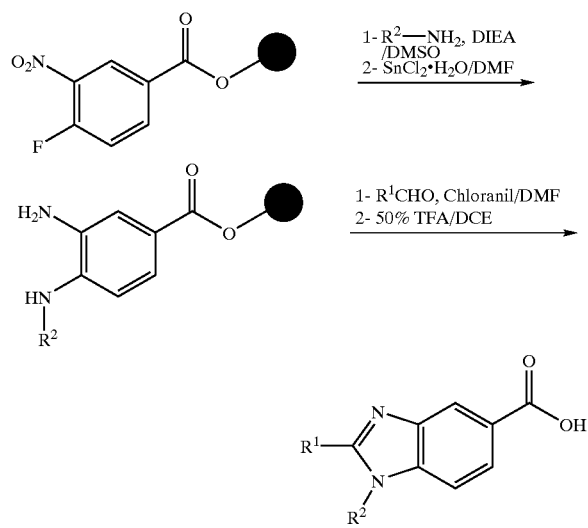

Example 4

Solid phase synthesis of 5-carboxybenzimidazole derivatives from carboxylic acids

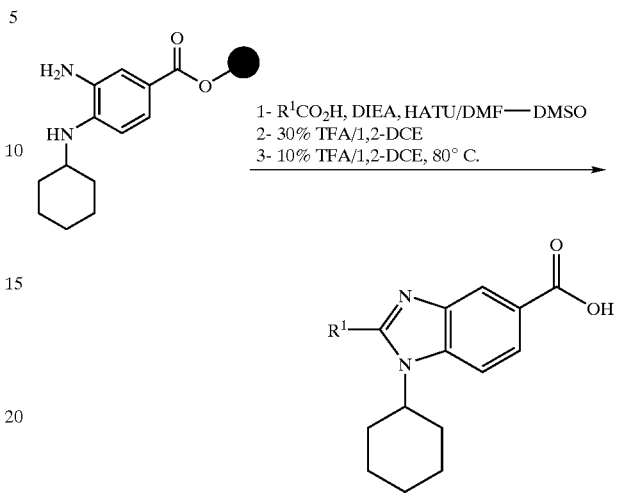

Amine Addition

Each well was filled with the benzoic acid resin from above (0.03 mmol, 40 mg) and was washed with DMF (3×1.2 mL) and DMSO (2×1.2 mL). To each well was added DMSO (530 µL), a 1 M solution in DMSO of the amine $R^2$-$NH_2$ (600 µL, 0.6 mmol) and DIEA (0.4 mmol, 70 µL). The resins were shaken for 15 h at room temperature and the solvent was drained. The resins were washed successfully with 1.2-mL portions of DMF (3×), MeOH (3×), and DMF (4×).

Reduction of the Nitro Group

The resins were then suspended in DMF (600 µL) and were shaken with a 1 M DMF solution of $SnCl_2·2H_2O$ (600 µL, 0.6 mmol) for 25 h. The solvent was drained, the resins were washed successively with 1.2-mL portions of 1:1 DMF-$H_2O$ (4×), DMF (4×), MeOH (4×) and NMP (4×).

Formation of the Benzimidazole Ring

Each resin was suspended in DMF (200 µL) and a 1 M solution of the aldehyde in DMF was added (0.20 mmol, 200 µL), followed by a 0.25 M solution of chloranil in NMP (0.20 mmol, 800 µL). The resins were shaken for 18 h, the liquid was drained and the resins were washed successively with 1.2-mL portions of NMP (3×), 1 M DIEA/NMP (2×), NMP (3×), MeOH (3×) and DCM (4×). The reaction block was placed in a vacuum chamber for 30 min in order to dry the resin.

Cleavage from the Resin

In each well was added 1.0 mL of a 1:1 solution of TFA/1,2-DCE and the resins were shaken for 1 h. The wells were drained and the resins washed once with 1.0 mL of the cleavage solution. Volatiles were evaporated in a vacuum centrifuge to give the crude benzimidazole 5-carboxylic.

The following steps were performed on a solid-phase synthesizer (ACT 496 from Advanced Chemtech), using the 96-well reaction block.

The starting diamine resin was prepared as described in example 3. Each well was filled with resin (0.0203 mmol, 35 mg) and was washed with DMF (3×1.2 mL). To each well was added a 0.5 M solution of DIEA in DMF (200 µL, 0.1 mmol), a 0.2 M solution of the acid $R_1$-$CO_2H$ in DMSO (500 µL, 0.1 mmol) and a 0.2 M solution of HATU in DMF (500 µL, 0.1 mmol). The resins were shaken for 6 h at room temperature and the solvent was drained. The coupling was repeated for another 6 h with fresh reagent. The resins were washed successfully with 1.2-mL portions of DMF (3×), MeOH (3×), and DCM (3×).

Cleavage from the Resin

In each well was added 1.0 mL of a 30% solution of TFA/1,2-DCE and the resins were shaken for 1.5 h. The wells were drained and the resins washed once with 2 mL of 1,2-DCE. The resulting filtrates containing 10% TFA in 1,2-DCE was heated at 80° C. for 13 h. The volatiles were removed under vacuum and the residue was lyophilized from MeCN/$H_2O$ to give the crude benzimidazole 5-carboxylic acid derivatives.

Example 5

3-Cyclohexyl-2-pyridin-2-yl-3H-imidazo[4,5-b]pyridine-6-carboxylic acid

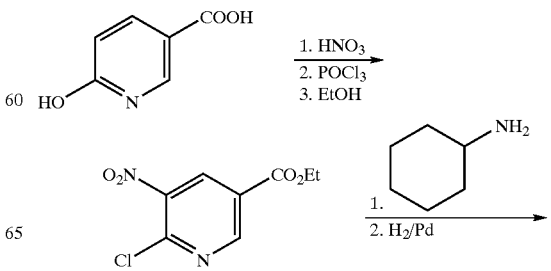

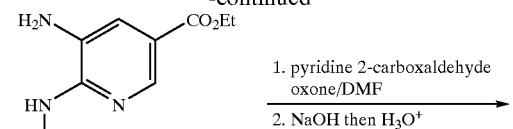

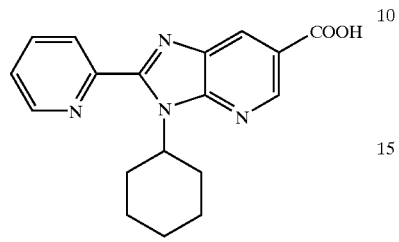

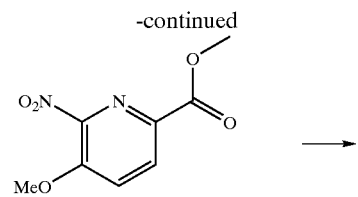

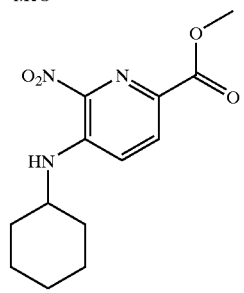

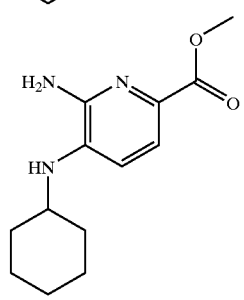

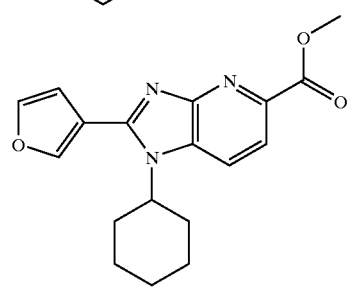

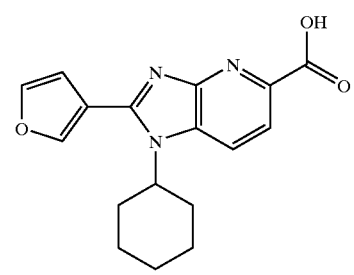

Ethyl 5-amino-6-cyclohexylaminonicotinate

Ethyl 6-chloro-5-nitronicotinate (1.00 g, 4.33 mmol) prepared according to A. H. Berrie et al. (J. Chem. Soc. 1951, 2590) was dissolved in DMSO (2 mL) and cyclohexylamine (0.54 g, 5.4 mmol) was added. The mixture was stirred for 1 h at room temperature, diluted with water and the yellow precipitate collected by filtration. The product was washed with water and dried (0.95 g, 74% yield).

The nitro derivative from above (0.68 g, 2.32 mmol) was hydrogenated (1 atm $H_2$) in EtOAc (30 mL) over 5% palladium on charcoal (100 mg). After 2 h, the reaction (complete by HPLC) was filtered and concentrated under reduced pressure to give the title diamine (0.58 g, 94% yield).

3-Cyclohexyl-2-pyridin-2-yl-3H-imidazo[4,5-b]pyridine-6-carboxylic acid

The diamine from above (0.58 g, 2.2 mmol) and 2-pyridine carboxaldehyde (0.252 g, 2.4 mmol) were dissolved in a mixture of DMF (2 mL) and water (0.1 mL). Oxone® (1.24 g, 2 mmol) was added and the mixture stirred for 2 h at room temperature. The reaction was diluted with 5% aqueous $NaHCO_3$ and extracted with DCM. The extract was washed with water and brine, dried ($MgSO_4$) and concentrated to a brown oil.

The crude ester was dissolved in MeOH (30 mL) and KOH (300 mg) was added. The mixture was refluxed for 2 h, cooled and concentrated under reduced pressure. The residue was dissolved in water (20 mL) and the solution acidified with 4 N HCl until complete precipitation of the product as a purple solid. The crude product was collected, washed with water, dried, and further purified by preparative HPLC.

Example 6

1-Cyclohexyl-2-furan-3-yl-1H-imidazo[4,5-b]pyridine-5-carboxylic acid

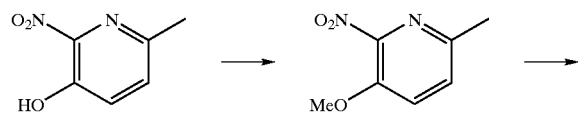

3-Methoxy-6-methyl-2-nitro-pyridine

A solution of 3-hydroxy-6-methyl-2-nitropyridine (4.00 g, 26 mmol) in MeOH—DCM (30 mL, 2:1 ratio) was treated with diazomethane in $Et_2O$ until all starting material was converted to 3-methoxy-6-methyl-2-nitropyridine (TLC). The solution was concentrated to dryness to give the desired product as a yellow solid (4.25 g, >98% yield).

5-Methoxy-6-nitro-pyridine-2-carboxylic acid methyl ester

A solution of 3-methoxy-6-methyl-2-nitro-pyridine (2.25 g, 13.4 mmol) in $H_2O$ containing $MgSO_4$ (5.24 g, 43.7 mmol) was heated to reflux. A solution of $KMnO_4$ (5.72 g, 36.2 mmol) was added slowly over a period of 1 h and reflux was maintained for an additional 5 h. The reaction mixture was cooled to room temperature and concentrated ammonia was added (6 mL). The brown solid was filtered and washed twice with water. The filtrate was concentrated and the new precipitate formed, composed mostly of starting material, was removed by filtration. The filtrate was acidified and extracted twice with EtOAc. The combined organic layers were washed with brine and dried over anhydrous MgSO$_4$, filtered and concentrated. The residue was taken up in MeOH—DCM (40 mL, 1:1 ratio) and a solution of diazomethane in Et$_2$O was added until a persisting yellow color was observed. The solution was then concentrated to dryness and purified by flash column chromatography, using a gradient of hexane/EtOAc from 6/4 to 4/6 as the eluent, to give 5-methoxy-6-nitro-pyridine-2-carboxylic acid methyl ester (585 mg, 20% yield).

5-Cyclohexylamino-6-nitro-pyridine-2-carboxylic acid methyl ester

A solution of 5-methoxy-6-nitro-pyridine-2-carboxylic acid methyl ester (0.585 g, 2.75 mmol) and cyclohexylamine (0.636 mL, 5.51 mmol) in DMF (8 mL) was heated at 70° C. for 20 h. The mixture was poured on brine (50 mL) while mixing vigorously. The solid formed was filtered, washed with water and then dissolved in EtOAc. The solution was washed with water, saturated NaHCO$_3$ and brine, dried over anhydrous MgSO$_4$, filtered and concentrated to give 5-cyclohexylamino-6-nitro-pyridine-2-carboxylic acid methyl ester as a brown oil (0.558 g) which was used in the subsequent step without purification.

6-Amino-5-cyclohexylamino-pyridine-2-carboxylic acid methyl ester

The crude 5-cyclohexyl-6-nitro-pyridine-2-carboxylic acid methyl ester from above (0.530 g, 1.90 mmol) was stirred in EtOH (10 mL) and 10% Pd/C (50 mg), under 1 atm of H$_2$ gas at room temperature for 3 days. The suspension was filtered through a pad of celite and concentrated to dryness. The product was purified by flash column chromatography, using a gradient from 60% hexane in EtOAc to 100% EtOAc as the eluent, to give 6-amino-5-cyclohexylamino-pyridine-2-carboxylic acid methyl ester (0.210 g, 30% yield).

1-Cyclohexyl-2-furan -3-yl-1H-imidazo[4,5-b]pyridine-5-carboxylic acid methyl ester To a solution of the methyl ester from above (0.100 g, 0.40 mmol) in DMF (3 mL) and H$_2$O (0.300 mL), oxone® (0.813 g, 1.32 mmol) and 3-furaldehyde (0.138 g, 1.32 mmol) were added. The reaction mixture was stirred at room temperature for 5 h and then stored at 5° C. for 3 days. The mixture was diluted with EtOAc and washed twice with water, twice with saturated NaHCO$_3$ and once with brine. The organic layer was then dried over MgSO$_4$, filtered and concentrated to give an oil that was purified by flash chromatography, using EtOAc as eluent, to give 1-cyclohexyl-2-furan-3-yl-1H-imidazo[4,5-b]pyridine-5-carboxylic acid methyl ester (0.058 g, 44% yield).

1-Cyclohexyl-2-furan-3-yl-1H-imidazo[4,5-b]pyridine-5-carboxylic acid

The ester from above (0.058 g, 0.178 mmol) was dissolved in MeOH (2 mL) and aqueous LiOH (0.700 mL, 1 M) was added. The solution was stirred at room temperature for 2 h and then purified by C$_{18}$ reversed phase preparative HPLC to give the title compound.

Example 7

1-Cyclohexyl-2-furan-3-yl-4-methyl-1H-benzimidazole-5-carboxylic acid

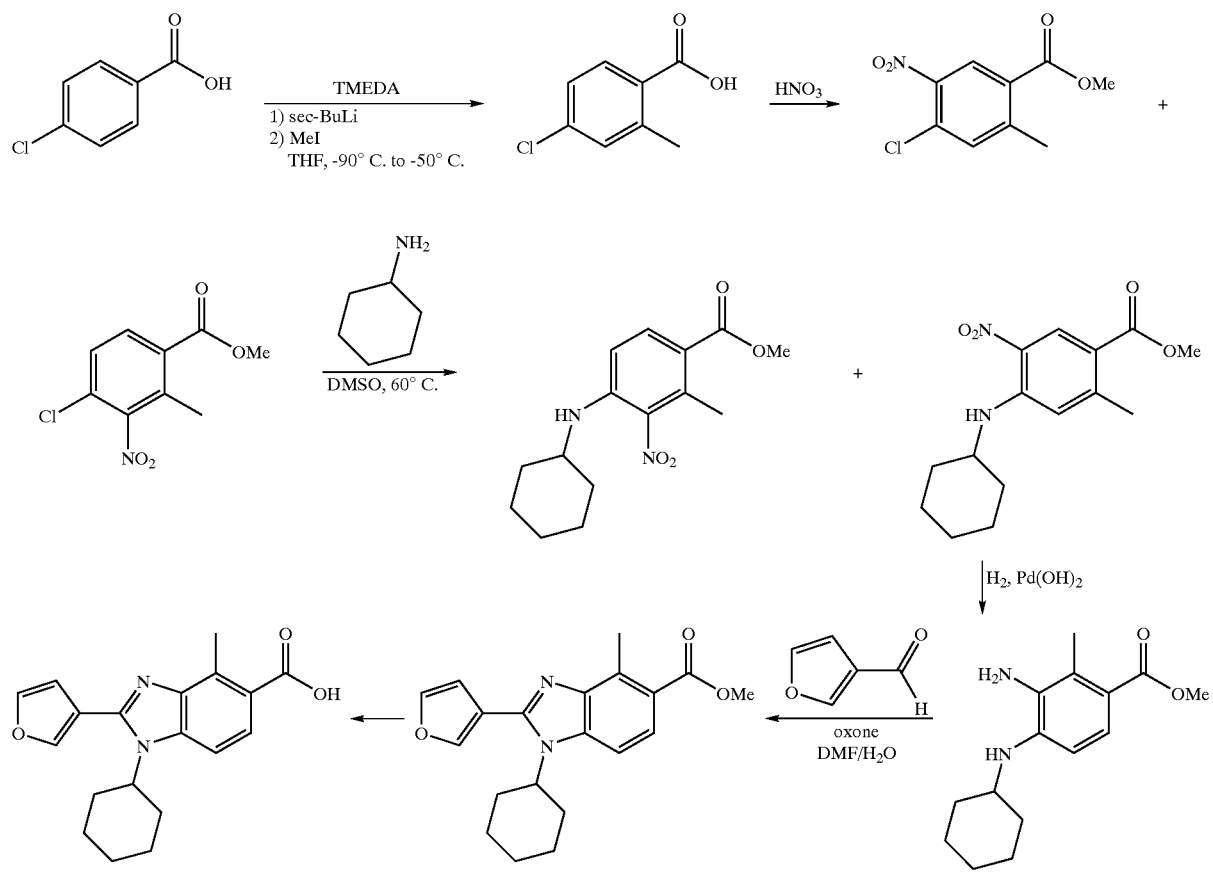

4-Chloro-2-methylbenzoic

In a dry round-bottomed flask (3 L) equipped with a mechanical stirrer under N$_2$, anhydrous N,N,N',N'-tetramethylethylenediamine (TMEDA, 99.7 mL, 660 mmol, 2.2 eq.) and anhydrous THF (600 mL) were added and the mixture was cooled to −90° C. in a bath of liquid N$_2$/EtOH. Freshly titrated sec-BuLi (550 mL, 1.2M in cyclohexane, 660 mmol., 2.2 eq.) was added slowly via cannula as to maintain the temperature at −50° C. The solution was cooled to −90° C. and 4-chlorobenzoic acid (47.0 g in 400 mL anhydrous THF, 300 mmol) was added slowly via cannula, while stirring carefully to maintain the temperature at −90° C. The reaction mixture was stirred at −90° C. for 1 h before allowed to warm-up to −80° C. and CH$_3$I (80 mL, 1.28 moles) was added very slowly. The reaction mixture was stirred for 10 min at −80° C., then quenched slowly with H$_2$O (600 mL) and allowed to warm-up to room temperature. The aqueous layer was separated, washed with Et$_2$O (2×500 mL) and then acidified with HCl (2.5 N, 600 mL) while cooling in an ice bath; cooling was continued for 16 h at 4° C. to allow crystallization of the desired product. The crude product was dried under vacuum and over anhydrous P$_2$O$_5$ and then re-crystallized from hot toluene (700 mL) to obtain pure 4-chloro-2-methylbenzoic acid (40 g, 78% yield).

Mixture of 4-chloro-2-methyl-5-nitrobenzoic acid methyl ester and 4-chloro-2-methyl-3-nitrobenzoic acid methyl ester These compounds were prepared using a modification of the procedure reported by M. Baumgarth et al. (*J. Med. Chem.* 1997, 40, 2017–2034). 4-Chloro-2-methylbenzoic acid (6 g) was added to fuming HNO$_3$ (100%, 36 g) in small portions over a period of 20 min, at 10° C., while stirring vigorously. The reaction mixture was stirred vigorously for a period of 1 h and the temperature allowed to warm-up to 20° C. The reaction mixture was then poured onto ice (100 g) and the yellow precipitate formed was collected, washed with H$_2$O, dissolved in EtOAc (25 mL) and the solution was dried over Na$_2$CO$_3$ and filtered. After concentration of the remaining mother liquor to ½ of the original volume, more precipitate was formed, however, the solid formed was always a mixture of 4-chloro-2-methyl-5-nitrobenzoic acid and 4-chloro-2-methyl-3-nitrobenzoic acid. Thus, all of the solid material formed was collected by filtration (~6.5 g), stirred in MeOH/HCl at 0° C. for 1 h to form a mixture of methyl esters. This mixture was used in the following step without further purification.

4-Cyclohexylamino-2-methyl-5-nitrobenzoic acid methyl ester and 4-cyclohexylamino-2-methyl-3-nitrobenzoic acid methyl ester The mixture of esters from above (1.1 g, 4.8 mmol) and cyclohexylamine (1.7 mL, 14.4 mmol) in DMSO (2 mL) were stirred at 60° C. for 16 h. The reaction mixture was then cooled and poured onto ice (~5 g) and mixed vigorously to allow the formation of a precipitate. The solid material was filtered, washed with H$_2$O and dissolved in EtOAc. The solution was washed with H$_2$O and brine, dried over anhydrous MgSO$_4$ and evaporated to an oil containing the desired products. The oil was triturated with hexane (~5 mL) to allow precipitation of relatively pure 4-cyclohexylamino-2-methyl-5-nitrobenzoic acid methyl ester (600 mg), whereas the mother liquor contained mostly 4-cyclohexylamino-2-methyl-3-nitrobenzoic acid methyl ester (600 mg).

3-Amino-4-cyclohexylamino-2-methylbenzoic acid methyl ester

4-Cyclohexylamino-2-methyl-3-nitrobenzoic acid methyl ester (150 mg) was dissolved in THF/MeOH (30 mL, 1:2 ratio) and stirred in the presence of H$_2$ (1 atm) and a catalytic amount of Pd(OH)$_2$ (20 mg) at room temperature for 14 h. The reaction mixture was then filtered, evaporated to dryness and purified by flash column chromatography, using 25% EtOAc in hexane with 0.2% NH$_4$OH as the eluent, to give the pure aniline (106 mg).

1-Cyclohexyl-2-furan-3-yl-4-methyl-1H-benzimidazole-5-carboxylic acid

To a solution of the diamine from above (500 mg, 1.9 mmol) in DMF (3 mL) and H$_2$O (0.15 mL), 3-furaldehyde (0.22 mL, 2.5 mmol) and oxone® (1.29 g, 2.1 mmol) were added and the reaction mixture was stirred at room temperature for 1 h. Subsequently, H$_2$O (60 mL) was added and the pH was adjusted to 8 with aqueous NaHCO$_3$. The reaction mixture was then extracted with DCM, the organic layer was washed with brine, dried over anhydrous Na$_2$SO$_4$ and evaporated to dryness. The desired benzimidazole methyl ester (446 mg) was obtained pure after column chromatography, using 25% EtOAc in hexane.

Hydrolysis of the methyl ester was achieved with an aqueous solution of NaOH (1.0 N, 0.66 mL, 6.6 mmol) in MeOH/THF (10 mL, 1:1 ratio) at 60° C. for 1.5 h. The reaction mixture was then cooled to room temperature, the pH was adjusted to 4 with AcOH and the organic solvents were evaporated. The remaining aqueous mixture was extracted with DCM (3×15 mL) and the combined organic layers were washed with H$_2$O, dried over anhydrous Na$_2$SO$_4$ and evaporated to dryness to give the desired title compound of example 7,1-cyclohexyl-2-furan-3-yl-4-methyl-1H-benzimidazole-5-carboxylic acid (392 mg, 92% yield).

Example 8

1-Cyclohexyl-2-furan-3-yl-6-methyl-1H-benzimidazole-5-carboxylic acid

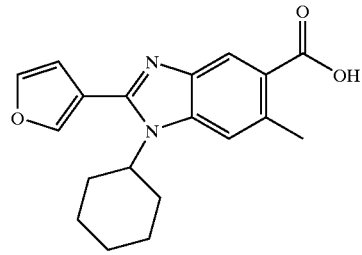

1-Cyclohexyl-2-furan-3-yl-6-methyl-1H-benzimidazole-5-carboxylic acid was prepared from 4-cyclohexylamino-2-methyl-5-nitrobenzoic acid methyl ester as described for the 4-methyl derivative in Example 7.

Example 9

General procedure for coupling amino acid methyl ester hydrochlorides to 5-carboxybenzimidazoles and deprotection of the ester functionality

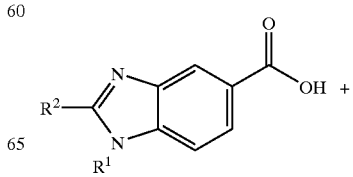

-continued

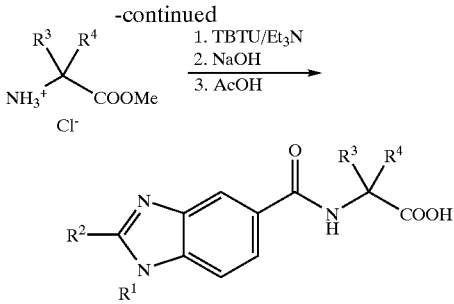

5-Carboxybenzimidazole derivatives were coupled to amino ester hydrochlorides under standard amide bond forming conditions (TBTU or HATU and base). The resulting amide esters were then saponified using a metal hydroxide and the desired free carboxylic acid isolated following acidification of the carboxylate salt with AcOH. The procedure is exemplified as follows:

2-{[1-(1-Cyclohexyl-2-furan-3-yl-1H-benzoimidazol-5-yl)-methanoyl]-amino}-2-methyl-propionic acid

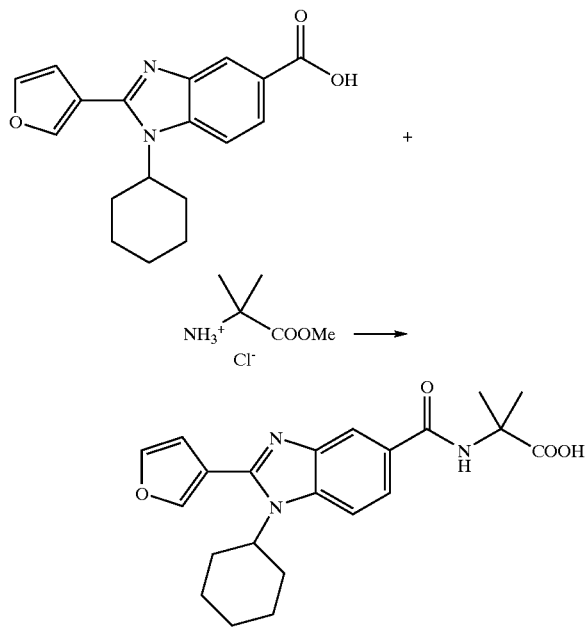

The 5-carboxybenzimidazole derivative (0.125 g, 0.40 mmol) and TBTU (0.154 g, 0.48 mmol) were dissolved in DMSO (1 mL) and Et₃N (280 μL, 2 mmol) was added followed by methyl 2-aminoisobutyrate hydrochloride (0.074 g, 0.48 mmol). The mixture was stirred for 18 h at room temperature or till complete as judged by reversed-phase HPLC analysis. 5N NaOH (1.2 mL, 15 equivalents) was added to the reaction mixture that was stirred for 4 h at room temperature. The reaction mixture was added drop wise with vigorous stirring to a solution of ACOH (1.5 mL) in water (15 mL). The precipitated solid was collected by filtration, washed with water and dried in vacuo over P₂O₅ giving the title compound (0.129 g).

Example 10

General procedure for the preparation of aromatic amide derivatives from α-monosubstituted N-Boc-amino acids ($R^4$=H in Scheme 1)

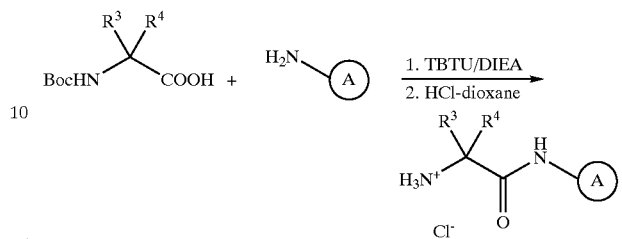

N-Boc protected α-monosubstituted amino acids were coupled to aromatic amine derivatives using standard amide bond coupling reagents. The N-Boc protecting group was then cleaved under acidic conditions and the amine derivatives were isolated as hydrochloride salts. The following procedure for coupling N-Boc-D-alanine to ethyl 4-aminocinnamate is representative:

(R)-1-[4-((E)-2-Ethoxycarbonyl-vinyl)-phenylcarbamoyl]-ethyl-ammonium chloride

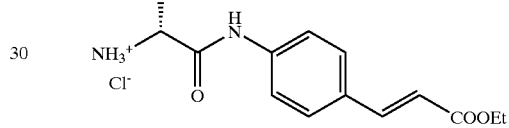

N-Boc-D-alanine (0.284 g, 1.5 mmol) was dissolved in DMSO (2 mL) and DIEA (1.04 mL, 6 mmol, 4 equivalents) was added. Ethyl 4-aminocinnamate (0.287 g, 1.5 mmol) was added followed by TBTU (0.578 g, 1.80 mmol) and the mixture was stirred for 24 h at room temperature. The reaction mixture was diluted with EtOAc (75 mL) and the solution washed with water (40 mL), 1N NaOH (3×25 mL), 1M KHSO₄ (2×25 mL) and 5% NaHCO₃ (25 mL). The extract was dried (MgSO₄) and concentrated to give the desired N-Boc-protected anilide as a yellow solid (0.411 g). The material from above was stirred for 1 h with 4N HCl in dioxane (10 mL). Removal of volatiles under reduced pressure and trituration of the residue with TBME gave the title hydrochloride salt as a brown solid.

Example 11

4-(4-Amino-phenyl)-thiazole-2-carboxylic acid ethyl ester

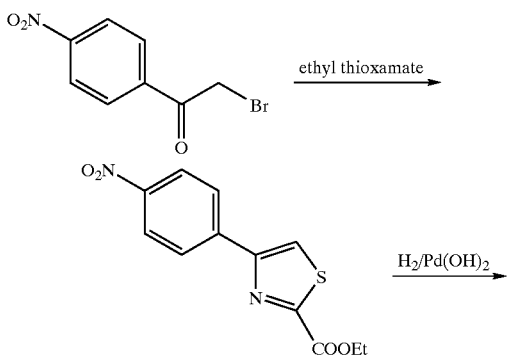

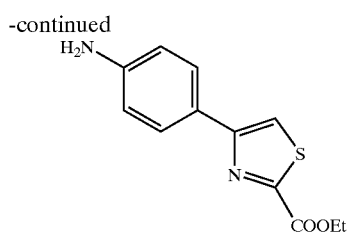

4'-Nitro-2-bromoacetophenone (6.100 g, 25 mmol) and ethyl thioxamate (3.460 g, 26 mmol) were dissolved in MeOH (20 mL) and the solution was refluxed for 1 h. After cooling to room temperature, the precipitated solid was collected by filtration, washed with cold MeOH and dried under vacuum (5.15 g, 75% yield).

A suspension of the nitroester from above (2.50 g, 8.98 mmol) and 20% Pd(OH)$_2$ on carbon (200 mg) in 2:1 EtOH—THF (60 mL) was stirred for 3 h under 1 atm of hydrogen gas. The suspension was filtered to remove the catalyst and volatiles removed under reduced pressure to give the title compound as a reddish foam (2.05 g, 92% yield).

Example 12

4-(4-Ethoxycarbonyl-thiazol-2-yl)-phenyl-ammonium chloride

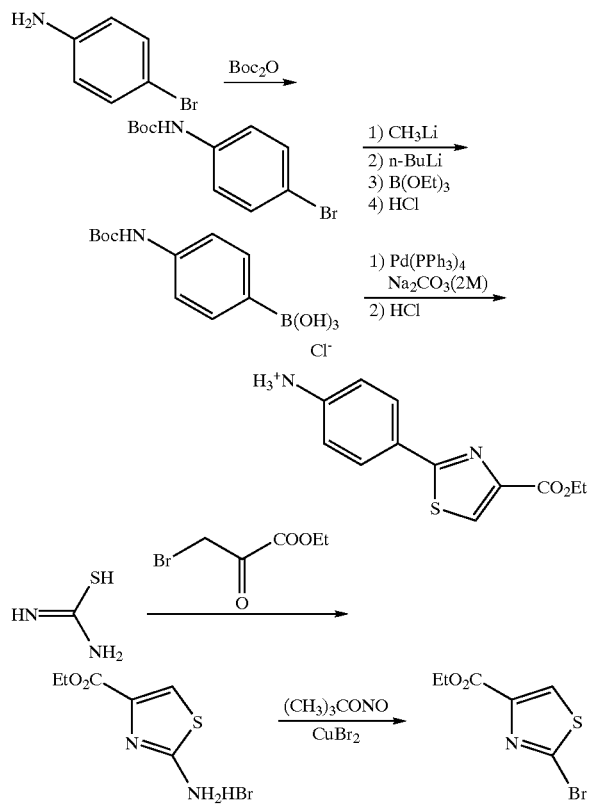

p-Bromoaniline (13.0 g, 76 mmol) and Boc$_2$O (19.8 g, 91 mmol) were dissolved in toluene (380 mL) and stirred at 70° C. for 15 h. The reaction mixture was cooled to RT, evaporated to dryness, re-dissolved in EtOAc and washed with 0.1M HCl and brine. The organic solution was dried over anhydrous MgSO$_4$, evaporated to dryness and purified by flash column chromatography, using 5% to 10% EtOAc in hexane as the eluent, to obtain the Boc-protected aniline (23 g). The Boc-protected bromoaniline (10.7 g, 39.2 mmol) was dissolved in anhydrous THF (75 mL) in a flask equipped with an overhead stirrer. The solution was cooled to 0° C. and MeLi (1.2 M in Et$_2$O, 33 mL, 39.2 mmol) was added drop wise while maintaining the internal temperature below 7° C. The reaction mixture was stirred at 0° C. for 15 min and then cooled to −78° C. before n-BuLi (2.4 M in hexane, 17 mL, 39.2 mmol) was added drop wise, maintaining the internal temperature below −70° C.). The reaction mixture was stirred at −78° C. for 1 h, B(OEt)$_3$ (17 mL, 98 mmol) was added drop wise (internal temperature<−65° C.) and stirring was continued for 45 min at −78° C. and at 0.° C. for 1 h. The reaction mixture was then treated with 5% aqueous HCl (~100 mL, to pH ~1) for 15 min and NaCl(s) was added to saturate the aqueous layer. The aqueous layer was extracted with 0.5 M NaOH (4×100 mL) and the combined aqueous layers were acidified with 5% HCl (150 mL, to pH ~1) and extracted with Et$_2$O (3×200 mL). The combined organic layers were dried over anhydrous MgSO$_4$, filtered and concentrated to give the N-Boc carbamate of 4-aminophenylboronic acid as a solid (7.5 g).

Thiourea (7.60 g, 100 mmol) and ethyl bromopyruvate (12.6 mL, 100 mmol) were mixed and heated to 100° C. for 45 min. After cooling of the reaction mixture, the solid obtained was triturated with acetone, filtered and recrystallized from EtOH to obtain the desired aminothiazole product (10.6 g, 40 mmol). The aminothiazole was then added slowly (over a period of 20 min) to a solution of t-butylnitrite (6.2 g, 60 mmol) and CuBr$_2$ (10.7 g, 48 mmol) in MeCN (160 mL) at 0° C. The reaction mixture was allowed to warm-up to RT and to stirred for 2.5 h. The mixture was then added to an aqueous HCl solution (20%) and extracted with Et$_2$O (2×400 mL). The organic layer was washed with aqueous HCl (10%), dried over anhydrous MgSO$_4$ and evaporated to dryness. The desired bromothiazole product was isolated in ~85% yield (4.3 g) after flash column chromatography using 15% EtOAc in hexane as the eluent.

To a de-gassed solution of the bromothiazole product (230 mg, 0.97 mmol), the boronic acid derivative from above (230 mg, 0.97 mmol) and aqueous Na$_2$CO$_3$ (2M, 3 mL) in DME (3 mL), a catalytic amount of Pd(PPh$_3$)$_4$ (56 mg, 0.049 mmol) was added and the reaction mixture was stirred at 80° C. under argon for 20 h. The reaction mixture was then cooled to RT, diluted with EtOAc and extracted with brine, aqueous NaHCO$_3$ (2×) and brine. The organic layer was dried over anhydrous MgSO$_4$ and concentrated to dryness. The carbamate-ester product was isolated after flash column chromatography using 20% to 30% EtOAc in hexane: 180 mg. The aniline hydrochloride was isolated after removal of the Boc protecting group with 4N HCl in dioxane for 30 min.

Example 13

4-(2-Methoxycarbonyl-4-methyl-thiazol-5-yl)-phenyl-ammonium chloride

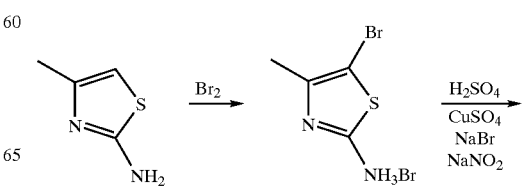

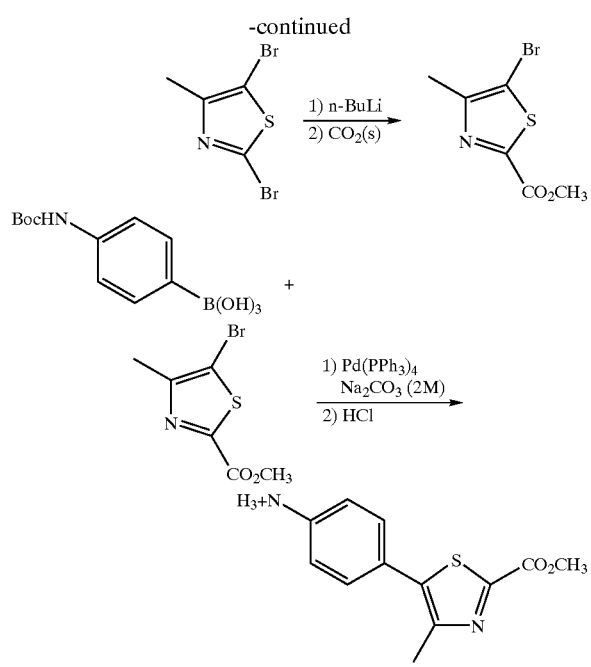

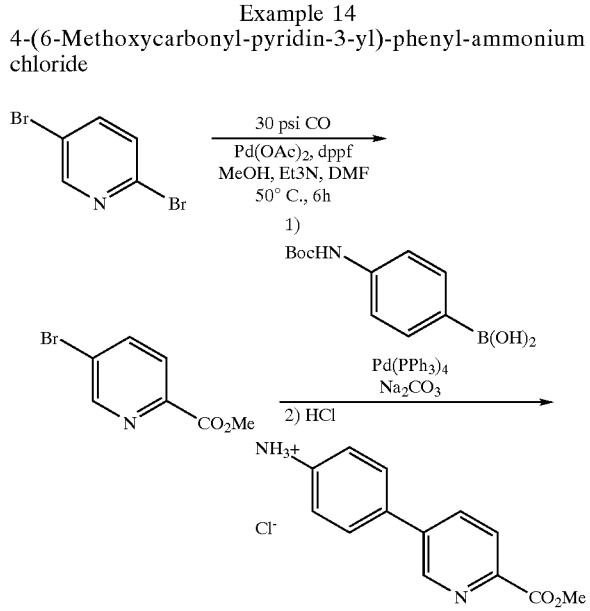

Example 14
4-(6-Methoxycarbonyl-pyridin-3-yl)-phenyl-ammonium chloride

The synthesis of the 5-bromopyridine-2-carboxylic acid methyl ester was achieved following the procedure of Chambers and Marfat (*Synth. Commun.* 1997, 27, 515). A solution of 2,5-dibromopyridine (10.0 g, 42.2 mmol), 1,1'-bis(diphenylphosphino)ferrocene (dppf, 1.4 g, 2.5 mmol), Pd(OAc)$_2$ (0.3 g, 1.3 mmol), Et$_3$N (12 mL, 84 mmol) in dry MeOH (40 mL) and dry DMF (40 mL) was deairated under a stream of CO for 10 min, then shaken in a Parr apparatus under 30 psi CO at 50° C. for 6 h. The mixture was diluted with EtOAc (600 mL) and washed with H$_2$O (2×100 mL), brine (100 mL), dried over anhydrous MgSO$_4$ and concentrated to give a solid. Flash column chromatography, using 20% EtOAc in hexane as the eluent, gave the 5-bromopyridine-2-carboxylic acid methyl ester as a white solid (5.77 g).

Cross-coupling of the 5-bromopyridine-2-carboxylic acid methyl ester with N-Boc protected aniline boronic acid (Example 12) under typical Suzuki conditions, followed by removal of the Boc protecting group with HCl (as described previously), afforded the desired compound.

To a solution of 2-amino-4-methylthiazole (7.90 g, 69 mmol) in Et$_2$O (70 mL) at 15° C., Br$_2$ was added slowly over a period of 30 min while stirring vigorously. The solid material formed was filtered and recrystallized from EtOH. The crystalline product was filtered and dried under vacuum to give the 5-bromo derivative as the HBr salt (10.3 g). This product was then dissolved in a solution of CuSO$_4$ (11.4 g) and NaBr (9.9 g) in H$_2$O (115 mL) and H$_2$SO$_4$ (5M, 360 mL) was added at 0° C. An aqueous solution of NaNO$_2$ (6.10 g in 20 mL of H$_2$O) was then added drop wise to the reaction mixture over a period of 25 min, maintaining the temperature below 3° C. The reaction mixture was stirred at 3° C. for 20 min and then at RT for 1 h. The reaction mixture was diluted with brine (280 mL) and extracted with Et$_2$O (3×300 mL). The ether layers were combined, washed with a saturated, aqueous solution of sodium thiosulfate to eliminate any unreacted Br$_2$, dried over anhydrous MgSO$_4$ and filtered through a pad of silica gel (~200 mL). The solvent was evaporated and the desired product isolated by distillation (bp=80–81° C. at 15 mm Hg).

A solution of the dibromo intermediate (500 mg, 1.94 mmol) in hexane (5 mL) was added to a cooled solution (–70° C.) of n-BuLi (870 µL of 2.2M in hexane), diluted with 10 mL of hexane. The reaction was stirred at –70° C. for 1 h and then added to CO$_2$(s). The mixture was partitioned between H$_2$O and Et$_2$O. The aqueous layer was acidified with 1N HCl (pH ~2) and extracted with EtOAc (2×), dried over anhydrous MgSO$_4$, filtered and evaporated to dryness. The residue was re-dissolved in MeOH/DCM, treated with CH$_2$N$_2$ (until the solution remained yellow) and evaporated to dryness to give the desired 5-bromo-4-methylthiazole-2-carboxylate ester as a yellow solid (230 mg). Suzuki cross-coupling of this product with the N-Boc protected 4-aminophenylboronic acid of example 12, as previously described, gave the building block 5-(4-aminophenyl)-4-methyl-thiazole-2-carboxylate methyl ester. This product was treated with 4N HCl in dioxane for 30 min to remove the Boc protecting group and obtain the desired compound.

Example 15
5-Amino-1-methyl-1H-indole-2-carboxylic acid ethyl ester

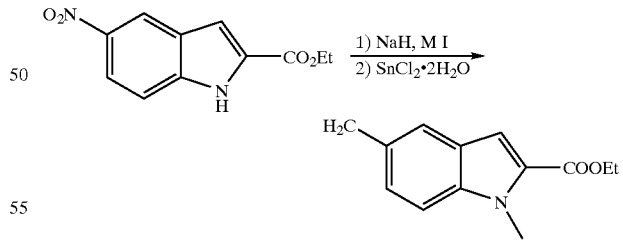

The ethyl ester of 5-nitroindole-2-carboxylic acid (0.300 g, 1.28 mmol) was dissolved in anhydrous DMF (6 mL) and NaH (0.078 g, 60%, 1.92 mmol) was added. The reaction was stirred at RT for 20 min, then MeI (160 µL, 2.56 mmol) was added and stirring was continued for 3 h. The reaction was quenched with the addition of aqueous NaHCO$_3$ (~1%) while stirring vigorously. The brown solid formed (0.096 g) was filtered and dried in air overnight.

The N-methyl nitro derivative (196 mg, 0.79 mmol) was then dissolved in DMF (4 mL), H$_2$O (400 µL) and SnCl$_2$.2H$_2$O (888 mg, 3.95 mmol) were added, and the mixture was stirred at 60° C. for 3 h. The mixture was then partitioned between 10% aqueous NaHCO$_3$ and EtOAc and stirred vigorously. The aqueous layer was re-extracted with EtOAc and the combined EtOAc layers were washed with brine, dried over anhydrous MgSO$_4$ and concentrated to dryness. The residue was purified by flash column chromatography, using 1:1 ratio EtOAc/hexane as the eluent, to obtain the pure 5-aminoindole derivative (118 mg).

N-Alkylation of 5-nitroindole-2-carboxylate with other alkylating agents (such as EtI, propargyl bromide, benzyl bromide) under the conditions described above gave the corresponding 5-amino-1-alkyl-1H-indole-2-carboxylates.

Example 16

5-{[1-(4-Amino-1-t-butoxycarbonyl-piperidin-4-yl)-methanoyl]-amino}-1-methyl-1H-indole-2-carboxylic acid ethyl ester

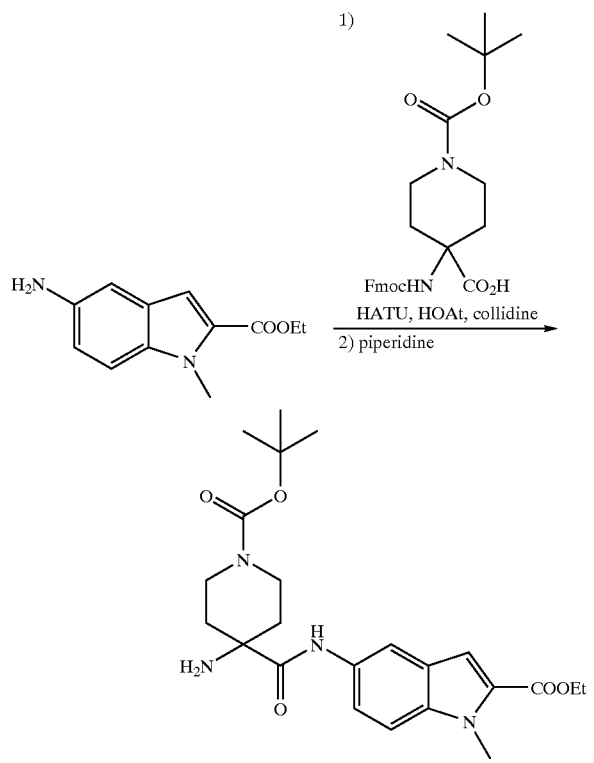

A solution of amino-indole from example 15 (70 mg, 0.32 mmol), N-Fmoc-amino-(4-N-Boc-piperidinyl)carboxylic acid (150 mg, 0.32 mmol), HATU (139 mg, 0.35 mmol), HOAt (48 mg, 0.35 mmol) and collidine (155 mg, 1.28 mmol) in DMF (2 mL) was stirred at RT for 15 h. The reaction mixture was diluted with EtOAc, washed with 1% aqueous citric acid (2×), saturated NaHCO$_3$ (2×) and brine, dried over anhydrous MgSO$_4$ and concentrated to dryness to give an orange solid (210 mg) which was used in the next reaction without purification. A solution of the crude solid (210 mg) in DMF (3 mL) and piperidine (95 mL, 0.95 mmol) was stirred at RT for 3 h. The reaction mixture was concentrated to dryness and purified by flash column chromatography, using a solvent gradient from 50% EtOAc in hexane to 100% EtOAc as the eluent, to give the desired compound as a brown solid (110 mg).

Example 17

(E)-3-[4-(2-Amino-2-methyl-propanoylamino)-phenyl]-acrylic acid ethyl ester

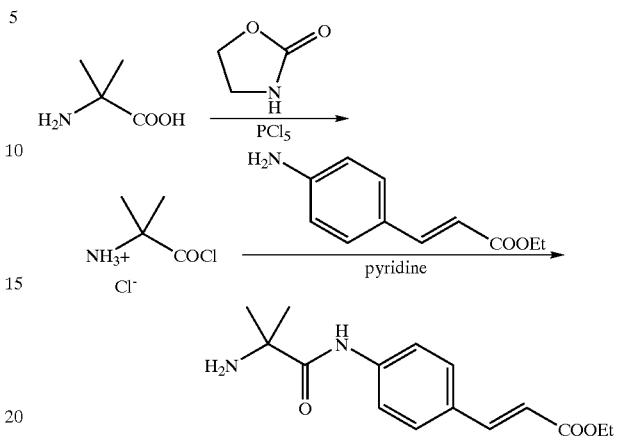

Adapting the procedure described in E. S. Uffelman et al. (*Org. Lett.* 1999, 1, 1157), 2-aminoisobutyric acid was converted to the corresponding amino acid chloride hydrochloride: 2-oxazolidinone (12.30 g, 0.141 mole) was dissolved in MeCN (150 mL) and phosphorous pentachloride (49.02 g, 0.235 mole, 1.7 equivalent) was added in one portion. The homogeneous mixture was stirred for 24 h at room temperature. 2-Aminoisobutyric acid (14.55 g, 0.141 mole) was added and the suspension was stirred for 48 h at room temperature. The desired acid chloride hydrochloride was collected by filtration, washed with MeCN and dried under vacuum.

The acid chloride (12.778 g, 80 mmol, 1.4 equivalent) was suspended in DCM (200 mL) and ethyl 4-aminocinnamate (11.045 g, 57.7 mmol, 1 equivalent) was added. Pyridine (7.01 mL, 86.6 mmol, 1.5 equivalent) was added drop wise and the mixture was stirred for 3.5 h at room temperature. The reaction was then poured into a mixture of 1N NaOH (25 mL) and saturated aqueous NaHCO$_3$ (100 mL) and extracted with EtOAc. The organic phase was washed with aqueous NaHCO$_3$, water and brine, and dried over MgSO$_4$. Removal of solvent under reduced pressure gave the title compound of as a white solid (15.96 g, 101% yield).

Example 18

(E)-3-(4-{[1-(1-Amino-cyclobutyl)-methanoyl]-amino}-phenyl)-acrylic acid ethyl ester

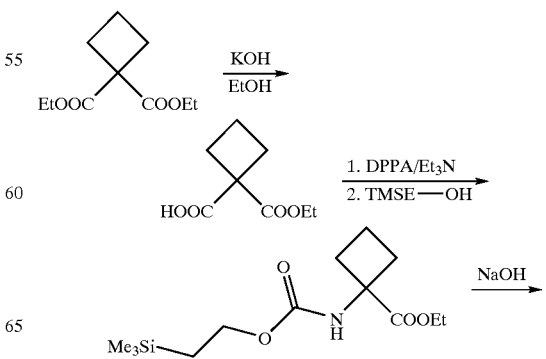

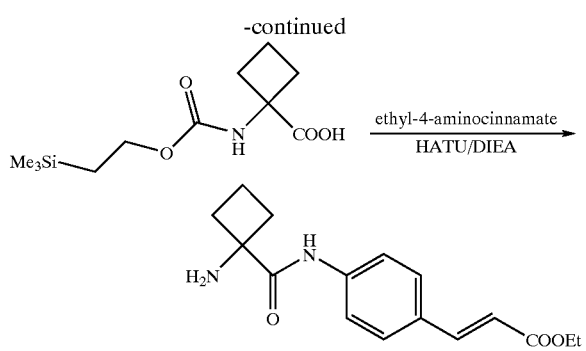

Diethyl 1,1-cyclobutanedicarboxylate (20.00 g, 100 mmol) and KOH (6.60 g, 100 mmol) were refluxed in EtOH (100 mL) for 2 h. After cooling to room temperature, volatiles were removed under reduced pressure and the residue partitioned between Et$_2$O and 4N HCl. The organic extract was washed with water and brine, and dried over MgSO$_4$. Removal of the solvent under reduced pressure gave the monoester as a clear oil (14.45 g, 84% yield).

The monoester from above (14.45 g, 84 mmol), Et$_3$N (14.1 mL, 100 mmol) and diphenylphosphoryl azide (24.05 g, 87.4 mmol) were dissolved in dry toluene (114 mL) and the mixture heated at 80° C. for 1 h and 110° C. for an additional hour. Trimethylsilylethanol (9.94 g, 100 mmol) was added in one portion and the mixture refluxed for 48 h. Toluene was then removed under reduced pressure and the residue dissolved in DCM. The solution was washed with water and brine and dried over MgSO$_4$. Concentration under reduced pressure gave a dark oil which was purified by passage through a pad of silica gel using 30% EtOAc in hexane as eluent. The desired carbamate was obtained as a clear yellow liquid (21.0 g). The carbamate from above (1.50 g, 5.22 mmol) was dissolved in THF (5 mL) and 2N NaOH (5 mL) was added. The mixture was stirred at 70° C. for 1 h. Following dilution with water, the aqueous phase was washed with Et$_2$O to remove unreacted starting material. The aqueous phase was then acidified with KHSO$_4$ and the product extracted with EtOAc. The desired free carboxylic acid was obtained as an oil (1.25 g).

The acid from above (0.519 g, 2.0 mmol) was dissolved in DCM (10 mL). DIEA (1.39 mL, 8.0 mmol, 4 equivalents) was added, followed by ethyl 4-aminocinnamate (0.573 g, 3.0 mmol, 1.5 equivalent) and HATU (1.143 g, 3.0 mmol, 1.5 equivalents). The mixture was stirred at room temperature for 3 days. The reaction was poured into TBME (100 mL) and the solution washed successively with 10% aqueous citric acid (2×25 mL) and saturated aqueous NaHCO$_3$ (25 mL), and dried over MgSO$_4$. The solvent was removed under reduced pressure and the residue stirred with TFA (10 mL) for 30 min. Volatiles were then removed under reduced pressure and the residue was co-evaporated twice with hexane. The crude product was dissolved in TBME (60 mL) and the solution washed with 1N NaOH (2×25 mL). After drying (Na$_2$SO$_4$), volatiles were removed in vacuum to give the title compound as a light brown solid (0.500 g).

Example 19
Preparation of Inhibitors on Solid Support

Referring to Scheme 3 above, the following steps were performed on a solid-phase synthesizer (ACT 496 from Advanced Chemtech), using the 96-well reaction block:

Anchoring on the Resin

Each well was filled with bromo Wang resin (0.044 mmol, 40 mg) and was washed with DMF (3×1.2 mL). To each well was added DMF (200 µL), a 1 M solution of DIEA in DMF (300 µL, 0.3 mmol), and the appropriate nitro acid derivative (0.176 mmol) dissolved in 500 µL of DMF. The resins were shaken for 15 h at room temperature and the solvent was drained. The resins were washed successively with 1.2 mL portions of DMF (3×), MeOH (3×), and DMF (3×).

Reduction of the Nitro Group and Coupling of Fmoc-amino Acids

The nitro group was reduced to the corresponding aniline using tin (II) chloride dihydrate (1.2 mL of a 0.5 M solution in DMF, 0.6 mmol) for 24 h followed by washing (3×1.2 mL) with DMF, DMF/H$_2$O, DMF, MeOH and DMF. The resin was then suspended in DMF (200 µL) and treated with a 0.5 M solution of DIEA in DMF (300 µL, 0.15 mmol), a 0.13 M solution of Fmoc-amino acid (500 µL, 0.066 mmol) and a 0.13 M solution of TBTU in DMF (500 µL, 0.066 mmol). After shaking for 5 h at 60° C., and since several reactions were not complete as indicated by the cleavage of a few resin beads, fresh reagents were added and a second coupling was done using HATU as coupling agent at room temperature for 18 h.

Coupling of the Core Benzimidazole and Cleavage from the Resin

The Fmoc group was cleaved with 20% piperidine/DMF (20 min) and after washing, the 5-carboxybenzimidazole derivative (e.g. from example 1) was coupled under standard conditions using TBTU as coupling agent (room temperature, 18 h).

Cleavage from the Resin

In each well was added 1.0 mL of a 50% solution of TFA/1,2-DCE and the resins were shaken for 1 h. The wells were drained and the resins washed once with 1 mL of the 50% TFA/1,2-DCE solution. The volatiles were removed under vacuum and the compounds were purified by semi-prep reversed phase chromatography to give compounds of formula 1.

Example 20
General procedure for coupling N-benzimidazoylamino acids to aromatic amines

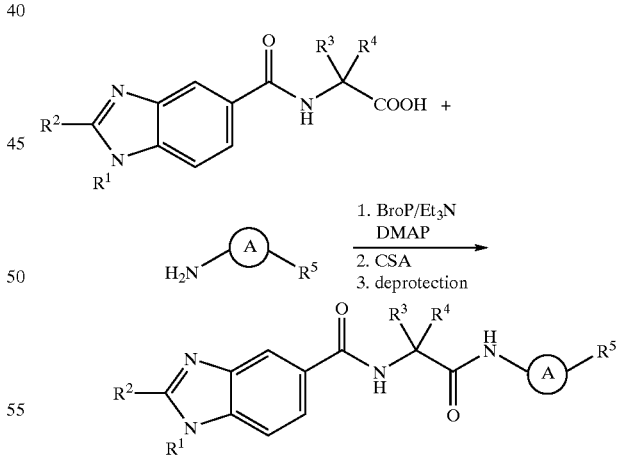

N-Benzimidazoylamino acid derivatives synthesised as described in Example 9 above, were coupled to aromatic amines using BroP/camphor-10-sulfonic acid as coupling agent as described by H. Heimgartner and P. Wipf in *Helv. Chim. Acta*, 1986, 69, 1153. Products were deprotected under standard conditions to give compounds of formula 1, which are the subject of the present invention. The following specific Example will serve to illustrate the process and is not intended to be limiting.

(E)-3-(4-{[1-(1-{[1-(1-Cyclohexyl-2-furan-3-yl-1H-benzoimidazol-5-yl)-methanoyl]-amino}-cyclopropyl)-methanoyl]-amino}-phenyl)-acrylic acid (Entry 1070)

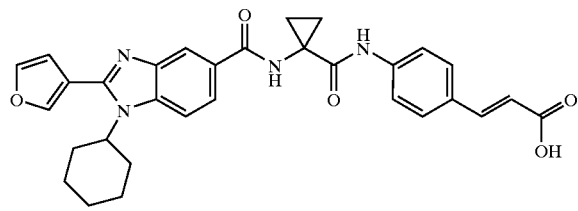

The appropriate amino acid derivative from Example 9 (0.020 g, 0.05 mmol) was dissolved in DCM (1 mL). DMAP (0.018 g, 3 equivalents), Et$_3$N (20 μL, 0.15 mmol, 3 equivalents), BroP (0.058 g, 0.15 mmol, 3 equivalent), and ethyl-4-aminocinnamate (0.029 g, 0.015 mmol, 3 equivalents) were added and the mixture stirred for 20 h at room temperature. Camphor-10-sulfonic acid (CSA; 0.046 g, 0.2 mmol, 4 equivalents) was added and the reaction mixture was stirred for an additional 24 h at room temperature.

The reaction mixture was then diluted with a 1:1 mixture of EtOAc and Et$_2$O (5 mL) and extracted with 5% NaHCO$_3$ (1 mL). The mixture was then passed through a cartridge of Extrelut® (EM Science, 0.6 g) to remove water using 1:1 EtOAc:Et$_2$O as eluent (5 mL). The organic filtrate was concentrated under reduced pressure and the residue co-evaporated with MeCN (5 mL).

The residue was then dissolved in DMSO (0.8 mL) and 2.5N NaOH (0.2 mL) was added. The mixture was stirred for 2 h at room temperature, neutralized by addition of TFA and the title compound (9 mg) isolated from the reaction mixture by preparative reversed-phase HPLC.

Example 21
General procedure for coupling of α-amino amide derivatives to 5-carboxybenzimidazole derivatives

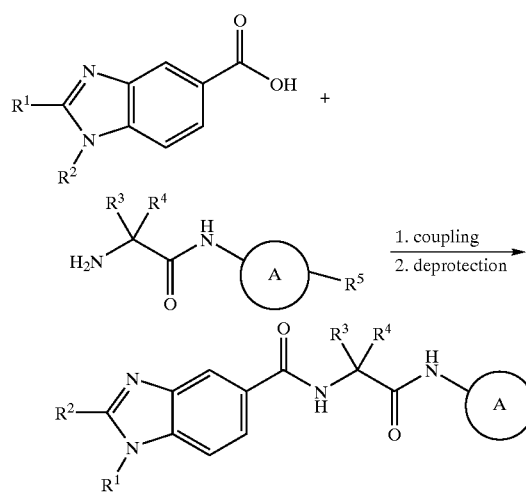

5-Carboxybenzimidazole derivatives, such as those described in Examples 1, 3 and 4, were coupled to α-amino amide derivatives, such as those described in Examples 10, 16, 17, and 18, using standard amide bond forming reagents, such as TBTU in the presence of an organic base (DIEA, Et$_3$N and the like). The resulting products were deprotected under standard conditions (if necessary) to give compounds of formula I, which are the subject of this invention. The following Example is intended to illustrate such a process and is non-limiting.

(E)-3-[4-((R)-2-{[1-(1-Cyclohexyl-2-furan-3-yl-1H-benzoimidazol-5-yl)-methanoyl]-amino}-butanoylamino)-phenyl]-acrylic acid (Entry 1075)

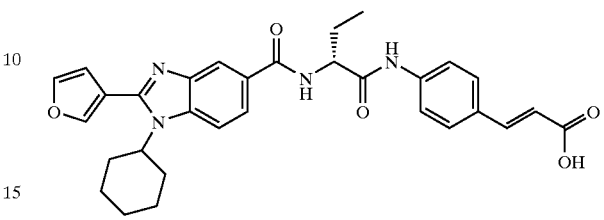

The 5-carboxybenzimidazole derivative (0.020 g, 0.064 mmol) was dissolved in DMSO (0.5 mL). TBTU (0.027 g, 0.084 mmol, 1.3 equivalent) was added followed by Et$_3$N (36 μL, 0.26 mmol, 4 equivalents). The reaction mixture was stirred for 20 min at room temperature. The amine hydrochloride prepared according to Example 10 (0.029 g, 0.096 mmol, 1.5 equivalent) was added and the mixture stirred for 1 h at room temperature.

DMSO (0.5 mL) and 2.5N NaOH (0.3 mL) were added and stirring at room temperature continued for an additional 1 h. The reaction mixture was then acidified with TFA (0.2 mL) and the title compound was isolated by preparative reversed-phase HPLC.

Example 22
Inhibition of NS5B RNA Dependent RNA Polymerase Activity

The compounds of the invention were tested for inhibitory activity against the hepatitis C virus RNA dependant polymerase (NS5B), according to the following assay:

The substrates are:

a 12 nucleotide RNA oligo-uridylate (or oligo-uridine-monophosphate) (oligo-U) primer modified with biotin at the free 5'C position;

a complementary poly-adenylate (or adenosine monophosphate) (polyA) template of heterogeneous length (1000–10000 nucleotides); and UTP-[5,6 $^3$H].

Polymerase activity is measured as the incorporation of UMP-[5,6 $^3$H] into the chain elongated from the oligo-U primer. The $^3$H-labelled reaction product is captured by SPA-beads coated with streptavidin and quantified on the TopCount.

All solutions were made from DEPC treated MilliQ water [2 ml of DEPC is added to 1 L of MilliQ water; the mixture is shaken vigorously to dissolve the DEPC, then autoclaved at 121° C. for 30 minutes].

Enzyme

The full length HCV NS5B (SEQ ID NO.1) was purified as an N-terminal hexa-histidine fusion protein from baculovirus infected insect cells. The enzyme can be stored at −20° C. in storage buffer (see below). Under these conditions, it was found to maintain activity for at least 6 months.

Substrates

The biotinylated oligo-U$_{12}$ primer, the Poly(A) template, and the UTP-[5,6 $^3$H] were dissolved in water. The solutions can be stored at −80° C.

| | |
|---|---|
| Assay buffer: | 20 mM Tris-HCl pH 7.5 |
| | 5 mM MgCl$_2$ |
| | 25 mM KCl |
| | 1 mM EDTA |
| | 1 mM DTT |
| NS5B storage buffer: | 0.1 μM NS5B |
| | 25 mM Tris-HCl pH 7.5 |
| | 300 mM NaCl |
| | 5 mM DTT |
| | 1 mM EDTA |
| | 0.1% n-Dodecyl maltoside |
| | 30% glycerol |

Test Compound Cocktail

Just prior to assay, test compounds of the invention were dissolved in assay buffer containing 15% DMSO.

Substrate Cocktail

Just prior to assay, the substrates were mixed in assay buffer to the following concentrations:

| Component | Concentration in substrate cocktail | Final Concentration in assay |
|---|---|---|
| RNAsin ™ | 0.5 U/μL | 1.67 U/μL |
| Biotin-oligo-U$_{12}$ primer | 3 ng/μL | 1 ng/μL |
| PolyA template | 30 ng/μL | 10 ng/μL |
| UTP-[5,6-$^3$H] 35 Ci/mmol | 0.025 μCi/μL | 0.0083 μCi/μL |
| | | 0.25 μM |
| UTP | 2.25 μM | 0.75 μM |

Enzyme Cocktail

Just prior to assay, the RNA polymerase (NS5B) cocktail was prepared in assay buffer to the following specifications:

| Component | Concentration in cocktail |
|---|---|
| Tris-HCl at pH 7.5 | 20 mM |
| MgCl$_2$ | 5 mM |
| KCl | 25 mM |
| EDTA | 1 mM |
| DTT | 1 mM |
| n-Dodecyl maltoside | 1% |
| NS5B | 30 nM |

Protocol

The assay reaction was performed in a Microfluor™ white "U" bottom plate (Dynatech™ #7105), by successively adding:

20 μL of test compound cocktail;

20 μL of substrate cocktail; and

20 μL of enzyme cocktail (final [NS5B] in assay=10 nM; final [n-dodecyl maltoside] in assay=0.33%; final DMSO in assay=5%).

The reaction was incubated at room temperature for 1.5 hours. STOP solution (20 μL; 0.5 M EDTA, 150 ng/μl tRNA) was added, followed by 30 μl streptavidin coated PVT beads (8 mg/ml in 20 mM Tris-HCl, pH 7.5, 25 mM KCl, 0.025% NaN$_3$). The plate was then shaken for 30 minutes. A solution of CsCl was added (70 μL, 5 M), to bring the CsCl concentration to 1.95 M. The mixture was then allowed to stand for 1 hour. The beads were then counted on a Hewlett Packard TopCount™ instrument using the following protocol:

Data mode: counts per minute

Scintillator: liq/plast

Energy range: low

Efficiency mode: normal

Region: 0–50

Count delay: 5 minutes

Count time: 1 minute

Expected results: 6000 cpm/well 200 cpm/well no enzyme control.

Based on the results at ten different concentrations of test compound, standard concentration-% inhibition curves were plotted and analysed to determine IC$_{50}$'s for the compounds of the invention. For some compounds, the IC$_{50}$ was estimated from two points.

Example 23

Specificity of NS5B RNA Dependent RNA Polymerase Inhibition

Some of the compounds of the invention were tested for inhibitory activity against polio virus RNA dependent RNA polymerase and the polio virus in the format that is described for the HCV polymerase with the exception that polio virus polymerase was used in place of the HCV NS5B polymerase. Select compounds were also tested for inhibitor of the calf thymus DNA-dependent RNA polymerase II (Kim and Dahimus, 1998, J. Biol. Chem. 263, 18880–18885).

Example 24

Cell Based HCV RNA Replication Assay

Cell Culture

Huh7 cells that stably maintain a subgenomic HCV replicon were established as previously described (Lohman et al., 1999. Science 285: 110–113) and designated as the S22.3 cell-line. S22.3 cells were maintained in Dulbecco's Modified Earle Medium (DMEM) supplemented with 10% FBS and 0.5 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 100 000 cells/ml in Standard Medium. 100μL (10 000 cells) are distributed into each well of a 96-well plate. The plate was then incubated at 37° C. with 5% CO$_2$ until the next day.

Reagents and Materials

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bia-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | RT |
| PVDF 0.22 μm Filter Unit | Millipore | SLGV025LS | RT |
| Deep-Well Titer Plate Polypropylene | Beckman | 267007 | RT |

Preparation of Test Compound

10 μL of test compound (in 100% DMSO) was added to 2 ml of Assay Medium for a final DMSO concentration of 0.5% and the solution was sonicated for 15 min and filtered through a 0.22 μM Millipore Filter Unit. 900 μl was transferred into row A of a Polypropylene Deep-Well Titer Plate. Rows B to H, contain 400 μL aliquots of Assay Medium (containing 0.5% DMSO), and were used to prepare serial dilutions (1/2) by transferring 400 μl from row to row (no compound was included in row H).

Application of Test Compound to Cells

Cell culture medium was aspirated from the 96-well plate containing the S22.3 cells. 175 μL of assay medium with the appropriate dilution of test compound was transferred from each well of the compound plate to the corresponding well of the cell culture plate (row H was used as the "No inhibition control"). The cell culture plate was incubated at 37° C. with 5% $CO_2$ for 72 hours.

Extraction of Total Cellular RNA

Following the 72 hour incubation period, the total cellular RNA was extracted from the S22.3 cells of the 96-well plate using the RNeasy 96 kit (Qiagen®, RNeasy Handbook. 1999.). Briefly, assay medium was completely removed from cells and 100 μL of RLT buffer (Qiagen®) containing 143 mM β-mercaptoethanol was added to each well of the 96-well cell-culture plate. The microplate was gently shaken for 20 sec. 100 μL of 70% ethanol was then added to each microplate well, and mixed by pipetting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 ml of Buffer RW1 (Qiagen® RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 μL of RNase-free water to each well, sealing plate with a new piece of tape and incubated for 1 min at room temperature. The plate was then centrifuged at 6000 rpm for 4 min at room temperature. The elution step was repeated with a second volume of 50 μl RNase-free water. The microtubes with total cellular RNA are stored at −70° C.

Quantification of Total Cellular RNA

RNA was quantified on the STORM® system (Molecular Dynamics®) using the RiboGreen® RNA Quantification Kit (Molecular Probes®). Briefly, the RiboGreen reagent was diluted 200-fold in TE (10 mM Tris-HCl pH=7.5, 1 mM EDTA). Generally, 50 μL of reagent was diluted in 10 mL TE. A Standard Curve of ribosomal RNA was diluted in TE to 2 μg/mL and pre-determined amounts (100, 50, 40, 20, 10, 5, 2 and 0 μL) of the ribosomal RNA solution were then transferred to a new 96-well plate (COSTAR #3997) and the volume was completed to 100 μL with TE. Generally, column 1 of the 96-well plate was used for the standard curve and the other wells were used for the RNA samples to be quantified. 10 μL of each RNA sample that was to be quantified, was transferred to the corresponding well of the 96-well plate and 90 μL of TE was added. One volume (100 μL) of diluted RiboGreen reagent was added to each well of the 96-well plate and incubated for 2 to 5 minutes at room temperature, protected from light (a 10 μL RNA sample in a 200 μL final volume generates a 20×dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20×dilution.

Reagents and Materials:

| Product | Company | Catalog # | Storage |
| --- | --- | --- | --- |
| DEPC | Sigma | D5758 | 4° C. |
| EDTA | Sigma | E5134 | RT |
| Trizma-Base | Sigma | T8524 | RT |
| Trizma-HCl | Sigma | T7149 | RT |
| Collection Tube Strips | Qiagen | 19562 | RT |
| Ribogreen RNA Quantitation Kit | Molecular Probe | R11490 | −20° C. |
| Rneasy 96 Kit | Qiagen | 74183 | RT |
| Square-Well Blocks | Qiagen | 19573 | RT |

Real-Time RT-PCR

The Real-Time RT-PCR was performed on the ABI Prism 7700 Sequence Detection System using the TaqMan EZ RT-PCR Kit from (Perkin-Elmer Applied Biosystems®). RT-PCR was optimized for the quantification of the 5' IRES of HCV RNA by using the Taqman technology (Roche Molecular Diagnostics Systems) similar to the technique previously described (Martell et al., 1999. J. Clin. Microbiol. 37: 327–332). The system exploits the 5'-3' nucleolytic activity of AmpliTaq DNA polymerase. Briefly, the method utilizes a dual-labeled fluorogenic hybridization probe (SEQ ID NO. 4) that specifically anneals to the template between the PCR primers (SEQ ID NO. 2 and SEQ ID NO. 3). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportional to the signal. An amplification plot represents the logarithmic phase of product accumulation and a point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration. Reference samples for the standard curve are included on each RT-PCR plate. HCV Replicon RNA was synthesized (by T7 transcription) in vitro, purified and quantified by $OD_{260}$. Considering that 1 μg of this RNA=$2.15 \times 10^{11}$ RNA copies, dilutions are made in order to have $10^8$, $10^7$, $10^6$, $10^5$, $10^4$, $10^3$ or $10^2$ genomic RNA copies/5 μL. Total cellular Huh-7

RNA was also incorporated with each dilution (50 ng/5 µL). 5 µL of each reference standard (HCV Replicon+Huh-7 RNA) was combined with 45 µL of Reagent Mix, and used in the Real-Time RT-PCR reaction.

The Real-Time RT-PCR reaction was set-up for the experimental samples that were purified on RNeasy 96-well plates by combining 5 µl of each total cellular RNA sample with 45 µL of Reagent Mix.

Reagents and Materials

| Product | Company | Catalog # | Storage |
|---|---|---|---|
| TaqMan EZ RT-PCR Kit | PE Applied Biosystems | N808-0236 | −20° C. |
| MicroAmp Optical Caps | PE Applied Biosystems | N801-0935 | RT |
| MicroAmp Optical 96-Well Reaction Plate | PE Applied Biosystems | N801-0560 | RT |

Reagent Mix Preparation

| Component | Volume for one sample (µL) | Volume for One Plate (µL) (91 samples + Dead Volume) | Final conc. |
|---|---|---|---|
| Rnase-free water | 16.5 | 1617 | |
| 5X TaqMan EZ buffer | 10 | 980 | 1X |
| Mn(OAc)$_2$ (25 mM) | 6 | 588 | 3 mM |
| dATP (10 mM) | 1.5 | 147 | 300 µM |
| dCTP (10 mM) | 1.5 | 147 | 300 µM |
| dGTP (10 mM) | 1.5 | 147 | 300 µM |
| dUTP (20 mM) | 1.5 | 147 | 600 µM |
| Forward Primer (10 µM) | 1 | 98 | 200 nM |
| Reverse Primer (10 µM) | 1 | 98 | 200 nM |
| PUTR probe (5 µM) | 2 | 196 | 200 nM |
| rTth DNA polymerase (2.5 U/µL) | 2 | 196 | 0.1 U/µL |
| AmpErase UNG (1 U/µL) | 0.5 | 49 | 0.01 U/µL |
| Total Volume | 45 | 4410 | |

```
Forward Primer Sequence:              (SEQ ID NO. 2)
5'-ACG CAG AAA GCG TCT AGC CAT GGC GTT AGT-3'

Reverse Primer Sequence:              (SEQ ID NO. 3)
5'-TCC CGG GGC ACT CGC AAG CAC CCT ATC AGG-3'
```

Note

Those primers amplify a region of 256-nt present within the 5' untranslated region of HCV.

```
PUTR Probe Sequence (SEQ ID NO. 4):
[6FAM] - TGG TCT GCG GAA CCG GTG AGT ACA CC-[TAMRA]
```

No Template Controls (NTC)

On each plate, 4 wells are used as "NTC". For these controls, 5 µl of water are added to the well in place of RNA.

| Thermal Cycling Conditions: | |
|---|---|
| 50° C. | 2 min |
| 60° C. | 30 min |

-continued

| Thermal Cycling Conditions: | | |
|---|---|---|
| 95° C. | 5 min | |
| 95° C. | 15 sec | } for 2 cycles |
| 60° C. | 1 min | |
| 90° C. | 15 sec | } for 40 cycles |
| 60° C. | 1 min | |

Following the termination of the RT-PCR reaction the data analysis requires setting of threshold fluorescence signal for the PCR plate and a standard curve was constructed by plotting the Ct value versus RNA copy number used in each reference reaction. The Ct values obtained for the assay samples were used to interpolate an RNA copy number based on the standard curve.

Finally, the RNA copy number was normalized (based on the RiboGreen RNA quantification of the total RNA extracted from the cell culture well) and expressed as genome equivalents/µg of total RNA [ge/µg].

The RNA copy number [g.e./µg] from each well of the cell culture plate was a measure of the amount of replicating HCV RNA in the presence of various concentrations of inhibitor. The % inhibition was calculated with the following equation:

$$[100-([g.e./\mu g]inh/[g.e./\mu g]ct) \times 100].$$

A non-linear curve fit with the Hill model was applied to the inhibition-concentration data, and the 50% effective concentration (EC$_{50}$) was calculated by the use of SAS software (Statistical Software System; SAS Institute, Inc. Cary, N.C.).

Table of Compounds

The compounds listed in Tables 1 to 3 were found to be active in the above-described NS5B assay (described in Example 22), with IC$_{50}$'s of less than 25 µM. None of these compounds were found to exhibit significant inhibition of poliovirus RNA dependent RNA polymerase or calf thymus DNA dependent RNA polymerase II (of Example 23) at 25 µM concentration. The compounds were also active in the cell-based assay, with EC$_{50}$'s of less than 50 µM.

In the Tables 1 to 3, the following ranges apply:

For IC$_{50}$ A=25 µM–5 µM; B=5–0.5 µM; and C=<0.5 µM

For EC$_{50}$ A=50 µM–5 µM; and B=≦5 µM

TABLE 1

| Cpd. # | R³ R⁴ | A | IC$_{50}$ | EC$_{50}$ | m/z (M + H)⁺ |
|---|---|---|---|---|---|
| 1001 | gem-dimethyl | 3-carboxyphenyl | B | — | 501.1 |
| 1002 | gem-dimethyl | 3-(2-carboxyvinyl)phenyl | B | — | 527.2 |
| 1003 | gem-dimethyl | 4-(3-carboxypropyl)phenyl | B | — | 543.2 |
| 1004 | gem-dimethyl | 3-(carboxymethyl)-4-hydroxyphenyl | B | — | 531.2 |
| 1005 | phenyl/cyclopropane | 4-(2-carboxyvinyl)phenyl | B | — | 589.3 |

TABLE 1-continued

| Cpd. # | R³R⁴ | A | IC₅₀ | EC₅₀ | m/z (M + H)⁺ |
|---|---|---|---|---|---|
| 1006 | phenyl-CH-CH | 4-(2-carboxyvinyl)phenyl | B | — | 589.3 |
| 1007 | CH-CH | 3-(carboxymethyl)phenyl | B | — | 515.3 |
| 1008 | CH-CH | 4-(carboxymethyl)phenyl | B | — | 515.3 |
| 1009 | CH-CH | 4-(1-carboxyethyl)phenyl | B | — | 529.3 |
| 1010 | CH-CH | 3-(2-carboxyvinyl)-4-chlorophenyl | B | — | 562.1 |
| 1011 | CH-CH | 3-(2-carboxy-2-ethylvinyl)phenyl | B | — | 555.2 |

TABLE 1-continued
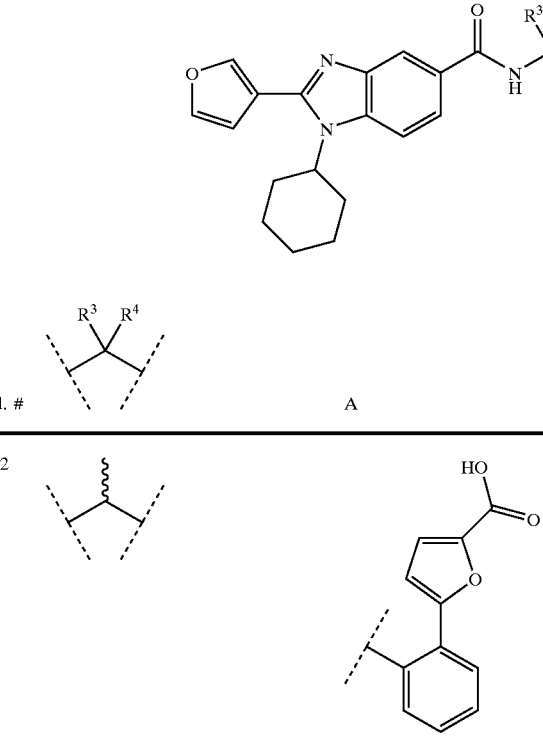
| Cpd. # | R³ R⁴ | A | IC$_{50}$ | EC$_{50}$ | m/z (M + H)⁺ |
|---|---|---|---|---|---|
| 1012 | 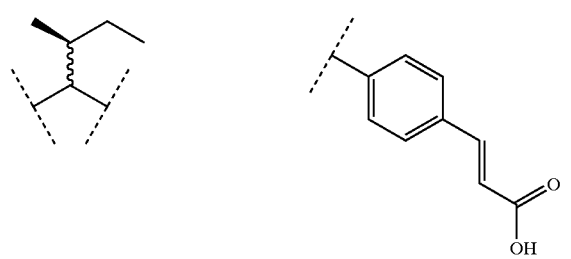 | | B | — | 567.2 |
| 1013 | | | B | — | 569.3 |
| 1014 | 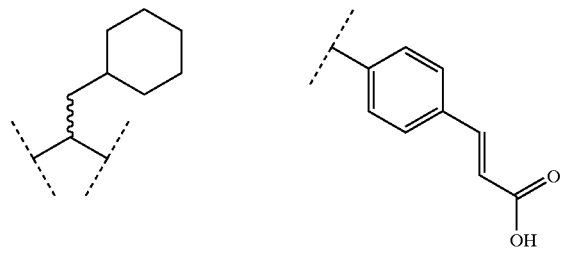 | | B | — | 609.2 |
| 1015 | 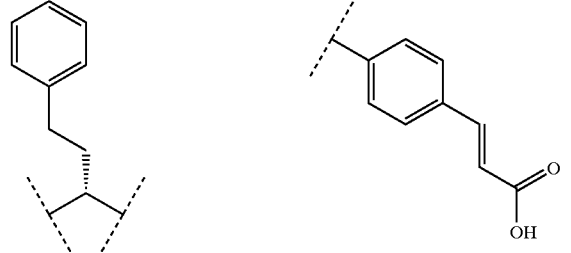 | | B | — | 617.2 |

TABLE 1-continued

| Cpd. # | R³R⁴ | A | IC₅₀ | EC₅₀ | m/z (M + H)⁺ |
|---|---|---|---|---|---|
| 1016 | phenyl | 4-(carboxyvinyl)phenyl | B | — | 589.3 |
| 1017 | cyclohexyl | 4-(carboxyvinyl)phenyl | B | — | 595.2 |
| 1018 | 4-biphenylmethyl | 4-(carboxyvinyl)phenyl | A | — | 679.3 |
| 1019 | thien-2-yl | 4-(carboxyvinyl)phenyl | B | — | 595.2 |
| 1020 | H | 3'-hydroxybiphenyl-3-yl | A | — | 549.2 |

TABLE 1-continued

| Cpd. # | R³ R⁴ | A | IC$_{50}$ | EC$_{50}$ | m/z (M + H)⁺ |
|---|---|---|---|---|---|
| 1021 | gem-dimethyl | 4'-hydroxy-biphenyl-3-yl | A | — | 549.2 |
| 1022 | gem-dimethyl | 3'-amino-biphenyl-3-yl | B | A | 548.2 |
| 1023 | trans-cyclopropyl | 2-[4-(carboxymethoxy)phenyl]thiazol-5-yl | B | — | 614.2 |
| 1024 | trans-cyclopropyl | 4-(2-aminothiazol-4-yl)phenyl | B | — | 555.2 |
| 1025 | trans-cyclopropyl | 4-(2-methyl-2-carboxyethoxy)phenyl | B | — | 559.2 |

TABLE 1-continued

| Cpd. # | R³ R⁴ | A | IC$_{50}$ | EC$_{50}$ | m/z (M + H)⁺ |
|---|---|---|---|---|---|
| 1026 | | 4-methylcoumarin-7-yl | B | B | 539.2 |
| 1027 | | 5-(4-yl-phenyl)-2-methyl-furan-3-carboxylic acid | B | — | 581.2 |
| 1028 | spiro-cyclopentyl | coumarin-6-yl | B | — | 565.2 |
| 1029 | spiro-cyclopentyl | 4-trifluoromethylcoumarin-7-yl | A | — | 633.2 |
| 1030 | spiro-cyclopentyl | 4-(methoxymethyl)coumarin-7-yl | B | — | 609.2 |

TABLE 1-continued

| Cpd. # | R³ R⁴ | A | IC$_{50}$ | EC$_{50}$ | m/z (M + H)⁺ |
|---|---|---|---|---|---|
| 1031 | spiro-cyclopentyl | 4-(5-methoxycarbonyl-furan-2-yl)phenyl | B | — | 621.2 |
| 1032 | methyl (single) | 4-(furan-3-yl)phenyl | B | — | 523.2 |
| 1033 | spiro-cyclopentyl | 4-[(E)-2-ethoxycarbonylvinyl]phenyl | A | — | 595.2 |
| 1034 | spiro-cyclopentyl | 3-methyl-2-ethoxycarbonyl-benzothiophen-5-yl | B | — | 639.2 |
| 1035 | methyl (single) | 4-(5-oxo-2,5-dihydrofuran-3-yl)phenyl | B | — | 539.2 |

TABLE 1-continued
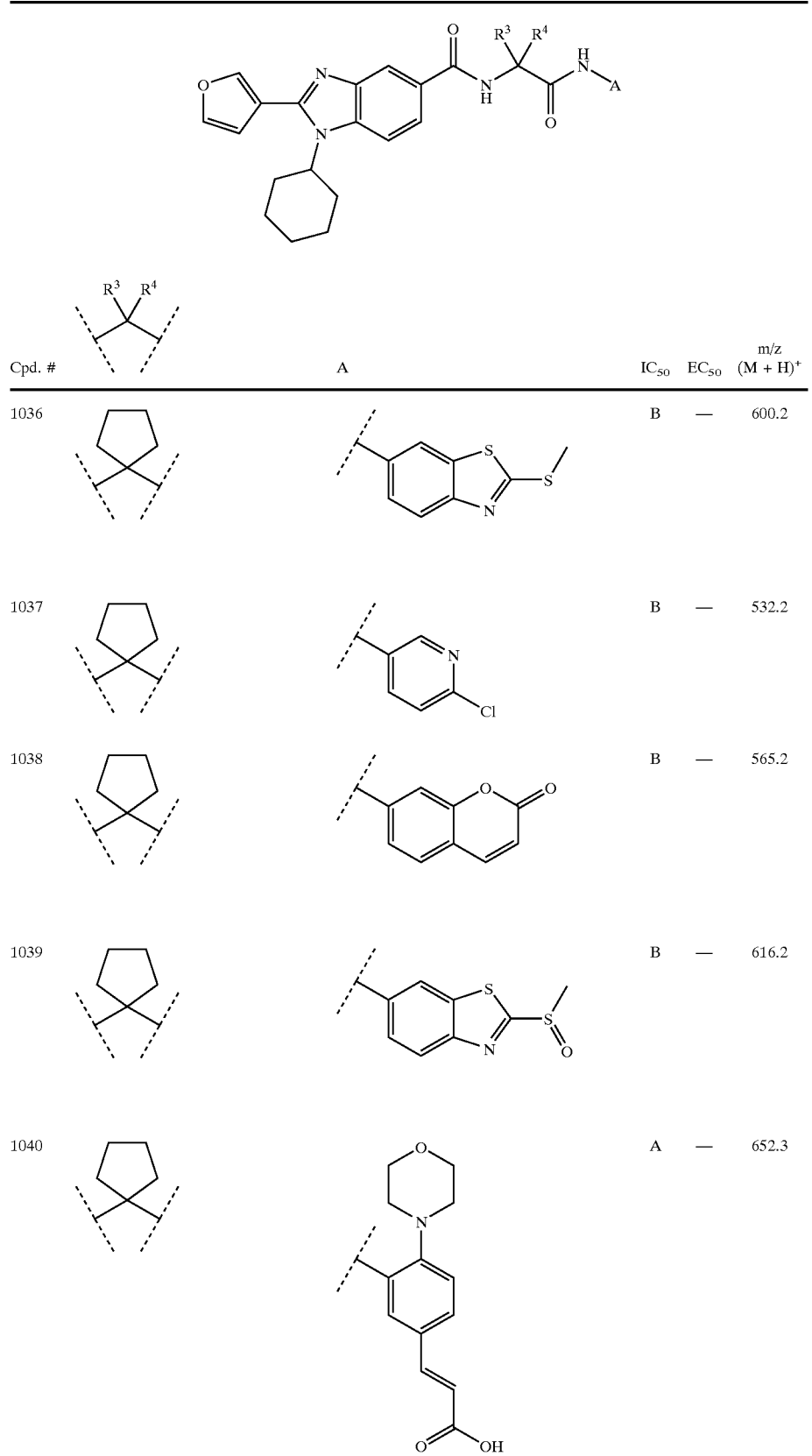
| Cpd. # | R³ R⁴ | A | IC$_{50}$ | EC$_{50}$ | m/z (M + H)⁺ |
|---|---|---|---|---|---|
| 1036 | cyclopentane spiro | 2-(methylthio)benzothiazol-6-yl | B | — | 600.2 |
| 1037 | cyclopentane spiro | 6-chloropyridin-3-yl | B | — | 532.2 |
| 1038 | cyclopentane spiro | 2-oxo-2H-chromen-7-yl | B | — | 565.2 |
| 1039 | cyclopentane spiro | 2-(methylsulfinyl)benzothiazol-6-yl | B | — | 616.2 |
| 1040 | cyclopentane spiro | 4-morpholino-3-(2-carboxyvinyl)phenyl | A | — | 652.3 |

TABLE 1-continued

| Cpd. # | R³ R⁴ | A | IC$_{50}$ | EC$_{50}$ | m/z (M + H)⁺ |
|---|---|---|---|---|---|
| 1041 | cyclopentane | 1-benzyl-indole-2-carboxylic acid (5-linked) | B | — | 670.3 |
| 1042 | cyclopentane | 6-morpholino-pyridin-3-yl | B | — | 583.3 |
| 1043 | cyclopentane | 4-(1-methoxy-2-carboxyethyl)phenyl | B | — | 599.3 |
| 1044 | cyclopentane | 2-chloro-4-carboxyphenyl | B | — | 575.2 |
| 1045 | cyclopentane | 4-methoxy-3-carboxyphenyl | B | — | 571.2 |

TABLE 1-continued
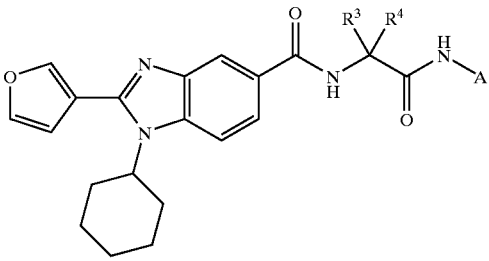
| Cpd. # | R³ R⁴ | A | IC$_{50}$ | EC$_{50}$ | m/z (M + H)⁺ |
|---|---|---|---|---|---|
| 1046 | 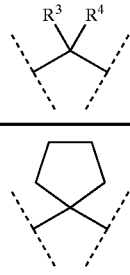 | 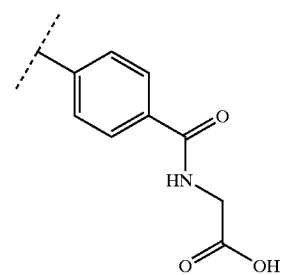 | B | — | 598.2 |
| 1047 | 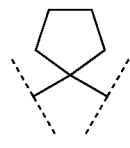 | 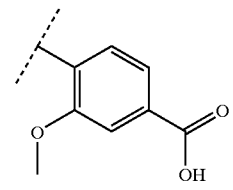 | B | — | 571.2 |
| 1048 | 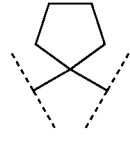 | 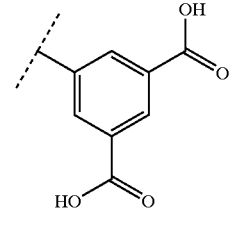 | B | — | 585.2 |
| 1049 | 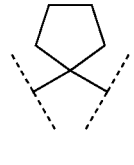 | 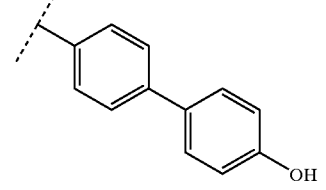 | B | — | 589.3 |
| 1050 | 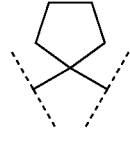 | 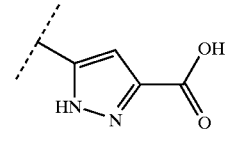 | B | — | 531.2 |
| 1051 | 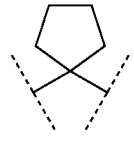 | 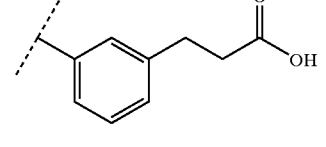 | B | — | 569.2 |

TABLE 1-continued

| Cpd. # | R³ R⁴ | A | IC₅₀ | EC₅₀ | m/z (M + H)⁺ |
|---|---|---|---|---|---|
| 1052 | spiro[4.4] (cyclopentyl) | 3-(methoxycarbonyl)-5-carboxyphenyl | B | — | 599.2 |
| 1053 | CH₂ | 4-carboxyphenyl | B | A | 501.1 |
| 1054 | CH₂ | 4-(2-carboxyvinyl)phenyl | C | A | 527.2 |
| 1055 | CH₂ | 3-hydroxy-4-hydroxy... (4-hydroxy-3-carboxyphenyl) | B | — | 517.2 |
| 1056 | CH(CH₃) | 4-(2-carboxyvinyl)phenyl | C | A | 527.2 |

TABLE 1-continued

| Cpd. # | R³ R⁴ | A | IC$_{50}$ | EC$_{50}$ | m/z (M + H)⁺ |
|---|---|---|---|---|---|
| 1057 | | 4-(carboxyvinyl)phenyl (trans) | C | A | 527.2 |
| 1058 | | 4-(carboxyvinyl)phenyl | B | — | 531.2 |
| 1059 | | 3-(carboxymethoxy)phenyl | B | — | 531.2 |
| 1060 | | 4-(5-carboxyfuran-2-yl)phenyl | C | A | 567.2 |
| 1061 | | 3-(5-carboxyfuran-2-yl)phenyl | C | — | 567.2 |

TABLE 1-continued

| Cpd. # | R³ R⁴ | A | IC₅₀ | EC₅₀ | m/z (M + H)⁺ |
|---|---|---|---|---|---|
| 1062 | benzyl | 4-(CH=CH-COOH)phenyl | B | — | 603.3 |
| 1063 | ethyl | 4-(CH=CH-COOH)phenyl | C | — | 555.2 |
| 1064 | CH₂CH₂OH | 4-(CH=CH-COOH)phenyl | B | — | 557.3 |
| 1065 | methyl | 3-(5-carboxyfuran-2-yl)phenyl | C | — | 567.2 |
| 1066 | methyl | 4-(5-carboxyfuran-2-yl)phenyl | C | — | 567.2 |

TABLE 1-continued
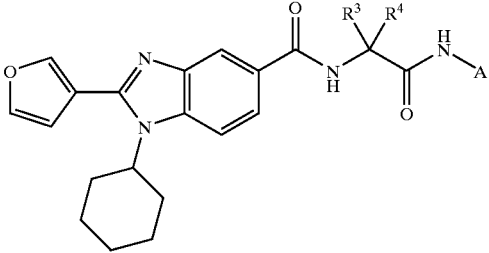
| Cpd. # | R³ R⁴ | A | IC₅₀ | EC₅₀ | m/z (M + H)⁺ |
|---|---|---|---|---|---|
| 1067 | 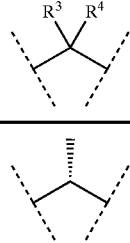 | 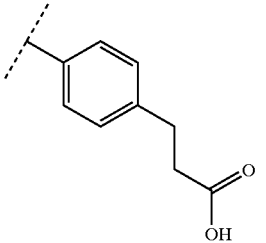 | B | — | 529.2 |
| 1068 | 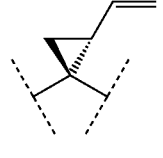 | 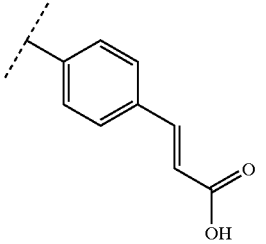 | C | B | 565.2 |
| 1069 | 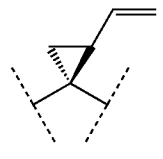 | 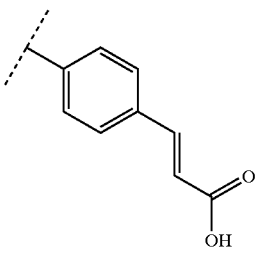 | C | B | 565.3 |
| 1070 | 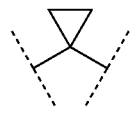 | 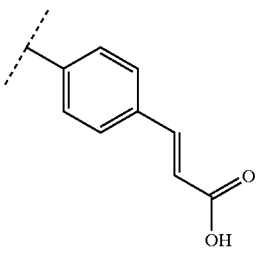 | C | A | 539.2 |

TABLE 1-continued
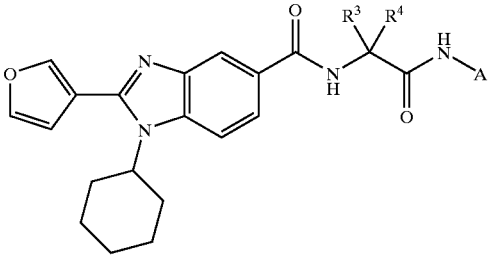
| Cpd. # | R³ R⁴ 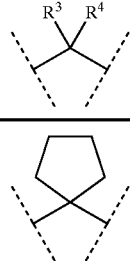 | A | IC$_{50}$ | EC$_{50}$ | m/z (M + H)⁺ |
|---|---|---|---|---|---|
| 1071 | 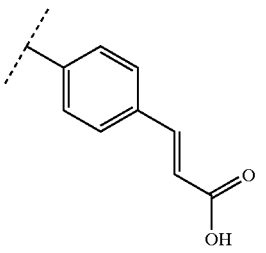 | 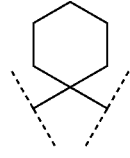 | C | B | 567.3 |
| 1072 | 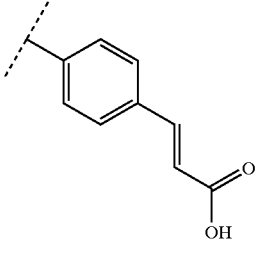 | 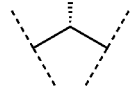 | C | B | 581.2 |
| 1073 | 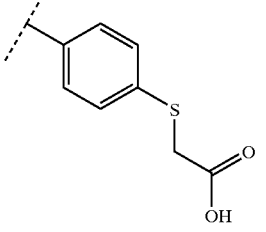 | 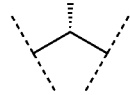 | B | — | 547.2 |
| 1074 | 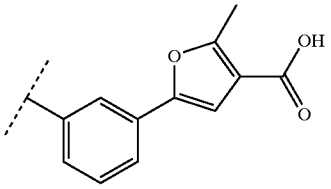 | 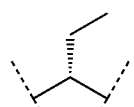 | B | B | 581.2 |
| 1075 | 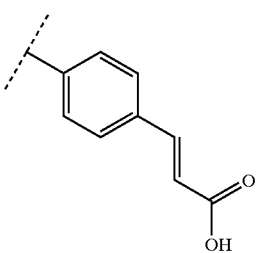 | | C | A | 541.3 |

TABLE 1-continued

| Cpd. # | R³ R⁴ | A | IC₅₀ | EC₅₀ | m/z (M + H)⁺ |
|---|---|---|---|---|---|
| 1076 | (sec-butyl-like) | 4-(2-carboxyvinyl)phenyl | B | B | 555.3 |
| 1077 | cyclopentyl (spiro) | 1-methyl-2-carboxy-indol-5-yl | C | B | 594.3 |
| 1078 | cyclopentyl (spiro) | 2-mercaptobenzothiazol-6-yl | B | B | 586.1 |
| 1079 | diethyl | 4-(2-carboxyvinyl)phenyl | C | A | 513.1 |
| 1080 | cyclopentyl (spiro) | 4-(5-carboxyfuran-2-yl)phenyl | C | B | 607.2 |

TABLE 1-continued

| Cpd. # | R³ R⁴ | A | IC₅₀ | EC₅₀ | m/z (M + H)⁺ |
|---|---|---|---|---|---|
| 1081 | cyclopentane spiro | 4-oxo-1H-quinoline-2-carboxylic acid, 6-yl | C | — | 608.2 |
| 1082 | cyclopentane spiro | 4-methyl-2-oxo-2H-chromen-7-yl | B | — | 579.3 |
| 1083 | cyclopentane spiro | 4-(2-methyl-2-carboxyvinyl)phenyl | C | B | 581.3 |
| 1084 | cyclopentane spiro | 4-[(4-methyl-5-carboxythiazol-2-yl)amino]phenyl | B | — | 654.3 |
| 1085 | cyclopentane spiro | 1-ethyl-2-carboxy-1H-indol-5-yl | C | B | 608.3 |

TABLE 1-continued

| Cpd. # | R³/R⁴ | A | IC₅₀ | EC₅₀ | m/z (M + H)⁺ |
|---|---|---|---|---|---|
| 1086 | spiro-cyclopentyl | 5-(1-propargyl-indole-2-carboxylic acid)yl | C | — | 618.2 |
| 1087 | methyl/H | 5-(1-methyl-indole-2-carboxylic acid)yl | C | — | 554.3 |
| 1088 | spiro-cyclopentyl | 4-(2-methylphenyl)acrylic acid | C | B | 581.3 |
| 1089 | 4-Boc-piperidinyl spiro | 4-phenylacrylic acid | C | B | 682.3 |
| 1090 | spiro-cyclopentyl | 4-(thiazole-4-carboxylic acid-2-yl)phenyl | C | — | 624.2 |

US 6,841,566 B2
TABLE 1-continued
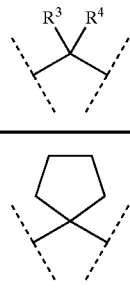
| Cpd. # | R³ R⁴ | A | IC$_{50}$ | EC$_{50}$ | m/z (M + H)⁺ |
|---|---|---|---|---|---|
| 1091 | 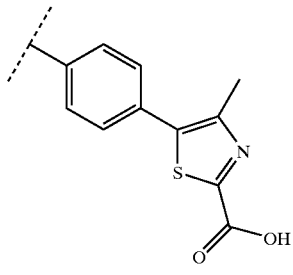 | 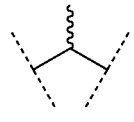 | B | B | 638.2 |
| 1092 | 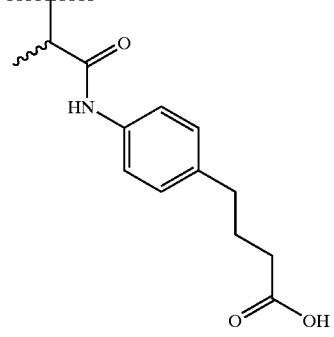 |  | A | — | 614.3 |
| 1093 | 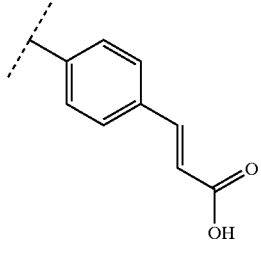 | 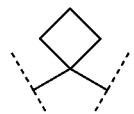 | C | B | 541.2 |
| 1094 | 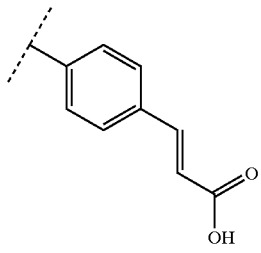 | | C | B | 553.2 |

TABLE 1-continued

| Cpd. # | R³ R⁴ | A | IC₅₀ | EC₅₀ | m/z (M + H)⁺ |
|---|---|---|---|---|---|
| 1095 | cyclopentane spiro | 4-(carboxyvinyl)phenyl | C | B | 567.3 |
| 1096 | dimethyl | benzofuran-2-carboxylic acid-5-yl | C | — | 541.2 |
| 1097 | dimethyl | indole-2-carboxylic acid-5-yl | C | — | 540.2 |
| 1098 | cyclopentane spiro | indole-2-carboxylic acid-5-yl | C | A | 580.3 |
| 1099 | cyclopentane spiro | 3-methylbenzothiophene-2-carboxylic acid-5-yl | C | B | 611.2 |
| 1100 | piperidine spiro | 4-(carboxyvinyl)phenyl | C | B | 582.3 |

TABLE 1-continued
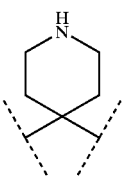
| Cpd. # | R³ R⁴ | A | IC$_{50}$ | EC$_{50}$ | m/z (M + H)⁺ |
|---|---|---|---|---|---|
| 1101 | 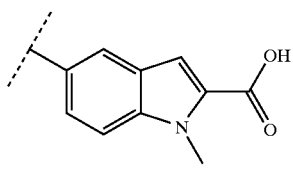 | 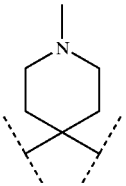 | C | — | 609.3 |
| 1102 | 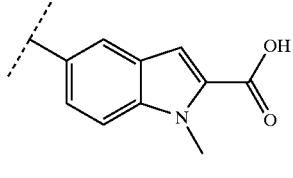 |  | C | — | 623.2 |
| 1103 | 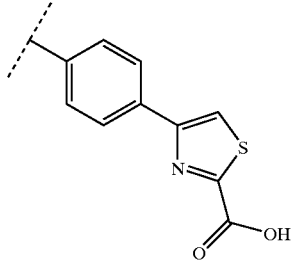 |  | C | — | 598.2 |
| 1104 | 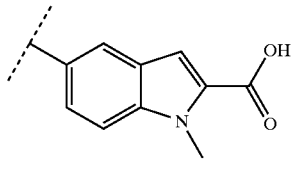<br>(+) enantiomer | 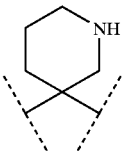 | B | B | 609.3 |
| 1105 | 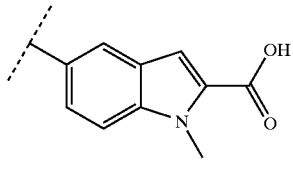<br>(−) enantiomer | | C | B | 609.3 |

TABLE 1-continued
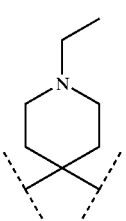
| Cpd. # | R³ R⁴ | A | IC$_{50}$ | EC$_{50}$ | m/z (M + H)⁺ |
|---|---|---|---|---|---|
| 1108 | 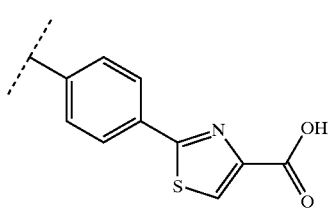 | 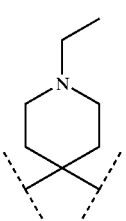 | C | B | 667.3 |
| 1109 | 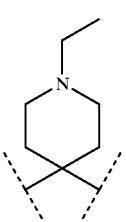 | 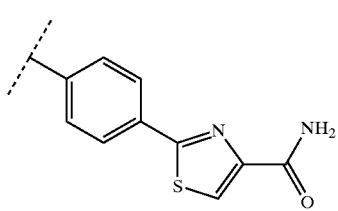 | C | B | 666.3 |
| 1110 | 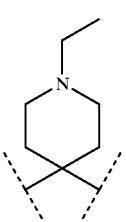 |  | C | — | 721.2 |
| 1111 | 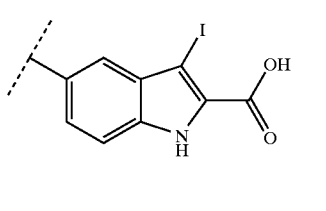 |  | B | — | 590.4 |

TABLE 2
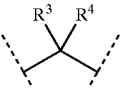
| Cpd. # | R¹ | R² | R³ R⁴ | IC$_{50}$ | EC$_{50}$ | m/z (M + H)⁺ |
|---|---|---|---|---|---|---|
| 2001 |  |  |  | C | B | 583.2 |
| 2002 | 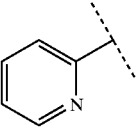 |  | 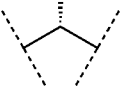 | C | B | 538.3 |
| 2003 |  |  | 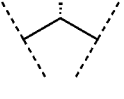 | B | A | 537.2 |
| 2004 | 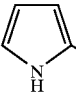 | 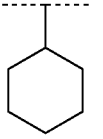 | 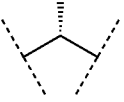 | C | A | 526.2 |
| 2005 | 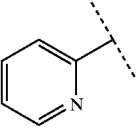 | 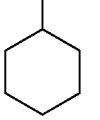 | 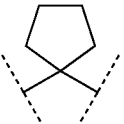 | C | B | 578.3 |
| 2006 | 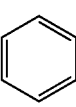 | 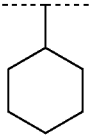 |  | B | B | 577.3 |
| 2007 | 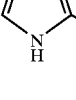 | 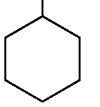 | 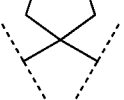 | C | B | 566.3 |
| 2008 | 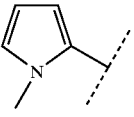 |  | 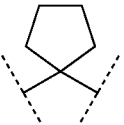 | B | — | 566.3 |

TABLE 2-continued
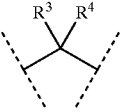
| Cpd. # | R¹ | R² | R³ R⁴ | IC$_{50}$ | EC$_{50}$ | m/z (M + H)⁺ |
|---|---|---|---|---|---|---|
| 2009 | 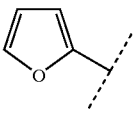 | 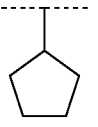 | 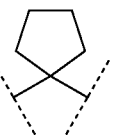 | B | — | 553.2 |
| 2010 | 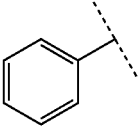 | 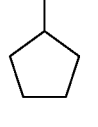 | 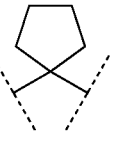 | B | — | 563.3 |
| 2011 | 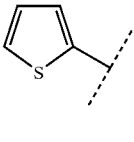 | 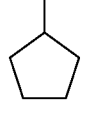 | 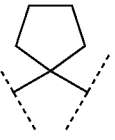 | B | — | 569.2 |
| 2012 | 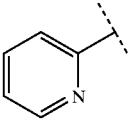 | 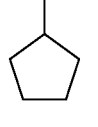 | 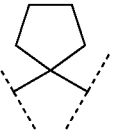 | B | A | 564.3 |
| 2013 | 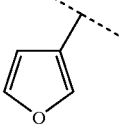 | 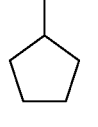 | 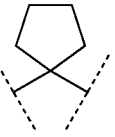 | C | A | 553.2 |
| 2014 | 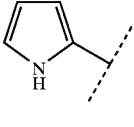 | 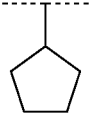 | 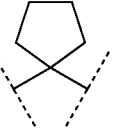 | B | — | 552.2 |
| 2015 | 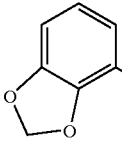 | 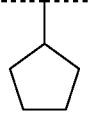 | 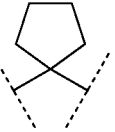 | B | — | 607.2 |

TABLE 2-continued
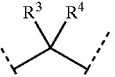
| Cpd. # | R¹ | R² | 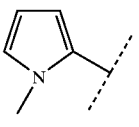 R³ R⁴ | IC$_{50}$ | EC$_{50}$ | m/z (M + H)⁺ |
|---|---|---|---|---|---|---|
| 2016 | 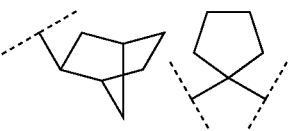 |  Racemic mixture | 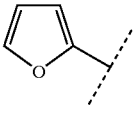 | B | — | 592.3 |
| 2017 | 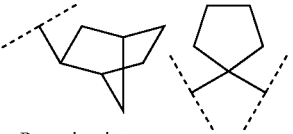 |  Racemic mixture | | C | B | 579.3 |
| 2018 | 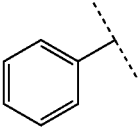 | 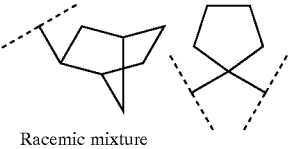 Racemic mixture | | B | — | 589.3 |
| 2019 |  | 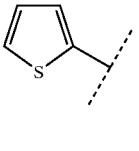 Racemic mixture | | C | B | 595.2 |
| 2020 | 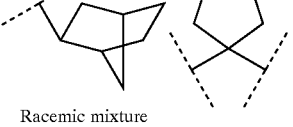 |  Racemic mixture | | C | B | 590.3 |
| 2021 | 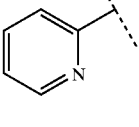 | 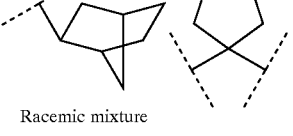 Racemic mixture | | C | B | 579.3 |
| 2022 |  | 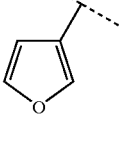 Racemic mixture | | B | — | 578.3 |

TABLE 2-continued
| Cpd. # | R¹ | R² | R³ R⁴ | IC$_{50}$ | EC$_{50}$ | m/z (M + H)⁺ |
|---|---|---|---|---|---|---|
| 2023 | 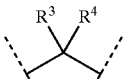 | 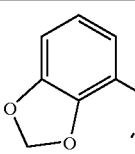 Racemic mixture | 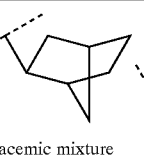 | B | — | 633.3 |
| 2024 | 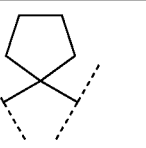 | 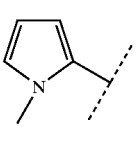 | 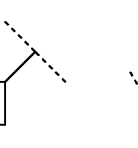 | B | — | 552.3 |
| 2025 | 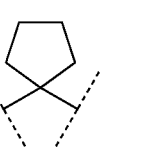 | 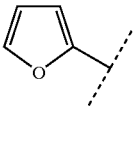 | 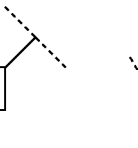 | B | — | 539.2 |
| 2026 |  | 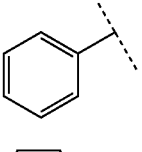 | 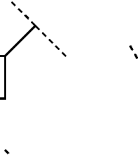 | B | — | 549.3 |
| 2027 | 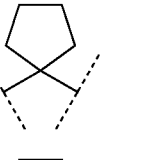 | 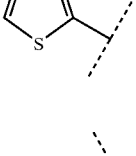 | 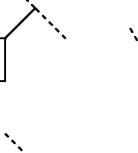 | B | — | 555.2 |
| 2028 | 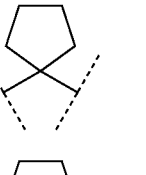 | 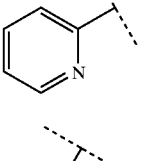 | 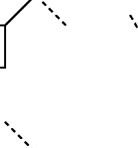 | B | — | 550.3 |
| 2029 | 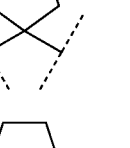 | 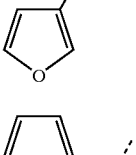 |  | B | — | 539.2 |
| 2030 | 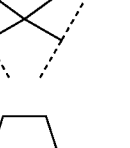 | 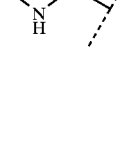 |  | B | — | 538.3 |

TABLE 2-continued
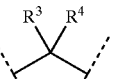
| Cpd. # | R¹ | R² | R³ R⁴ | IC$_{50}$ | EC$_{50}$ | m/z (M + H)⁺ |
|---|---|---|---|---|---|---|
| 2031 | 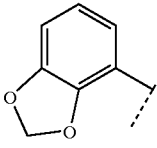 | 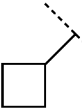 | 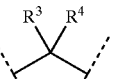 | B | — | 593.2 |
| 2032 | 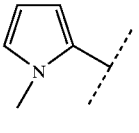 | 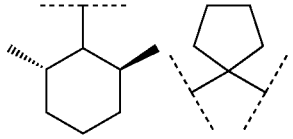<br>Mixture of enantiome diastereoisomers | 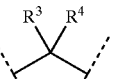 | B | — | 608.3 |
| 2033 | 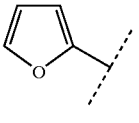 | 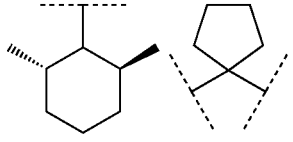<br>Mixture of enantiome diastereoisomers |  | B | B | 595.3 |
| 2034 | 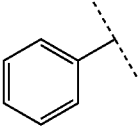 | 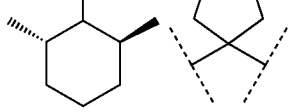<br>Mixture of enantiome diastereoisomers |  | B | — | 605.3 |
| 2035 | 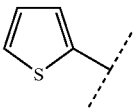 | 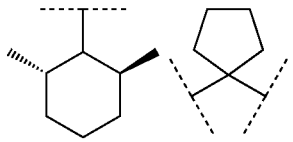<br>Mixture of enantiome diastereoisomers |  | C | B | 611.3 |
| 2036 | 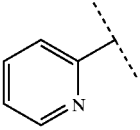 | 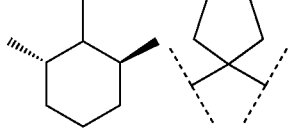<br>Mixture of enantiome diastereoisomers |  | B | B | 606.3 |

TABLE 2-continued

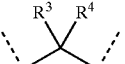

| Cpd. # | R¹ | R² | R³ R⁴ (cyclic) | IC$_{50}$ | EC$_{50}$ | m/z (M + H)⁺ |
|---|---|---|---|---|---|---|
| 2037 | furan-3-ylmethyl | trans-cyclohexyl (mixture of enantiomeric diastereoisomers) | spiro cyclopentane | B | B | 595.3 |
| 2038 | pyrrol-2-ylmethyl | trans-cyclohexyl (mixture of enantiomeric diastereoisomers) | spiro cyclopentane | B | — | 594.3 |
| 2039 | benzodioxol-4-ylmethyl | trans-cyclohexyl (mixture of enantiomeric diastereoisomers) | spiro cyclopentane | B | — | 649.3 |
| 2040 | N-methylpyrrol-2-ylmethyl | cis-cyclohexyl (racemic mixture) | spiro cyclopentane | B | — | 594.3 |
| 2041 | furan-2-ylmethyl | cis-cyclohexyl (racemic mixture) | spiro cyclopentane | B | — | 581.3 |
| 2042 | benzyl | cis-cyclohexyl (racemic mixture) | spiro cyclopentane | B | — | 591.3 |

TABLE 2-continued
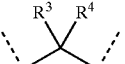
| Cpd. # | R¹ | R² | 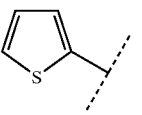 | IC$_{50}$ | EC$_{50}$ | m/z (M + H)$^+$ |
|---|---|---|---|---|---|---|
| 2043 | 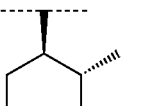 | 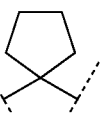<br>Racemic mixture | 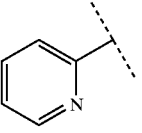 | B | — | 597.3 |
| 2044 | 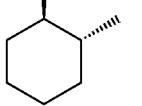 | <br>Racemic mixture | 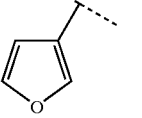 | B | B | 592.3 |
| 2045 | 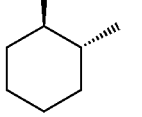 | <br>Racemic mixture | 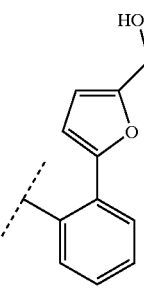 | B | B | 581.3 |
| 2046 | 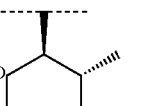 | 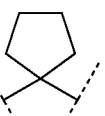<br>Racemic mixture | 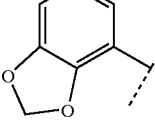 | B | — | 580.3 |
| 2047 | 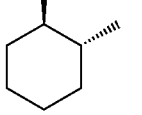 | <br>Racemic mixture | 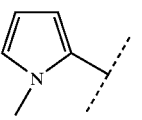 | B | — | 635.3 |
| 2048 | 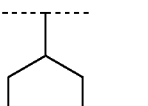 | 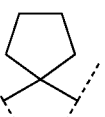 | 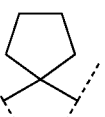 | C | B | 580.3 |

TABLE 2-continued
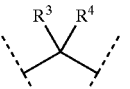
| Cpd. # | R¹ | R² |  | IC$_{50}$ | EC$_{50}$ | m/z (M + H)⁺ |
|---|---|---|---|---|---|---|
| 2049 | 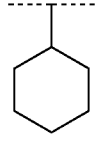 | 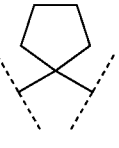 | 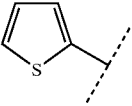 | C | B | 567.3 |
| 2050 | 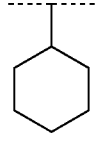 | 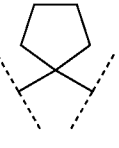 | 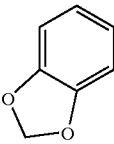 | C | B | 583.3 |
| 2051 | 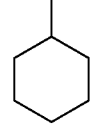 | 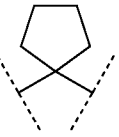 | 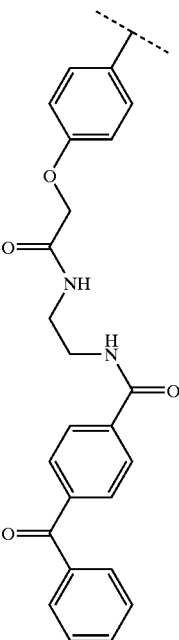 | B | — | 621.3 |
| 2052 | 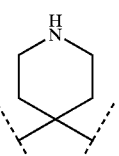 | 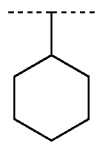 | | A | — | 917 |

TABLE 2-continued
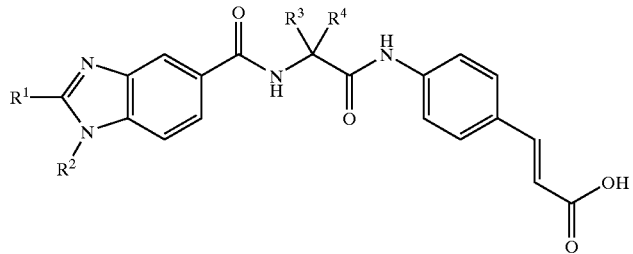
| Cpd. # | R¹ | R² | R³ R⁴ | $IC_{50}$ | $EC_{50}$ | m/z $(M + H)^+$ |
|---|---|---|---|---|---|---|
| 2053 | 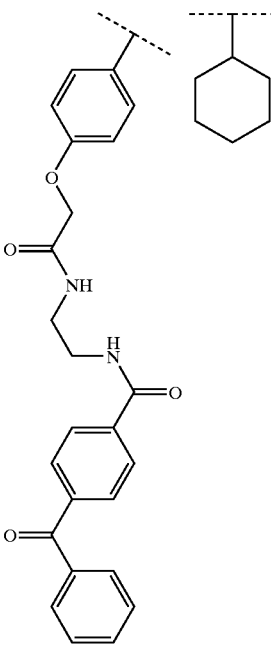 | 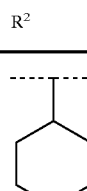 |  | A | — | 1142.4 |
TABLE 3
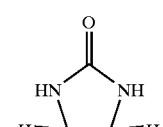
| Compound entry # | B | D | $IC_{50}$ | $EC_{50}$ | m/z$(M + H)^+$ |
|---|---|---|---|---|---|
| 3001 | N | CH | C | A | 528.2 |
| 3002 | CH | CMe | B | — | 541.2 |
| 3003 | CMe | CH | B | A | 541.2 |

We claim:

1. An isomer, enantiomer, diastereoisomer, or tautomer of a compound represented by formula I:

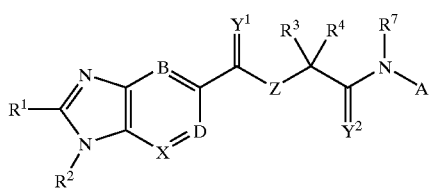

wherein $R^1$ is selected from: $R^{11}$, $OR^{11}$, $SR^{11}$, $COOR^{11}$, $SO_2N(R^{12})_2$, $N(R^{12})_2$, $CON(R^{12})_2$, $NR^{12}C(O)R^{12}$ or $NR^{12}C(O)NR^{12}$ wherein $R^{11}$ and each $R_{12}$ is independently H, ($C_{1-6}$alkyl, haloalkyl, ($C_{2-6}$) alkenyl, ($C_{3-7}$)cycloalkyl, ($C_{2-6}$)alkynyl, ($C_{5-7}$) cycloalkenyl, 6 or 10-membered aryl or Het, said $R^{11}$ and $R^{12}$ being optionally substituted with $R^{10}$; or both $R^{12}$ are bonded together to form a 5, 6 or 7-membered saturated heterocycle with the nitrogen to which they are attached;

$R^2$ is selected from ($C_{1-6}$)alkyl, haloalkyl, ($C_{3-7}$) cycloalkyl, ($C_{5-7}$)cycloalkenyl, ($C_{6-10}$)bicycloalkyl, ($C_{6-10}$)bicycloalkenyl, 6- or 10-membered aryl, Het, ($C_{1-6}$)alkyl-aryl or ($C_{1-6}$)alkyl-Het, said alkyl, cycloalkyl, cycloalkenyl, bicycloalkyl, bicycloalkenyl, aryl, Het, alkyl-aryl and alkyl-Het being optionally substituted with from 1 to 4 substituents selected from: halogen, or a) ($C_{1-6}$)alkyl optionally substituted with:
   $OR^{21}$ or $SR^{21}$ wherein $R^{21}$ is H, ($C_{1-6}$alkyl), ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or
   $N(R^{22})_2$ wherein each $R^{22}$ is independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or both $R^{22}$ are covalently bonded together and to the nitrogen to which they are attached to form a 5, 6 or 7-membered saturated heterocycle;

b) $OR^{23}$ wherein $R^{23}$ is H, ($C_{1-6}$)alkyl, ($C_{3-7}$) cycloalkyl or ($C_{1-6}$)alkyl-($C_{3-7}$)cycloalkyl, aryl, Het, ($C_{1-6}$)alkyl-aryl or ($C_{1-6}$)alkyl-Het;

c) $SR^{24}$ wherein $R^{24}$ is H, ($C_{1-6}$)alkyl, ($C_{3-7}$) cycloalkyl, or ($C_{1-6}$)alkyl-($C_{3-7}$)cycloalkyl, aryl, Het, ($C_{1-6}$)alkyl-aryl or ($C_{1-6}$)alkyl-Het; and d) $N(R^{25})_2$ wherein each $R^{25}$ is independently H, ($C_{1-6}$ alkyl, ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or both $R^{25}$ are covalently bonded together and to the nitrogen to which they are attached to form a 5, 6 or 7-membered saturated heterocycle;

B is $CR^6$, wherein $R^5$ is H, halogen, ($C_{1-6}$)alkyl, haloalkyl, ($C_{3-7}$)cycloalkyl or ($C_{1-6}$)alkyl-($C_{3-7}$) cycloalkyl; or $R^5$ is $OR^{51}$ or $SR^{51}$, $COR^{51}$ or $NR^{51}COR^{51}$ wherein each $R^{51}$ is independently H, ($C_{1-6}$alkyl), ($C_{3-7}$)cycloalkyl or ($C_{1-6}$)alkyl-($C_{3-7}$) cycloalkyl;

or $R^5$ is $NR^{52}R^{53}$ wherein $R^{52}$ and $R^{53}$ are each independently H, ($C_{1-6}$)alkyl, ($C_{3-7}$)cycloalkyl, ($C_{1-6}$)alkyl-($C_{3-7}$)cycloalkyl, or both $R^{52}$ and $R^{53}$ are covalently bonded together and to the nitrogen to which they are attached to form a 5, 6 or 7-membered saturated heterocycle;

X is $CR^5$, wherein $R^5$ is as defined above;

D is $CR^5$, wherein $R^5$ is as defined above;

each of $Y^1$ and $Y^2$ is independently O or S;

Z is O, N, or $NR^6$ wherein $R^6$ is H, ($C_{1-6}$)alkyl, ($C_{3-7}$) cycloalkyl or ($C_{1-6}$)alkyl-($C_{3-7}$)cycloalkyl;

$R^3$ and $R^4$ are each independently H, ($C_{1-6}$)alkyl, haloalkyl, ($C_{3-7}$)cycloalkyl, 6- or 10-membered aryl, Het, ($C_{1-6}$)alkyl-aryl, ($C_{1-6}$)alkyl-Het, wherein said alkyl, cycloalkyl, aryl; Het, ($C_{1-6}$)alkyl-aryl, ($C_{1-6}$) alkyl-Het are optionally substituted with $R^{30}$; or $R^7$ and $R^8$ are covalently bonded together to form second ($C_{3-7}$)cycloalkyl or a 4, 5- or 6-membered heterocycle having from 1 to 3 heteroatom selected from O, N, and S; or when Z is $NR^6$, either of $R^7$ or $R^8$ is covalently bonded to $R^6$ to form a nitrogen-containing 5- or 6-membered heterocycle;

$R^7$ is H, ($C_{1-6}$alkyl), ($C_{3-7}$)cycloalkyl or ($C_{1-6}$)alkyl-($C_{3-7}$)cycloalkyl, aryl, Het, ($C_{1-6}$)alkyl-aryl or ($C_{1-6}$) alkyl-Het, all of which optionally substituted with $R^{70}$; or $R^7$ is covalently bonded to either of $R^3$ or $R^4$ to form a 5- or 6-membered heterocycle;

A is a 6- or 10-membered aryl, Het, ($C_{1-6}$)alkyl-aryl, ($C_{1-6}$)alkyl-Het, ($C_{1-6}$)alkyl-CONH-aryl or ($C_{1-6}$)alkyl-CONH-Het, all of which being optionally substituted with:

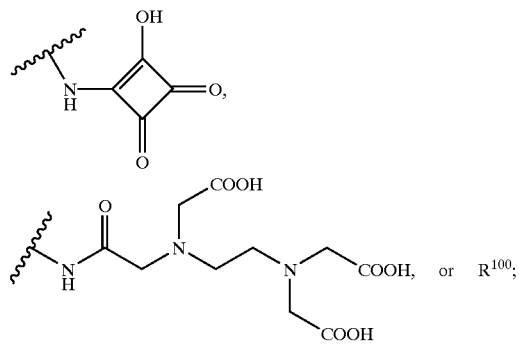

or a salt or a derivative thereof;

wherein Het is defined as:

5- or 6-membered heterocycle having 1 to 4 heteroatoms selected from O, N, and S, or a 9- or 10-membered heterobicycle having 1 to 5 heteroatoms selected from O, N and S; and $R^{10}$, $R^{30}$, $R^{70}$ and $R^{100}$ are defined as:

1 to 4 substituents selected from: halogen, $OPO_3H$, $NO_2$, cyano, azido, $C(=NH)NH_2$, $C(=NH)NH(C_{1-6})$alkyl or $C(=NH)NHCO(C_{1-6})$alkyl; or 1 to 4 substituents selected from:

a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-6})$alkynyl, $(C_{1-6})$alkyl-$(C_{3-7})$cycloalkyl, all of which optionally substituted with $R_{150}$;

b) $OR^{104}$ wherein $R_{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R_{150}$;

c) $OCOR^{105}$ wherein $R^{105}$ is $(C_{1-6})$alkyl, $(C_{3-7})$cycloalkyl, $(C_{1-6})$alkyl-$(C_{3-7}$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SR_{105}$, $SO_2N(R_{105})_2$ or $SO_2N(R^{105})C(O)R^{105}$ wherein each $R^{105}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{105}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R_{112}$ wherein $R^{111}$ is H, $(C_{1-6}$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R_{112}$ is H, CN, $(C_{1-6})$alkyl, $(C_{3-7})$cycloalkyl or $(C_{1-6}$alkyl-$(C_{3-7})$cycloalkyl, aryl, Het, $(C_{1-6}$alkyl)aryl, $(C_{1-6}$alkyl)Het, $COOR^{115}$ or $SO_2R_{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{150}$;

g) $NR^{118}CONR_{119}R^{120}$, wherein $R_{118}$, $R^{119}$ and $R_{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle;

or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R^{122}$ is each H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R_{150}$;

or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or$(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is H, $(C_{1-6})$alkyl, $(C_{3-7})$cycloalkyl, or$(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, or$(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;

l) aryl, Het, $(C_{1-6}$alkyl)aryl or $(C_{1-6}$alkyl)Het, all of which being optionally substituted with $R^{150}$; and wherein $R^{160}$ is defined as:

1 to 3 substituents selected from: halogen, $OPO_3H$, $NO_2$, cyano, azido, $C(=NH)NH_2$, $C(=NH)NH(C_{1-6})$alkyl or $C(=NH)NHCO(C_{1-6})$alkyl; or 1 to 3 substituents selected from:

a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8}$alkynyl, $(C_{1-6})$alkyl-$(C_{3-7})$cycloalkyl, all of which optionally substituted with $R^{160}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{160}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{160}$;

d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{160}$;

e) NR$^{111}$R$^{112}$ wherein R$^{111}$ is H, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het, and R$^{112}$ is H, CN, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl, (C$_{1-6}$alkyl)Het, COOR$^{115}$ or SO$_2$R$^{115}$ wherein R$^{115}$ is (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or both R$^{111}$ and R$^{112}$ are covalently bonded together and to the nitrogen to which they are attached to form a 5, 6 or 7-membered saturated heterocycle, said alkyl, cycloalkyl, aryl, Het, (C$_{1-6}$alkyl)aryl or (C$_{1-6}$alkyl)Het, or heterocycle being optionally substituted with R$^{160}$;

f) NR$^{116}$COR$^{117}$ wherein R$^{116}$ and R$^{117}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, said (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het being optionally substituted with R$^{160}$;

g) NR$^{118}$CONR$^{119}$R$^{120}$, wherein R$^{118}$, R$^{119}$ and R$^{120}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or R$^{118}$ is covalently bonded to R$^{119}$ and to the nitrogen to which they are attached to form a 5, 6 or 7-membered saturated heterocycle, or R$^{119}$ and R$^{120}$ are covalently bonded together and to the nitrogen to which they are attached to form a 5, 6 or 7-membered saturated heterocycle, said alkyl, cycloalkyl, (C$_{1-6}$alkyl-(C$_{3-7}$)cycloalkyl, aryl, Het, (C$_{1-6}$alkyl)aryl or (C$_{1-6}$alkyl)Het or heterocycle being optionally substituted with R$^{160}$;

h) NR$^{121}$COCOR$^{122}$ wherein R$^{121}$ and R$^{122}$ is each H, (C$_{1-6}$)alkyl, (C$_{3-7}$)cycloalkyl, (C$_{1-6}$)alkyl-(C$_{3-7}$)cycloalkyl, a 6- or 10-membered aryl, Het, (C$_{1-6}$alkyl)aryl or (C$_{1-6}$alkyl)Het, said alkyl, cycloalkyl, alkyl-cycloalkyl, aryl, Het, (C$_{1-6}$alkyl)aryl or (C$_{1-6}$alkyl)Het being optionally substituted with R$^{160}$, or R$^{122}$ is OR$^{123}$ or N(R$^{124}$)$_2$ wherein R$^{123}$ and each R$^{124}$ is independently H, (C$_{1-6}$alkyl), (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or R$^{124}$ is OH or O(C$_{1-6}$alkyl) or both R$^{124}$ are covalently bonded together to form a 5, 6 or 7-membered saturated heterocycle, said alkyl, cycloalkyl, alkyl-cycloalkyl, aryl, Het, (C$_{1-6}$alkyl)aryl or (C$_{1-6}$alkyl)Het and heterocycle being optionally substituted with R$^{160}$;

i) COR$^{127}$ wherein R$^{127}$ is H, (C$_{1-6}$)alkyl, (C$_{3-7}$ cycloalkyl or (C$_{1-6}$)alkyl-(C$_{3-7}$)cycloalkyl, aryl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{160}$;

j) tetrazole, COOR$^{128}$ wherein R$^{128}$ is H, (C$_{1-6}$)alkyl, (C$_{3-7}$cycloalkyl, or(C$_{1-6}$)alkyl-(C$_{3-7}$)cycloalkyl, aryl, Het, (C$_{1-6}$alkyl)aryl or (C$_{1-6}$alkyl)Het, said (C$_{1-6}$)alkyl, (C$_{3-7}$)cycloalkyl, or (C$_{1-6}$)alkyl-(C$_{3-7}$)cycloalkyl; aryl, Het, (C$_{1-6}$alkyl)aryl and (C$_{1-6}$alkyl)Het being optionally substituted with R$^{160}$; and k) CONR$^{129}$R$^{130}$ wherein R$^{129}$ and R$^{130}$ are independently H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or both R$^{129}$ and R$^{130}$ are covalently bonded together and to the nitrogen to which they are attached to form a 5, 6 or 7-membered saturated heterocycle, said alkyl, cycloalkyl, alkyl-cycloalkyl, aryl, Het, (C$_{1-6}$alkyl)aryl, (C$_{1-6}$alkyl)Het and heterocycle being optionally substituted with R$^{160}$;

wherein R$^{106}$ is defined as 1 or 2 substituents selected from: tetrazole, halogen, CN, C$_{1-6}$alkyl, haloalkyl, COOR$^{161}$, SO$_3$H, SR$^{161}$, SO$_2$R$^{161}$, OR$^{161}$, N(R$^{162}$)$_2$, SO$_2$N(R$^{162}$)$_2$, NR$^{162}$COR$^{162}$ or CON(R$^{162}$)$_2$, wherein R$^{161}$ and each R$^{162}$ is independently H, (C$_{1-6}$)alkyl, (C$_{3-7}$)cycloalkyl or (C$_{1-6}$)alkyl-(C$_{3-7}$)cycloalkyl; or both R$^{162}$ are covalently bonded together and to the nitrogen to which they are attached to form a 5, 6 or 7-membered saturated heterocycle;

and with the proviso that when R$^1$ is Het, R$^2$ is (C$_{3-7}$) cycloalkyl, Y$^1$ and Y$^2$ are both O, Z is NH, one of R$^3$ and R$^4$ is optionally substituted (C$_{1-6}$)alkyl-aryl or optionally substituted (C$_{1-6}$)alkyl-Het, and R$^7$ is H, then A is not optionally substituted Het or optionally substituted (C$_{1-6}$)alkyl-Het.

2. A compound according to claim 1, wherein R$^1$ is selected from: (C$_{3-7}$)cycloalkyl, (C$_{5-7}$)cycloalkenyl, 6 or 10-membered aryl, or Het each of which being optionally substituted with 1 or 2 halogen or from 1 or 2 substituents selected from:

a) (C$_{1-6}$)alkyl, (C$_{3-7}$)cycloalkyl, (C$_{2-6}$)alkenyl, each optionally substituted with OR$^{11}$, SR$^{11}$, wherein R$^{11}$ is independently H, (C$_{1-6}$alkyl), (C$_{3-7}$)cycloalkyl, or (C$_{1-6}$)alkyl-(C$_{3-7}$)cycloalkyl;

b) OR$^{13}$ wherein R$^{13}$ is H, (C$_{1-6}$alkyl), (C$_{3-7}$)cycloalkyl, (C$_{1-6}$)alkyl-(C$_{3-7}$)cycloalkyl, a 6- or 10-membered aryl, or Het; and f) a 6- or 10-membered aryl, or Het said aryl or Het being optionally substituted with (C$_{1-6}$)alkyl, (C$_{3-7}$)cycloalkyl or (C$_{1-6}$)alkyl-(C$_{3-7}$)cycloalkyl.

3. A compound according to claim 2, wherein R$^1$ is selected from: 6 or 10-membered aryl, or Het each of which being optionally substituted with 1 or 2 halogen or with 1 or 2 (C$_{1-6}$)alkyl.

4. A compound according to claim 3, wherein R$^1$ is phenyl or Het optionally substituted with (C$_{1-6}$)alkyl.

5. A compound according to claim 4, wherein R$^1$ is selected from:

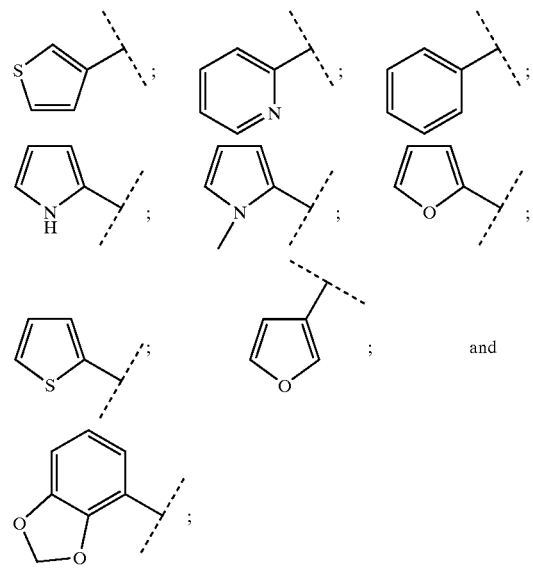

6. A compound according to claim 5, wherein R$^1$ is selected from:

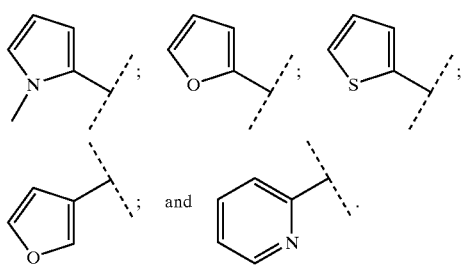

7. A compound according to claim 1, wherein $R^2$ is selected from $(C_{3-7})$cycloalkyl, $(C_{6-10})$bicycloalkyl, each optionally substituted with 1 or 2 substituents selected from:
   a) halogen, $(C_{1-6})$alkyl, OH, or $(C_{1-6})$alkoxy.

8. A compound according to claim 7, wherein $R^2$ is selected from $(C_{3-7})$cycloalkyl, $(C_{6-10})$bicycloalkyl, each optionally mono- or di-substituted with halogen or $(C_{1-6})$alkyl.

9. A compound according to claim 8, wherein $R^2$ is selected from $(C_{3-7})$cycloalkyl or $(C_{6-10})$bicycloalkyl.

10. A compound according to claim 9, wherein $R^2$ is cyclopentyl, cyclohexyl, or

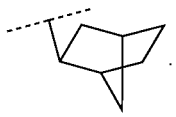

11. A compound according to claim 10, wherein $R^2$ is cyclopentyl or cyclohexyl.

12. A compound according to claim 1, wherein B is $CR^5$, wherein $R^5$ is H, halogen, haloalkyl, or $(C_{1-6})$alkyl.

13. A compound according to claim 12, wherein B is CH or C—$(C_{1-6}$alkyl).

14. A compound according to claim 13, wherein B is CH or C(Me).

15. A compound according to claim 14, wherein B is CH.

16. A compound according to claim 1, wherein X is CH or C—$(C_{1-6}$alkyl).

17. A compound according to claim 16, wherein X is CH or C(Me).

18. A compound according to claim 17, wherein X is CH.

19. A compound according to claim 1, wherein D is $CR^5$, wherein $R^5$ is H, halogen, haloalkyl, or $(C_{1-6})$alkyl.

20. A compound according to claim 19, wherein D is CH or C(Me).

21. A compound according to claim 20, wherein D is CH.

22. A compound according to claim 1 wherein $Y^1$ is O.

23. A compound according to claim 1 wherein $Y^2$ is O.

24. A compound according to claim 1 wherein both $Y^1$ and $Y^2$ are O.

25. A compound according to claim 1, wherein Z is N, or NH or O.

26. A compound according to claim 25, wherein Z is NH or O.

27. A compound according to claim 26, wherein Z is NH.

28. A compound according to claim 1, wherein $R^3$ and $R^4$ are each independently H, $(C_{1-6})$alkyl, first $(C_{3-7})$cycloalkyl, 6- or 10-membered aryl, Het $(C_{1-6})$alkyl-6- or 10-membered aryl, $(C_{1-6})$alkyl-Het;

or $R^3$ and $R^4$ are independently covalently bonded together to form second $(C_{3-7})$cycloalkyl, 5- or 6-membered heterocycle having from 1 to 4 heteroatom selected from O, N, and S;

wherein said alkyl, first and second cycloalkyl, aryl, Het, $(C_{1-6})$alkyl-aryl, $(C_{1-6})$alkyl-Het or heterocycle are optionally substituted with from 1 or 2 substituents selected from:
   a) $(C_{1-6})$alkyl, $(C_{3-7})$cycloalkyl or $(C_{2-4})$alkenyl; and
   c) $OR^{31}$ or $COOR^{31}$, wherein each $R^{31}$ is independently H or $(C_{1-6})$alkyl;

or when Z is N, either $R^3$ or $R^4$ are independently covalently bonded thereto to form a nitrogen-containing 5- or 6-membered heterocycle.

29. A compound according to claim 28, wherein $R^3$ and $R^4$ are each independently H, $(C_{1-6})$alkyl, $(C_{3-7})$cycloalkyl, aryl, Het, $(C_{1-6})$alkyl-aryl or $(C_{1-6})$alkyl-Het; or $R^3$ and $R^4$ are covalently bonded together to form cyclopropyl, cyclobutyl, cyclopentyl or cyclohexyl, 5- or 6-membered heterocycle having from 1 or 2 heteroatom selected from N or S;

wherein said alkyl, cycloalkyl, aryl, Het, $(C_{1-6})$alkyl-aryl, $(C_{1-6})$alkyl-Het cyclopropyl, cyclobutyl, cyclopentyl or cyclohexyl or heterocycle are optionally substituted with from 1 or 2 substituents selected from:
   a) $(C_{1-6})$alkyl, $(C_{3-7})$cycloalkyl, or $(C_{2-4})$alkenyl; and
   c) OH or $COO(C_{1-6})$alkyl.

30. A compound according to claim 29, wherein $R^3$ and $R^4$ are each independently H, $(C_{1-6})$alkyl, $(C_{3-7})$cycloalkyl, $(C_{1-6})$alkyl-$(C_{3-7})$cycloalkyl, aryl, Het, $(C_{1-6})$alkyl-phenyl, $(C_{1-6})$alkyl-Het;

or $R^3$ and $R^4$ are covalently bonded together to form cyclopropyl, cyclobutyl, cyclopentyl or cyclohexyl all optionally substituted with OH, $(C_{1-6}$alkyl) or $(C_{2-4})$ alkenyl; or $R^3$ and $R^4$ form a piperidine or a pyrrolidine both optionally substituted with $(C_{1-6}$alkyl) or COO $(C_{1-6})$alkyl.

31. A compound according to claim 30, wherein $R^3$ is H or $(C_{1-6})$alkyl and $R^4$ is H, $(C_{1-6})$alkyl, $(C_{3-7})$cycloalkyl, $(C_{1-6})$alkyl-aryl, aryl, $(C_{1-6})$alkyl-$(C_{3-7})$cycloalkyl, or $(C_{1-6})$alkyl-biaryl.

32. A compound according to claim 31, wherein both $R^3$ and $R^4$ are H or both $CH_3$;

or $R^3$ is H and $R^4$ is selected from:

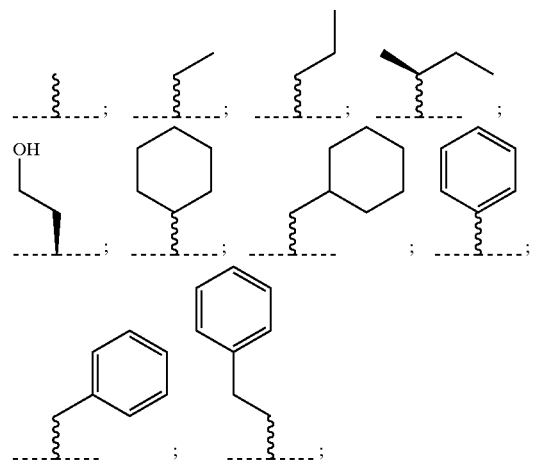

-continued

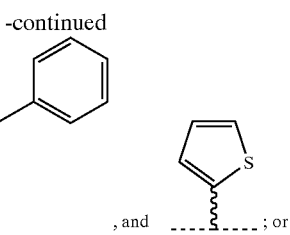

R³ and R⁴ are bonded together and form:

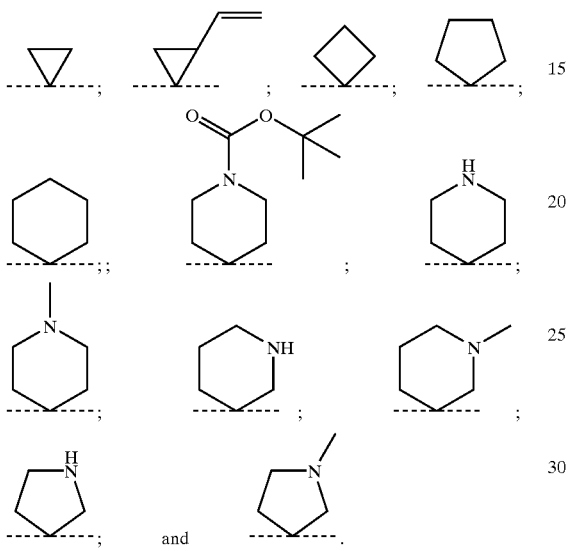

33. A compound according to claim 1, wherein R⁷ is H or ($C_{1-6}$alkyl).

34. A compound according to claim 33, wherein R⁷ is H or Me.

35. A compound according to claim 34, wherein R⁷ is H.

36. A compound according to claim 1, wherein A is a 6- or 10-membered aryl, Het or ($C_{1-6}$)alkyl-CONH-aryl, said aryl or Het being optionally substituted with:

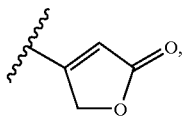

halogen, or
1 to 2 substituents selected from:
  a) ($C_{1-6}$)alkyl, ($C_{1-6}$) haloalkyl, ($C_{3-7}$)cycloalkyl, ($C_{2-6}$) alkenyl, ($C_{2-6}$)alkynyl, all of which are optionally substituted with:
    ($C_{1-6}$)alkyl, ($C_{3-7}$)cycloalkyl; both optionally substituted with a 6 or 10-membered aryl, or Het;
    $OR^{101}$, $COOR^{101}$ or $CON(R^{101})_2$, wherein each $R^{101}$ is independently H or ($C_{1-6}$)alkyl;
  b) $OR^{104}$ wherein $R^{104}$ is H or ($C_{1-6}$alkyl) optionally substituted with: $COOR^{105}$ or $CON(R^{105})_2$ wherein each $R^{105}$ is independently H or ($C_{1-6}$)alkyl;
  d) $SR^{108}$ wherein $R^{108}$ is H or ($C_{1-6}$)alkyl optionally substituted with $COOR^{109}$ or $CON(R^{109})_2$, wherein each $R_{109}$ is independently H or ($C_{1-6}$)alkyl;
  e) $NR^{111}R^{112}$ wherein $R^{111}$ and $R^{112}$ are both H; or $R^{111}$ is H and $R^{112}$ is Het optionally substituted with ($C_{1-6}$)alkyl or $COOR^{115}$ or $CON(R^{115})_2$, wherein each $R^{115}$ is independently H, ($C_{1-6}$)alkyl, ($C_{3-7}$)cycloalkyl, or ($C_{1-6}$)alkyl-($C_{3-7}$)cycloalkyl;
  j) tetrazole, COOH or $COO(C_{1-6})$alkyl; and
  k) $CONR^{129}R^{130}$ wherein $R^{129}$ and $R^{130}$ are each independently H or ($C_{1-6}$)alkyl optionally substituted with COOH or $COO(C_{1-6})$alkyl; and
  l) 6- or 10-membered aryl or Het, said aryl or Het being optionally substituted with from 1 to 4 substituents selected from:
    i) ($C_{1-6}$)alkyl or haloalkyl;
    ii) $OR^{104}$, wherein $R^{104}$ is H, or ($C_{1-6}$)alkyl) optionally substituted with COOH or $COO(C_{1-6})$alkyl; and
    iii) $COOR^{128}$, $NR^{111}R^{112}$ or $CON(R^{129}R^{130})_2$, wherein $R^{128}$, $R^{111}$, $R^{112}$, $R^{129}$ and $R^{130}$ are independently H or ($C_{1-6}$)alkyl.

37. A compound according to claim 36, wherein A is a 6- or 10-membered aryl, or Het, said aryl or Het being optionally substituted with:

halogen, or 1 to 2 substituents selected from:
  a) ($C_{1-6}$)alkyl, ($C_{2-6}$)alkenyl, ($C_{2-8}$)alkynyl, said alkyl and alkenyl being optionally substituted with:
    OH, ($C_{1-6}$)alkoxy, COOH or $CONH_2$;
  b) OH, $O(C_{1-6}$alkyl)COOH or $O(C_{1-6}$alkyl)$CONH_2$;
  d) SH, $S(C_{1-6})$alkylCOOH or $S(C_{1-6})$alkylCONH₂;
  j) tetrazole, COOH or $CONH_2$; and
  l) furan or thiazole mono or di-substituted with:
    i) ($C_{1-6}$)alkyl; or
    iii) COOH or $CONH_2$.

38. A compound according to claim 37, wherein A is phenyl, indole, benzofuran, benzothiophene, coumarin or quinolone, all of which optionally substituted with:

iodine, or 1 to 2 substituents selected from:
  a) ($C_{1-6}$)alkyl, ($C_{2-6}$)alkenyl, ($C_{2-8}$)alkynyl, said alkyl and alkenyl being optionally substituted with:
    OH, ($C_{1-6}$)alkoxy, COOH or $CONH_2$;
  b) OH, $O(C_{1-6}$alkyl)COOH or $O(C_{1-6}$alkyl)$CONH_2$;
  d) SH, $S(C_{1-6})$alkylCOOH or $S(C_{1-6})$alkylCONH₂;
  j) COOH or $CONH_2$; and
  l) furan or thiazole mono or di-substituted with:
    i) ($C_{1-6}$)alkyl; or
    iii) COOH or $CONH_2$.

39. A compound according to claim 38, wherein A is selected from:

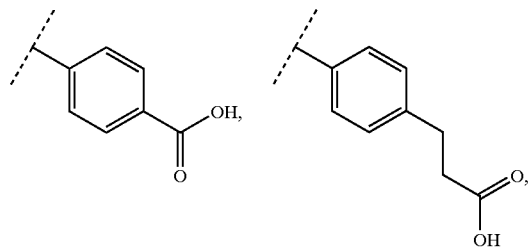

139
-continued
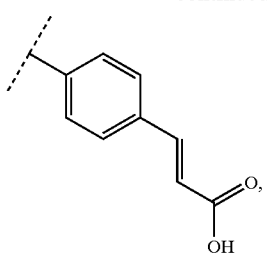
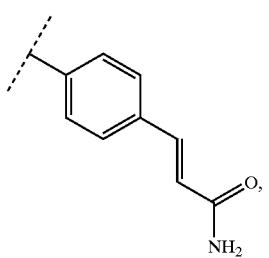
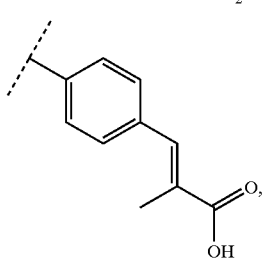
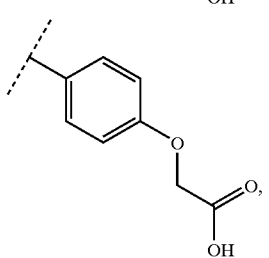
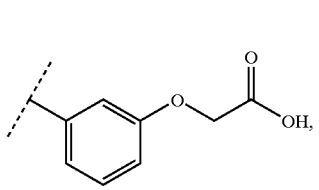
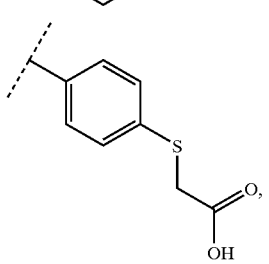
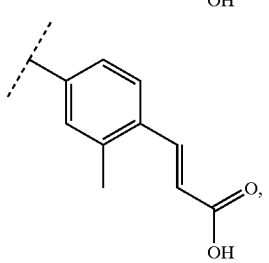
140
-continued
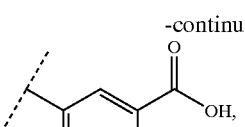
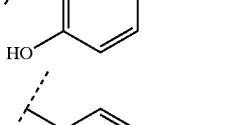
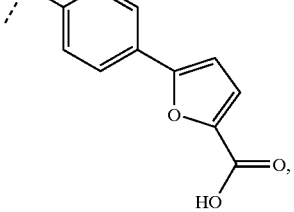
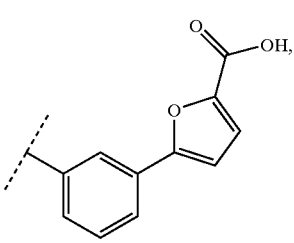
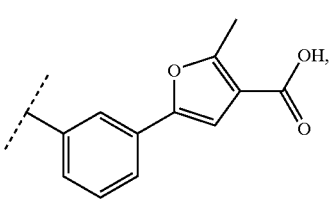
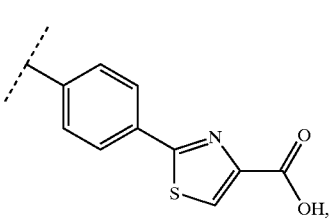
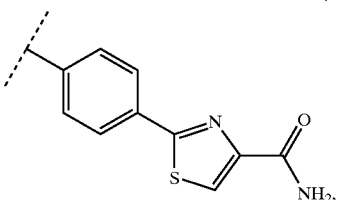
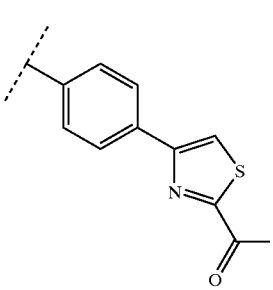

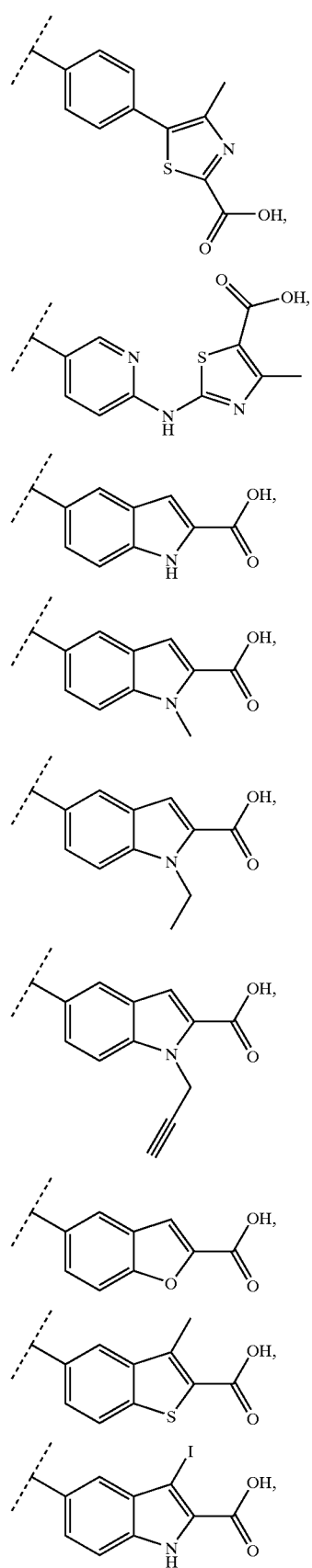
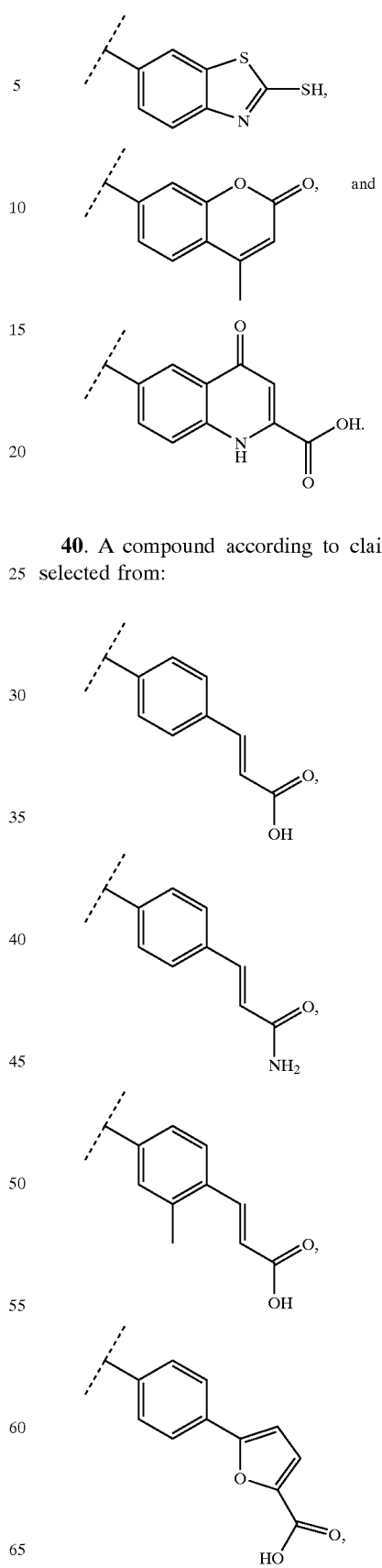
40. A compound according to claim 39, wherein A is selected from:

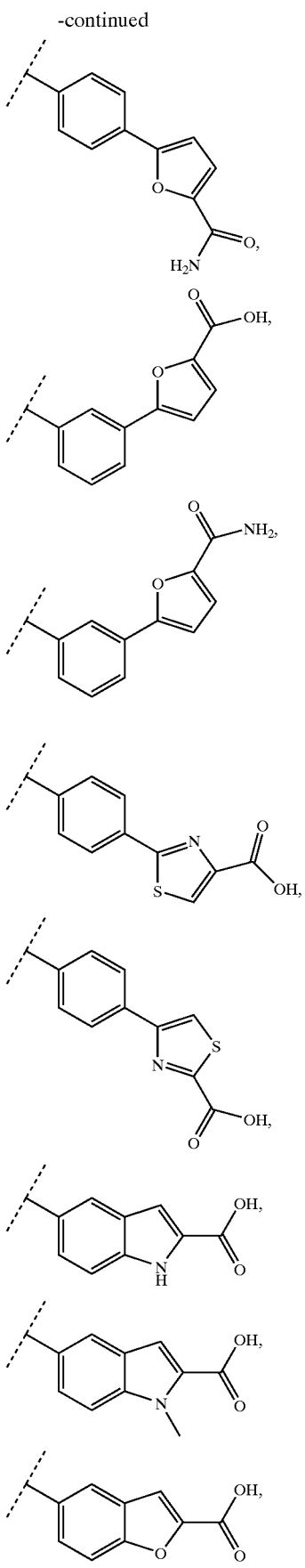

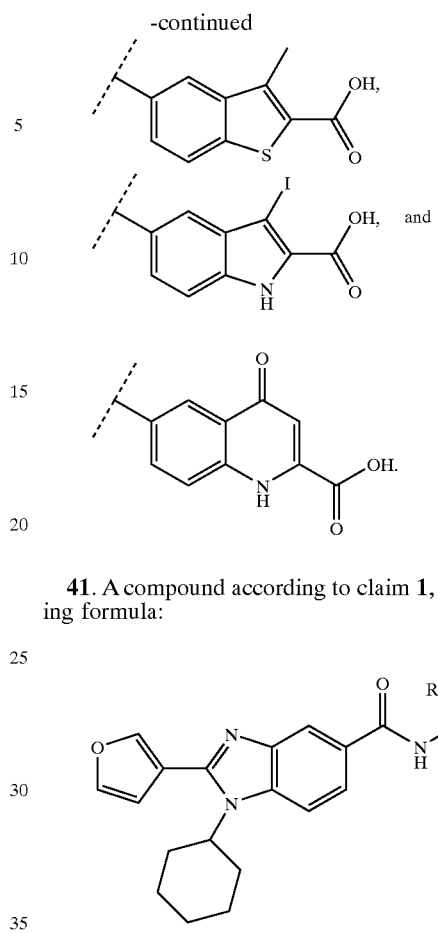

41. A compound according to claim 1, having the following formula:

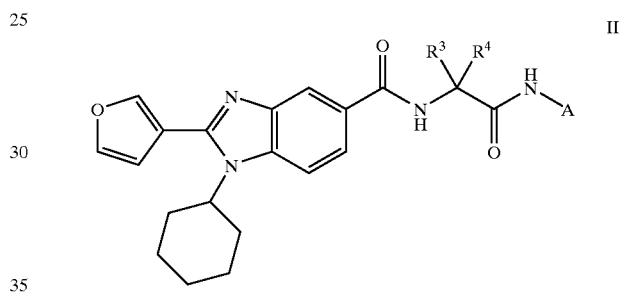

wherein $R^3$ and $R^4$ are each independently H, $(C_{1-6})$alkyl, first $(C_{3-7})$cycloalkyl, 6- or 10-membered aryl, Het, $(C_{1-6})$alkyl-6- or 10-membered aryl, $(C_{1-6})$alkyl-Het;

or $R^3$ and $R^4$ are independently covalently bonded together to form second $(C_{3-7})$cycloalkyl, 5- or 6-membered heterocycle having from 1 to 4 heteroatom selected from O, N, and S;

wherein said alkyl, first and second cycloalkyl, aryl, Het, $(C_{1-6})$alkyl-aryl, $(C_{1-6})$alkyl-Het or heterocycle are optionally substituted with from 1 or 2 substituents selected from:
  a) $(C_{1-6})$alkyl, $(C_{3-7})$cycloalkyl or $(C_{2-4})$alkenyl; and
  c) $OR^{101}$ or $COOR^{101}$, wherein each $R^{101}$ is independently H or $(C_{1-6})$alkyl; and A is a 6- or 10-membered aryl, Het or $(C_{1-6})$alkyl-CONH-aryl, said aryl or Het being optionally substituted with:

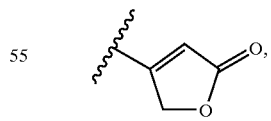

halogen, or
  1 to 2 substituents selected from:
    a) $(C_{1-6})$alkyl, haloalkyl, $(C_{3-7})$cycloalkyl, $(C_{2-6})$alkenyl, $(C_{2-8})$alkynyl, all of which are optionally substituted with:
      second $(C_{1-6})$alkyl, second $(C_{3-7})$cycloalkyl; said second alkyl or second cycloalkyl being optionally substituted with a 6 or 10-membered aryl, or Het;

OR$^{101}$, COOR$^{101}$ or CON(R$^{101}$)$_2$, wherein each R$^{101}$ is independently H or (C$_{1-6}$)alkyl;

b) OR$^{104}$ wherein R$^{104}$ is H or (C$_{1-6}$alkyl) optionally substituted with: COOH, COO(C$_{1-6}$)alkyl or CONH$_2$;

d) SR$^{108}$ wherein R$^{108}$ is H or (C$_{1-6}$)alkyl optionally substituted with COOH, COO(C$_{1-6}$)alkyl or CONH$_2$;

e) NR$^{111}$R$^{112}$ wherein both R$^{111}$ and R$^{112}$ are H; or R$^{111}$ is H and R$^{112}$ is Het optionally substituted with (C$_{1-6}$)alkyl, COOR$^{115}$ or CON(R$^{115}$)$_2$, wherein each R$^{115}$ is independently H, (C$_{1-6}$)alkyl, (C$_{3-7}$)cycloalkyl, or (C$_{1-6}$)alkyl-(C$_{3-7}$)cycloalkyl;

j) COOH or COO(C$_{1-6}$)alkyl; and k) CONR$^{129}$R$^{130}$ wherein R$^{129}$ and R$^{130}$ are independently H or (C$_{1-6}$)alkyl optionally substituted with COOH or COO(C$_{1-6}$)alkyl; and l) 6- or 10-membered aryl or Het, said aryl or Het being optionally substituted with from 1 to 4 substituents selected from:

i) (C$_{1-6}$)alkyl or haloalkyl;
  ii) OR$^{104}$. wherein R$^{104}$ is H, or (C$_{1-6}$)alkyl optionally substituted with COOH or COO(C$_{1-6}$)alkyl; and
  iii) COOR$^{128}$, NR$^{111}$R$^{112}$ or CON(R$^{129}$R$^{130}$)$_2$, wherein R$^{128}$, R$^{111}$, R$^{112}$, R$^{129}$ and R$^{130}$ are independently H or (C$_{1-6}$)alkyl;

with the proviso that when one of R$^3$ and R$^4$ is optionally substituted (C$_{1-6}$)alkyl-6- or 10-membered aryl or optionally substituted (C$_{1-6}$)alkyl-Het, then A is not optionally substituted Het.

42. A compound according to claim 1, having the following formula:

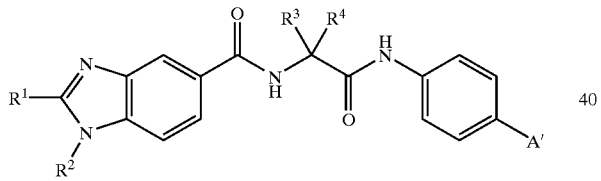

III wherein

R$^1$ is selected from: (C$_{3-7}$)cycloalkyl, (C$_{5-7}$)cycloalkenyl, 6 or 10-membered aryl or Het, each of which being optionally substituted with 1 or 2 halogen or from 1 or 2 substituents selected from:
  a) (C$_{1-6}$)alkyl, (C$_{2-6}$)alkenyl, (C$_{3-7}$)cycloalkyl, each optionally substituted with OR$^{11}$, SR$^{11}$, wherein R$^{11}$ is H, (C$_{1-6}$alkyl), (C$_{3-7}$)cycloalkyl, or (C$_{1-6}$)alkyl-(C$_{3-7}$)cycloalkyl;
  b) OR$^{13}$ wherein R$^{13}$ is H, (C$_{1-6}$alkyl), (C$_{3-7}$) cycloalkyl, (C$_{1-6}$)alkyl-(C$_{3-7}$)cycloalkyl, a 6- or 10-membered aryl, or Het; and
  f) a 6- or 10-membered aryl or Het, said aryl or Het being optionally substituted with (C$_{1-6}$)alkyl, (C$_{3-7}$) cycloalkyl or (C$_{1-6}$)alkyl-(C$_{3-7}$)cycloalkyl;

R$^2$ is selected from (C$_{3-7}$)cycloalkyl, (C$_{6-10}$)bicycloalkyl, each optionally substituted with 1 or 2 substituents selected from: halogen, (C$_{1-6}$)alkyl, OH, and (C$_{1-6}$) alkoxy;

R$^3$ and R$^4$ are each independently H, (C$_{1-6}$)alkyl, first (C$_{3-7}$)cycloalkyl, 6- or 10-membered aryl, Het (C$_{1-6}$) alkyl-6- or 10-membered aryl, (C$_{1-6}$)alkyl-Het;

or R$^3$ and R$^4$ are covalently bonded together to form second (C$_{3-7}$)cycloalkyl, 5- or 6-membered heterocycle having from 1 to 4 heteroatom selected from O, N, and S;

wherein said alkyl, first and second cycloalkyl, aryl, Het, (C$_{1-6}$)alkyl-aryl, (C$_{1-6}$)alkyl-Het or heterocycle are optionally substituted with from 1 or 2 substituents selected from:
  a) (C$_{1-6}$)alkyl, (C$_{3-7}$)cycloalkyl or (C$_{2-4}$)alkenyl; and
  c) OR$^{31}$ or COOR$^{31}$, wherein R$^{31}$ is H or (C$_{1-6}$)alkyl; and A' is a 6- or 10-membered aryl, Het or (C$_{1-6}$)alkyl-CONH-aryl, said aryl or Het being optionally substituted with:

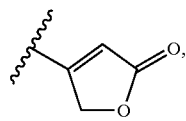

halogen, or 1 to 2 substituents selected from:
  a) (C$_{1-6}$)alkyl, (C$_{1-6}$) haloalkyl, (C$_{3-7}$)cycloalkyl, (C$_{2-6}$)alkenyl, (C$_{2-8}$)alkynyl, all of which are optionally substituted with:
    second (C$_{1-6}$)alkyl or second (C$_{3-7}$)cycloalkyl, said second alkyl or second cycloalkyl being optionally substituted with a 6 or 10-membered aryl or Het; or
    OR$^{101}$,COOR$^{101}$ or CONH$_2$, wherein each R$^{101}$ is independently H or (C$_{1-6}$)alkyl;
  b) OR$^{104}$ wherein R$^{104}$ is H or (C$_{1-6}$alkyl) optionally substituted with: COOH, COO(C$_{1-6}$)alkyl or CONH$_2$;
  d) SR$^{108}$ wherein R$^{108}$ is H or (C$_{1-6}$)alkyl optionally substituted with COOH, COO(C$_{1-6}$)alkyl or CONH$_2$;
  e) NR$^{111}$R$^{112}$ wherein R$^{111}$ and R$^{112}$ are both H; or R$^{111}$ is H and
    R$^{112}$ is Het optionally substituted with (C$_{1-6}$)alkyl, CONH$_2$ or COOR$^{115}$ wherein R$^{115}$ is H, (C$_{1-6}$) alkyl, (C$_{3-7}$)cycloalkyl, or (C$_{1-6}$)alkyl-(C$_{3-7}$) cycloalkyl;
  j) COOH or COO(C$_{1-6}$)alkyl;
  k) CONR$^{129}$R$^{130}$ wherein R$^{129}$ and R$^{130}$ are each independently H or (C$_{1-6}$)alkyl optionally substituted with COOH or COO(C$_{1-6}$)alkyl; and
  l) 6- or 10-membered aryl or Het, said aryl or Het being optionally substituted with from 1 to 4 substituents selected from:
    i) (C$_{1-6}$)alkyl or haloalkyl;
    ii) OR$^{104}$ wherein R$^{104}$ is H, or (C$_{1-6}$)alkyl optionally substituted with COOH or COO(C$_{1-6}$)alkyl; and
    iii) COOR$^{128}$, NR$^{111}$R$^{112}$ or CON(R$^{129}$R$^{130}$)$_2$, wherein R$^{128}$, R$^{111}$, R$^{112}$, R$^{129}$ and R$^{130}$ are independently H or (C$_{1-6}$)alkyl.

43. A compound according to claim 1, having the following formula:

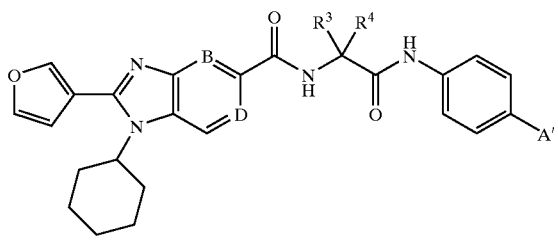

IV wherein
D is CH or C(C$_{1-6}$)alkyl;
B is CH, or C(C$_{1-6}$)alkyl;
R$^3$ and R$^4$ are each independently H, (C$_{1-6}$)alkyl, first (C$_{3-7}$)cycloalkyl, 6- or 10-membered aryl, Het, (C$_{1-6}$)alkyl-6- or 10-membered aryl, (C$_{1-6}$)alkyl-Het;
or R$^3$ and R$^4$ are covalently bonded together to form second (C$_{3-7}$)cycloalkyl, 5- or 6-membered heterocycle having from 1 to 4 heteroatom selected from O, N, and S;
  wherein said alkyl, first and second cycloalkyl, aryl, Het, (C$_{1-6}$)alkyl-aryl, (C$_{1-6}$)alkyl-Het or heterocycle are optionally substituted with from 1 or 2 substituents selected from:
  a) (C$_{1-6}$)alkyl, (C$_{3-7}$)cycloalkyl or (C$_{2-4}$)alkenyl; and
  c) OR$^{31}$ or COOR$^{31}$, wherein R$^{31}$ is H or (C$_{1-6}$)alkyl; and
A' is a 6- or 10-membered aryl, Het or (C$_{1-6}$)alkyl-CONH-aryl, said aryl or Het being optionally substituted with:

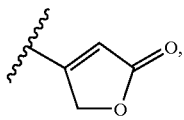

halogen, or
  1 to 2 substituents selected from:
    a) (C$_{1-6}$)alkyl, (C$_{1-6}$) haloalkyl, (C$_{3-7}$)cycloalkyl, (C$_{2-6}$)alkenyl, (C$_{2-8}$)alkynyl, all of which are optionally substituted with:
      second (C$_{1-6}$)alkyl or second (C$_{3-7}$)cycloalkyl, said second alkyl or second cycloalkyl being optionally substituted with a 6 or 10-membered aryl or Het;
      OR$^{101}$, COOR$^{101}$ or CONH$_2$, wherein each R$^{101}$ is independently H or (C$_{1-6}$)alkyl;
    b) OR$^{104}$ wherein R$^{104}$ is H or (C$_{1-6}$alkyl) optionally substituted with: COOH, COO(C$_{1-6}$)alkyl or CONH$_2$;
    d) SR$^{108}$ wherein R$^{108}$ is H or (C$_{1-6}$)alkyl optionally substituted with COOH, COO(C$_{1-6}$)alkyl or CONH$_2$;
    e) NR$^{111}$R$^{112}$ wherein R$^{111}$ and R$^{112}$ are both H; or R$^{111}$ is H and R$^{112}$ is Het optionally substituted with (C$_{1-6}$)alkyl, CONH$_2$ or COOR$^{115}$ wherein R$^{115}$ is H, (C$_{1-6}$)alkyl, (C$_{3-7}$)cycloalkyl, or (C$_{1-6}$)alkyl-(C$_{3-7}$)cycloalkyl;
    j) COOH or COO(C$_{1-6}$)alkyl;
    k) CONR$^{129}$R$^{130}$ wherein R$^{129}$ and R$^{130}$ are each independently H or (C$_{1-6}$)alkyl optionally substituted with COOH or COO(C$_{1-6}$)alkyl; and
    l) 6- or 10-membered aryl or Het, said aryl or Het being optionally substituted with from 1 to 4 substituents selected from:
      i) (C$_{1-6}$)alkyl or haloalkyl;
      ii) OR$^{104}$ wherein R$^{104}$ is H, or (C$_{1-6}$)alkyl) optionally substituted with COOH or COO (C$_{1-6}$)alkyl; and
      iii) COOR$^{128}$, NR$^{111}$R$^{112}$ or CON(R$^{129}$R$^{130}$)$_2$, wherein R$^{128}$, R$^{111}$, R$^{112}$, R$^{129}$ and R$^{130}$ are independently H or (C$_{1-6}$)alkyl.

44. A compound of formula Ia:

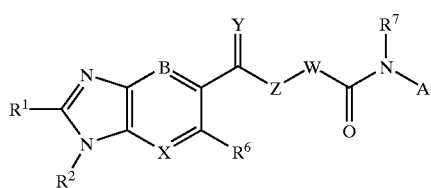

Ia wherein R$^1$ is selected from: 5- or 6-membered heterocycle having 1 to 4 heteroatoms selected from O, N, and S and phenyl, said heterocycle and phenyl being optionally substituted with from 1 to 4 (C$_{1-4}$)alkyl substituents;
R$^2$ is selected from: (C$_{3-7}$)cycloalkyl, (C$_{3-7}$)cycloalkyl (C$_{1-3}$)alkyl, and norbornane;
X is CH;
R$^6$ is H or (C$_{1-6}$alkyl);
Y is O or S;
B is CR$^5$, wherein R$^5$ is H or (C$_{1-6}$)alkyl;
Z is O, N, or NH;
W is CR$^3$R$^4$ wherein R$^3$ and R$^4$ are each independently H, (C$_{1-6}$alkyl), (C$_{3-7}$cycloalkyl), (C$_{1-6}$alkyl)phenyl, (C$_{1-6}$alkyl)-(C$_{3-7}$cycloalkyl), (C$_{3-7}$cycloalkyl)-(C$_{1-6}$alkyl), (C$_{3-7}$cycloalkyl)-(C$_{2-4}$alkenyl), (C$_{1-6}$alkyl)-OH, phenyl; CH$_2$biphenyl, 5- or 6-membered heterocycle having from 1 to 4 heteroatoms selected from O, N, and S, 9- or 10-membered heterobicycle having 1 to 4 heteroatoms selected from O, N, and S, (C$_{1-6}$alkyl)-5- or 6-membered heterocycle having from 1 to 4 heteroatoms selected from O, N, and S, or (C$_{1-6}$alkyl)-9- or 10-membered heterobicycle having 1 to 4 heteroatoms selected from O, N, and S, or R$^3$ and R$^4$ are covalently bonded together to form (C$_{3-7}$cycloalkyl), 4-, 5- or 6-membered heterocycle having from 1 to 4 heteroatoms selected from O, N, and S; or when Z is N, either R$^3$ or R$^4$ is covalently bonded thereto to form a 5-membered heterocycle;
  wherein said alkyl, cycloalkyl, heterocycle, heterobicycle, phenyl are optionally substituted with from 1 to 4 substituents selected from: OH, COOH, (C$_{1-6}$alkyl), (C$_{2-4}$alkenyl), CONH$_2$, NH$_2$, NH(C$_{1-6}$alkyl), N(C$_{1-6}$alkyl)$_2$, NHCOCOOH, NHCOCON (C$_{1-6}$alkyl)$_2$, NHCOCONH(C$_{1-6}$alkyl), SH, S(C$_{1-6}$ alkyl), NHC(=NH)NH$_2$, and COO(C$_{1-6}$alkyl);
R$^7$ is H or (C$_{1-6}$alkyl);
A is selected from: (C$_{1-3}$alkyl)CONHaryl, 6- or 10-membered aryl, biphenyl, 5- or 6-atom heterocycle having 1 to 4 heteroatoms selected from O, N and S, 9- or 10-membered heterobicycle having 1 to 4 heteroatoms selected from O, N and S;
  wherein said aryl, biphenyl, first heterocycle, and heterobicycle are all optionally substituted with from 1 to 4 substituents selected from: OH, COOH, COO (C$_{1-6}$)alkyl, (C$_{1-6}$)alkyl, (C$_{1-6}$)alkylCOOH, (C$_{1-6}$alkyl)(C$_{2-4}$alkynyl), (C$_{1-6}$)alkyl-hydroxy, phenyl, benzyloxy, halogen, (C$_{2-4}$)alkenyl, (C$_{2-4}$)alkenyl-(C$_{1-6}$)alkyl-COOH, 5- or 6-membered second heterocycle having 1 to 4 heteroatoms selected from O, N and S, NH-5- or 6-membered heterocycle having 1 to 4 heteroatoms selected from O, N, and S, wherein said second heterocycle and phenyl being optionally substituted with from 1 to 4 substituents selected from: ($C_{1-6}$alkyl), $CF_3$, OH, ($C_{1-6}$alkyl)COOH, O($C_{1-6}$alkyl)COOH, ($C_{1-6}$alkyl)COO($C_{1-6}$alkyl), $CH_2$phenyl, COO($C_{1-6}$alkyl), ($C_{1-6}$alkyl)O($C_{1-6}$alkyl), COOH, NCH($C_{1-6}$alkyl)$_2$, NCO($C_{1-6}$alkyl), $NH_2$, NH($C_{1-6}$alkyl), and N($C_{1-6}$alkyl)$_2$;

halogen, $OPO_3H$, benzyl, sulfonamido, SH, $SOCH_3$, $SO_3H$, $SO_2CH_3$, S($C_{1-6}$alkyl)COOH, —$CONH_2$, —$COCH_3$, ($C_{1-3}$)alkyl, ($C_{2-4}$alkenyl)COOH wherein said alkenyl is optionally substituted with from 1 to 2 ($C_{1-6}$alkyl) substituents, ($C_{2-4}$alkenyl)COO($C_{1-6}$alkyl), tetrazolyl, COOH, triazolyl, OH, $NO_2$, $NH_2$, —O($CH_2$)$_p$COOH, hydantoin, benzoyleneurea, ($C_{1-4}$)alkoxy, ($C_{1-4}$) alkoxy($C_{1-6}$alkyl)COOH, cyano, azido, —O—($C_{1-6}$) alkyl COOH, —O—($C_{1-6}$)alkyl COO—($C_{1-6}$)alkyl, —NHCOCOOH, —NHCOCONHOH, —NHCOCONH$_2$, —NHCOCONHCH$_3$, —NHCO ($C_{1-6}$)alkyl-COOH, —NHCOCONH($C_{1-6}$)alkyl-COOH, —NHCO($C_{3-7}$)cycloalkyl-COOH, —NHCONH($C_{6-10}$)aryl-COOH, —NHCONH ($C_{6-10}$)aryl-COO($C_{1-6}$)alkyl, —NHCONH($C_{1-6}$) alkyl-COOH, —NHCONH($C_{1-6}$)alkyl-COO($C_{1-6}$) alkyl, —NHCONH($C_{1-6}$)alkyl-($C_{2-6}$)alkenyl-COOH, —NH($C_{1-6}$)alkyl-($C_{6-10}$)aryl-O($C_{1-6}$)alkyl COOH, —NH($C_{1-6}$)alkyl-($C_{6-10}$)aryl-COOH, —NHCH$_2$COOH, —NHCONH$_2$, —NHCO($C_{1-6}$) hydroxyalkyl COOH, —OCO($C_{1-6}$)hydroxyalkyl COOH, ($C_{3-6}$)cycloalkyl COOH,

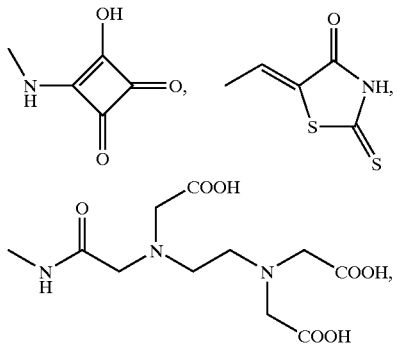

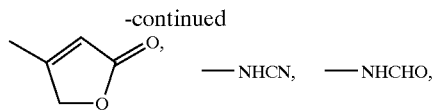

—NHCHO, —NHSO$_2$CH$_3$, —NHSO$_2$CF$_3$, coumarin, ($C_{1-6}$)alkyl-amino, di-($C_{1-6}$)alkyl-amino, C(halogen)$_3$, —NH($C_{2-4}$)acyl, —NH($C_{6-10}$)aroyl, —CONH($C_{1-6}$alkyl), —CO($C_{1-6}$)alkyl-COOH, —CONH($C_{1-6}$)alkyl-COOH, —CO—NH-alanyl, —CONH($C_{2-4}$)alkylN($C_{1-6}$alkyl)$_2$, —CONH($C_{2-4}$)alkyl-Het-CONH($C_{2-4}$)alkyl-(COOH)-Het-CONH($C_{1-2}$alkyl) (OH)($C_{1-2}$alkyl) OH, —CONH($C_{1-6}$) alkyl-COOH, —CONH($C_{6-10}$ aryl), —CONH-Het-CONH ($C_{6-10}$) aryl-COOH, —CONH($C_{6-10}$) aryl-COO($C_{1-6}$)alkyl, —CONH($C_{1-6}$)alkyl-COO($C_{1-6}$)alkyl, —CONH($C_{6-10}$) aryl-($C_{1-6}$)alkyl-COOH, —CONH($C_{6-10}$)aryl-($C_{2-6}$)alkenyl-COOH;

or salt thereof;

with the proviso that when $R^1$ is a 5- or 6-membered heterocycle having 1 to 4 heteroatoms selected from O, N, and S, $R^2$ is ($C_{3-7}$)cycloalkyl, Y is O, Z is NH, one of $R^3$ and $R^4$ is optionally substituted ($C_{1-6}$alkyl)phenyl, optionally substituted CH$_2$biphenyl, optionally substituted ($C_{1-6}$alkyl)-5- or 6-membered heterocycle having from 1 to 4 heteroatoms selected from O, N, and S, or optionally substituted ($C_{1-6}$alkyl)-9- or 10-membered heterobicycle having 1 to 4 heteroatoms selected from O, N, and S, and $R^7$ is H, then A is not optionally substituted 5- or 6-atom heterocycle having 1 to 4 heteroatoms selected from O, N and S or optionally substituted 9- or 10-membered heterobicycle having 1 to 4 heteroatoms selected from O, N and S.

45. A compound according to claim 1 having the following formula:

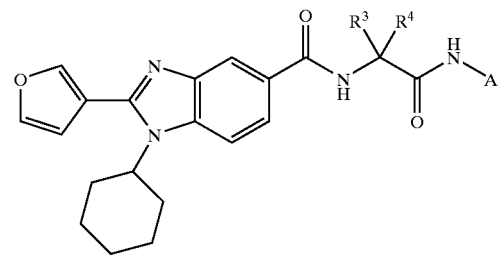

wherein $R^3$, $R^4$ and A are as defined below:

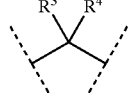

-continued

| Cmpd. # | R³ R⁴ | A |
|---|---|---|
| 1002 | (CH) | 3-(CH=CHCOOH)-phenyl |
| 1003 | (CH) | 4-(CH₂CH₂CH₂COOH)-phenyl |
| 1004 | (CH) | 4-hydroxy-3-(CH₂COOH)-phenyl |
| 1005 | (CHPh) | 4-(CH=CHCOOH)-phenyl |
| 1006 | (CHPh) | 4-(CH=CHCOOH)-phenyl |
| 1007 | (CH) | 3-(CH₂COOH)-phenyl |
| 1008 | (CH) | 4-(CH₂COOH)-phenyl |

-continued

| Cmpd. # | R³ R⁴ | A |
|---|---|---|
| 1009 | | 4-(1-carboxyethyl)phenyl |
| 1010 | | 3-(2-carboxyvinyl)-4-chlorophenyl |
| 1011 | | 3-(1-carboxypropylidenemethyl)phenyl |
| 1012 | | 2-(5-carboxyfuran-2-yl)phenyl |
| 1013 | (S)-sec-butyl | 4-(2-carboxyvinyl)phenyl |
| 1014 | cyclohexylmethyl | 4-(2-carboxyvinyl)phenyl |

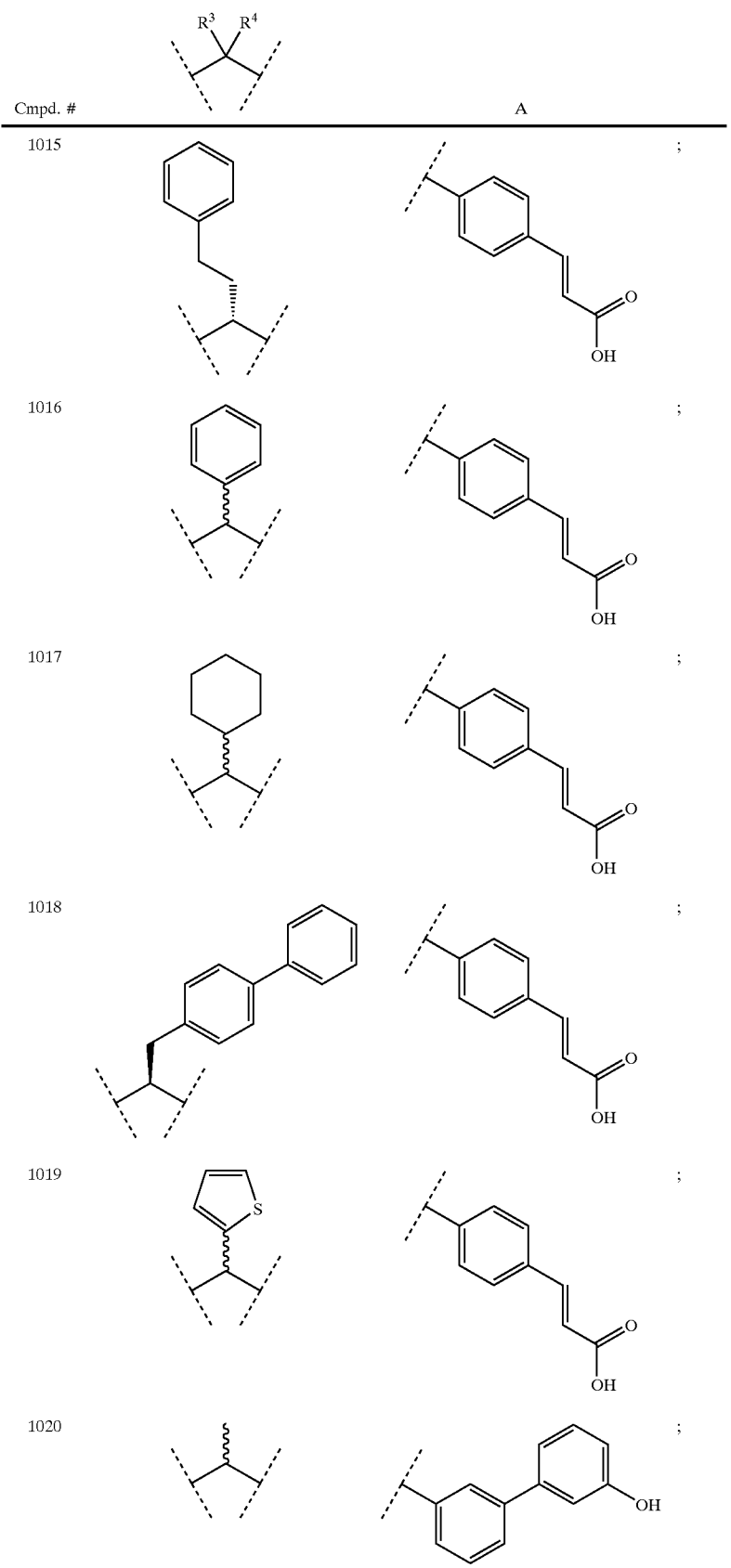

-continued

| Cmpd. # | R³ R⁴ | A |
|---------|-------|---|
| 1021 | | 3-(4-hydroxyphenyl)phenyl |
| 1022 | | 3-(3-aminophenyl)phenyl |
| 1023 | | 2-[4-(carboxymethoxy)phenyl]thiazol-... |
| 1024 | | 4-(2-aminothiazol-4-yl)phenyl |
| 1025 | | 4-[(1-carboxy-1-methylethyl)oxy]phenyl |
| 1026 | | 4-methyl-2-oxo-2H-chromen-7-yl |

US 6,841,566 B2
-continued
| Cmpd. # |  | A |
|---|---|---|
| 1027 | 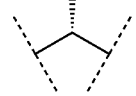 | 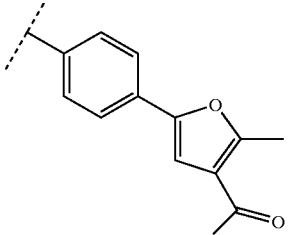 ; |
| 1028 | 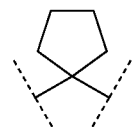 | 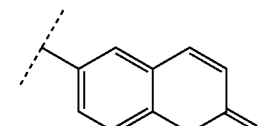 ; |
| 1029 | 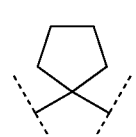 | 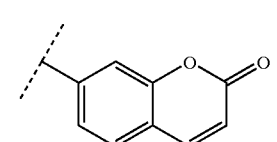 ; |
| 1030 | 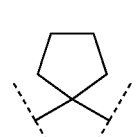 | 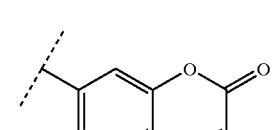 ; |
| 1031 | 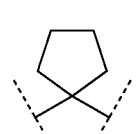 | 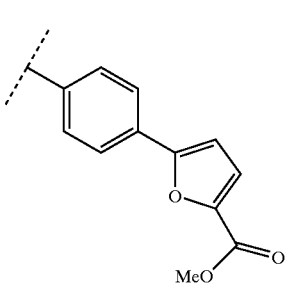 ; |
| 1032 | 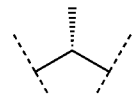 | 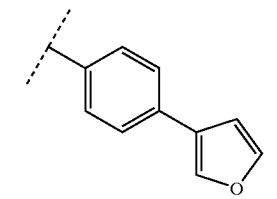 ; |

-continued
| Cmpd. # | R³ R⁴ | A |
|---|---|---|
| 1033 | 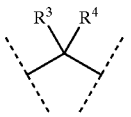 | 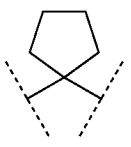 ; |
| 1034 | 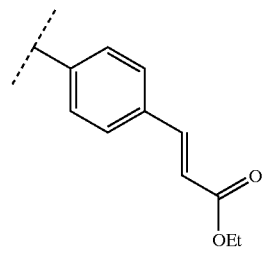 | 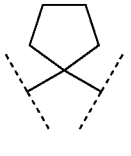 ; |
| 1035 | 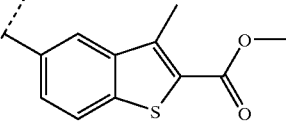 | 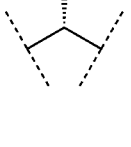 ; |
| 1036 | 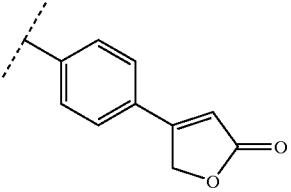 | 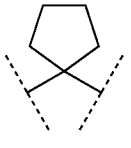 ; |
| 1037 | 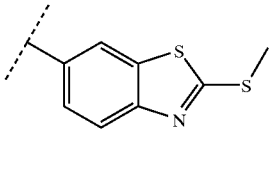 | 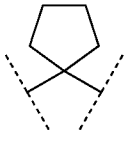 ; |
| 1038 | 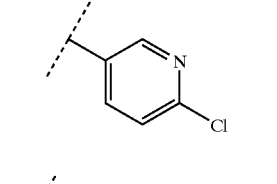 | 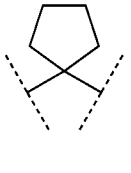 ; |
| 1039 | 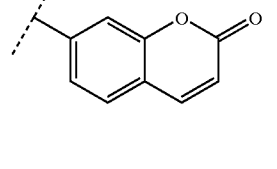 | 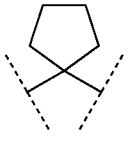 ; |

-continued
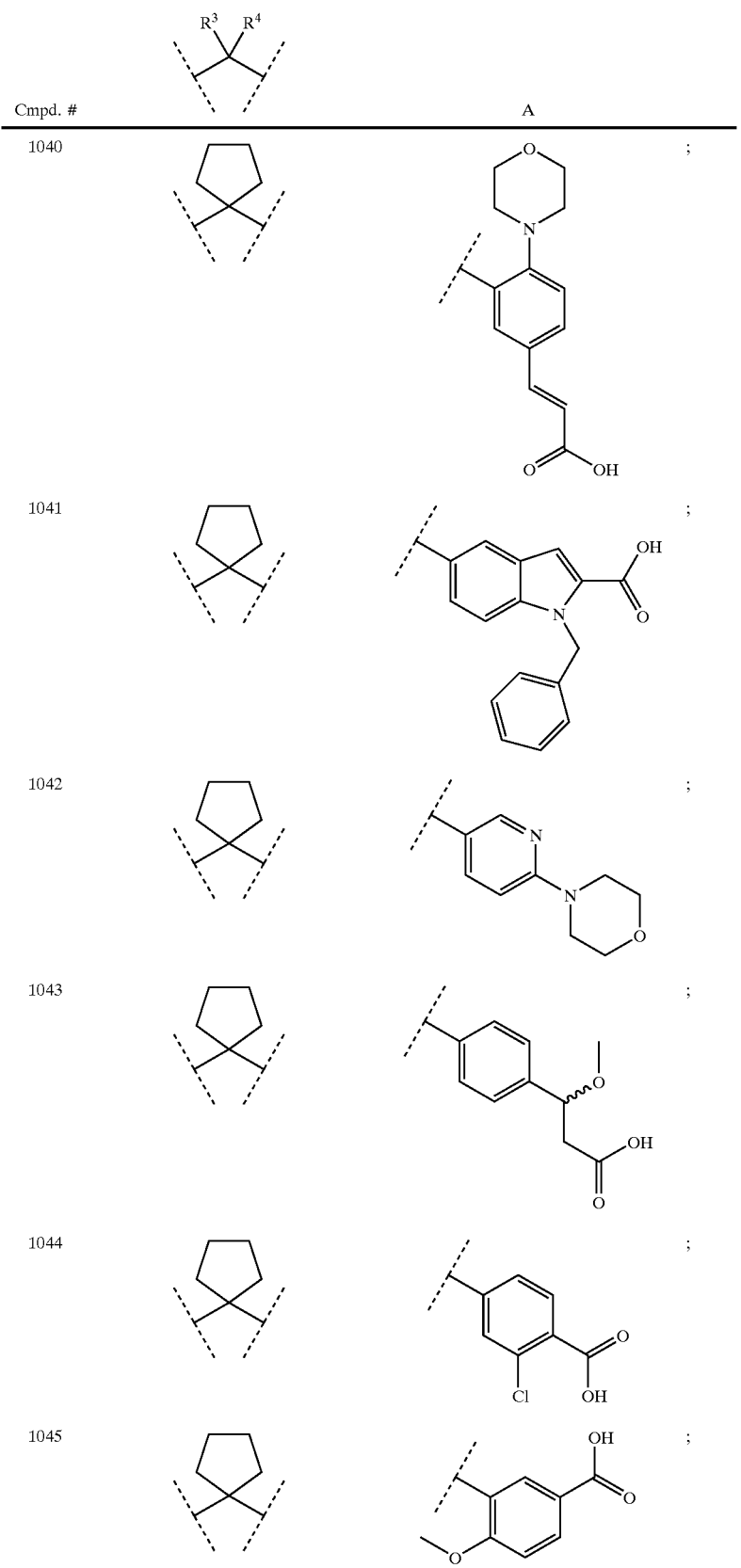

-continued
| Cmpd. # | 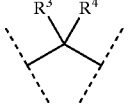 R³ R⁴ | A |
|---|---|---|
| 1046 | 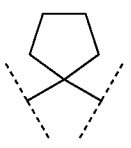 | 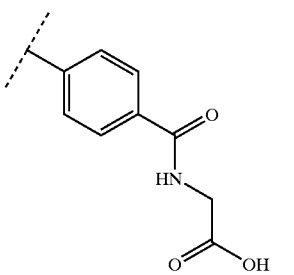 ; |
| 1047 | 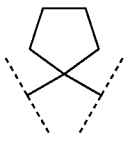 | 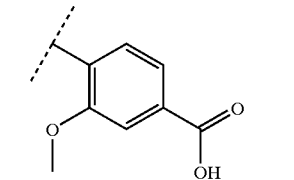 ; |
| 1048 | 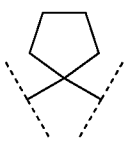 | 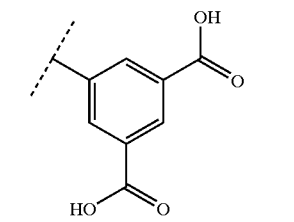 ; |
| 1049 | 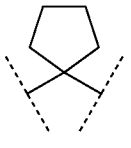 | 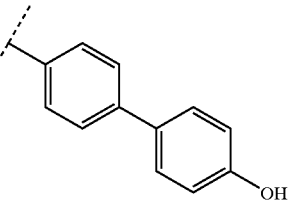 ; |
| 1050 | 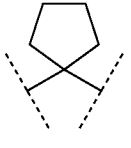 | 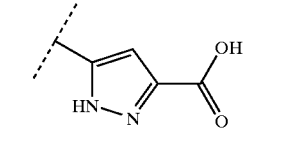 ; |
| 1051 | 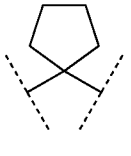 | 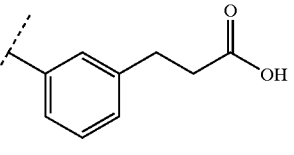 ; |
| 1052 | 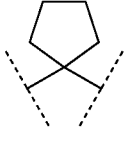 | 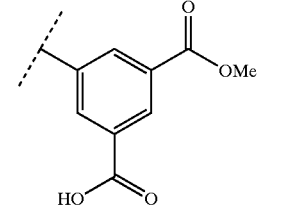 ; |

|Cmpd. #|R³ R⁴|A|
|---|---|---|
|1053|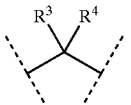|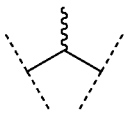;|
|1054|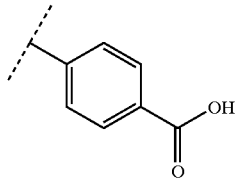|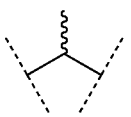;|
|1055|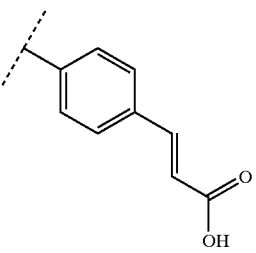|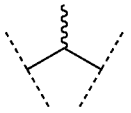;|
|1056|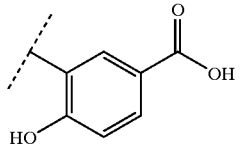|;|
|1057|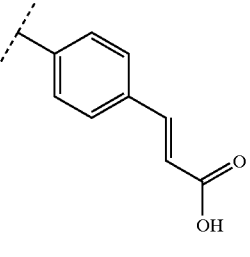|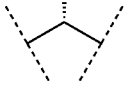;|
|1058|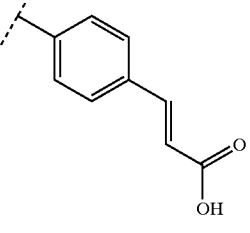|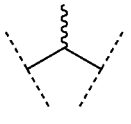;|

-continued
| Cmpd. # | 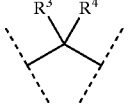 | A |
|---|---|---|
| 1059 | 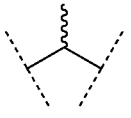 | 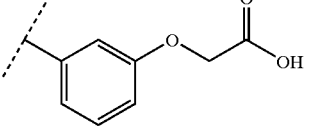 |
| 1060 | 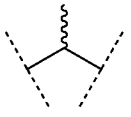 | 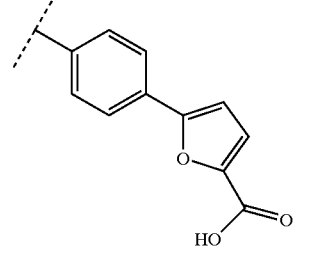 |
| 1061 | 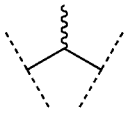 | 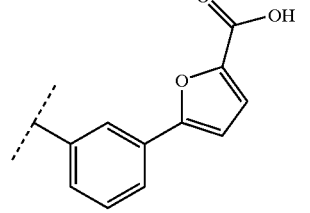 |
| 1062 | 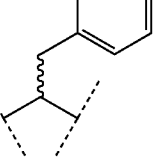 | 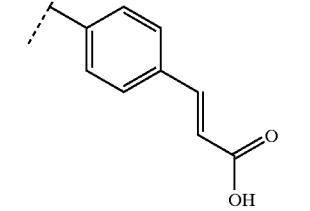 |
| 1063 | 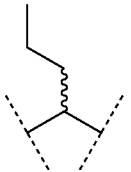 | 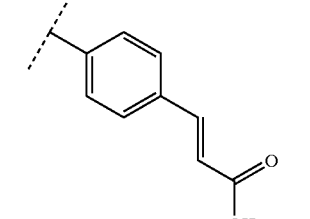 |
| 1064 | 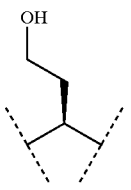 | 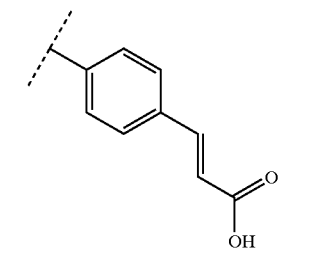 |

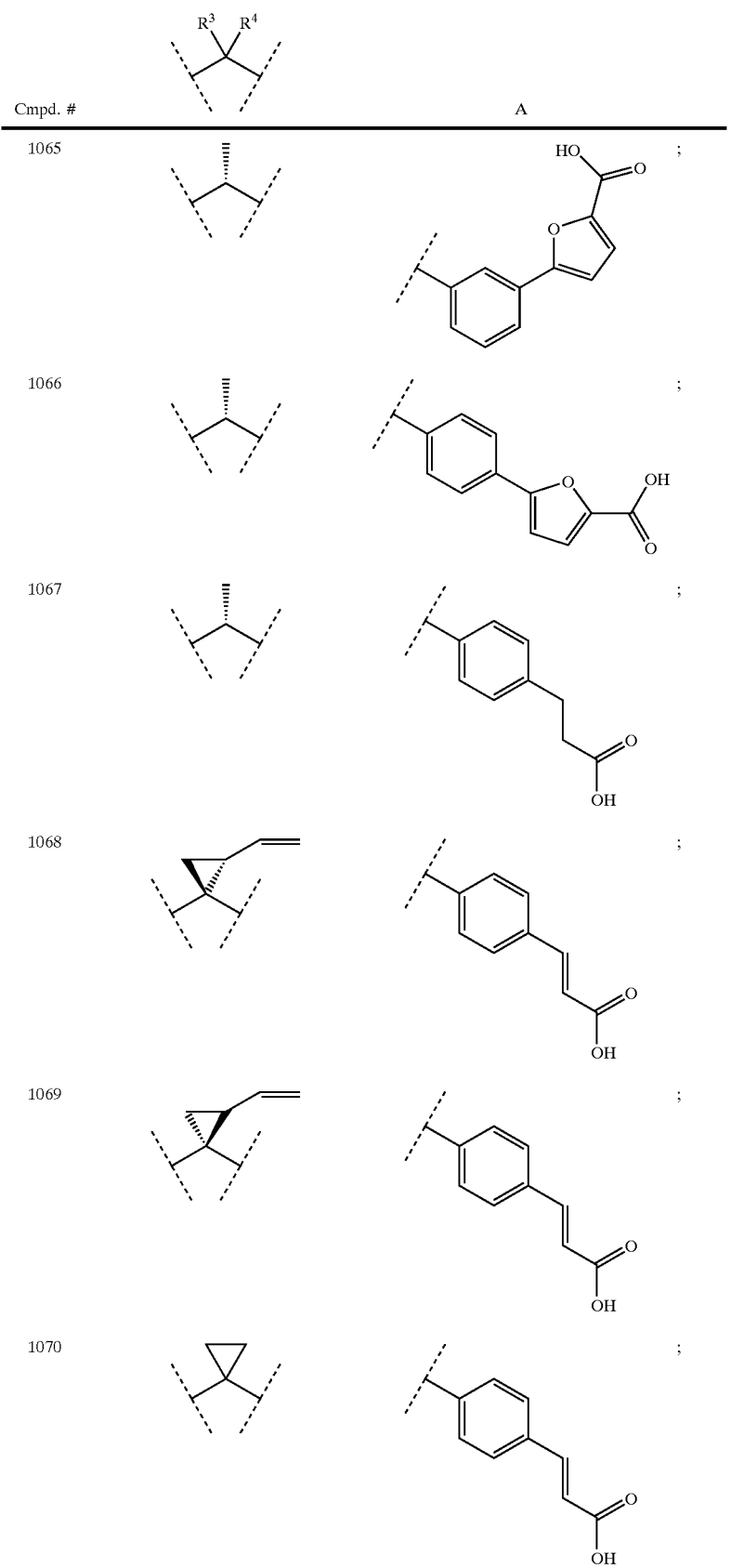

-continued

| Cmpd. # | R³ R⁴ | A |
|---------|-------|---|
| 1071 | cyclopentane spiro | 4-substituted phenyl-CH=CH-COOH |
| 1072 | cyclohexane spiro | 4-substituted phenyl-CH=CH-COOH |
| 1073 | CH (methine) | 4-substituted phenyl-S-CH₂-COOH |
| 1074 | CH (methine) | 3-substituted phenyl-(2-methyl-furan-3-carboxylic acid) |
| 1075 | CH-ethyl | 4-substituted phenyl-CH=CH-COOH |

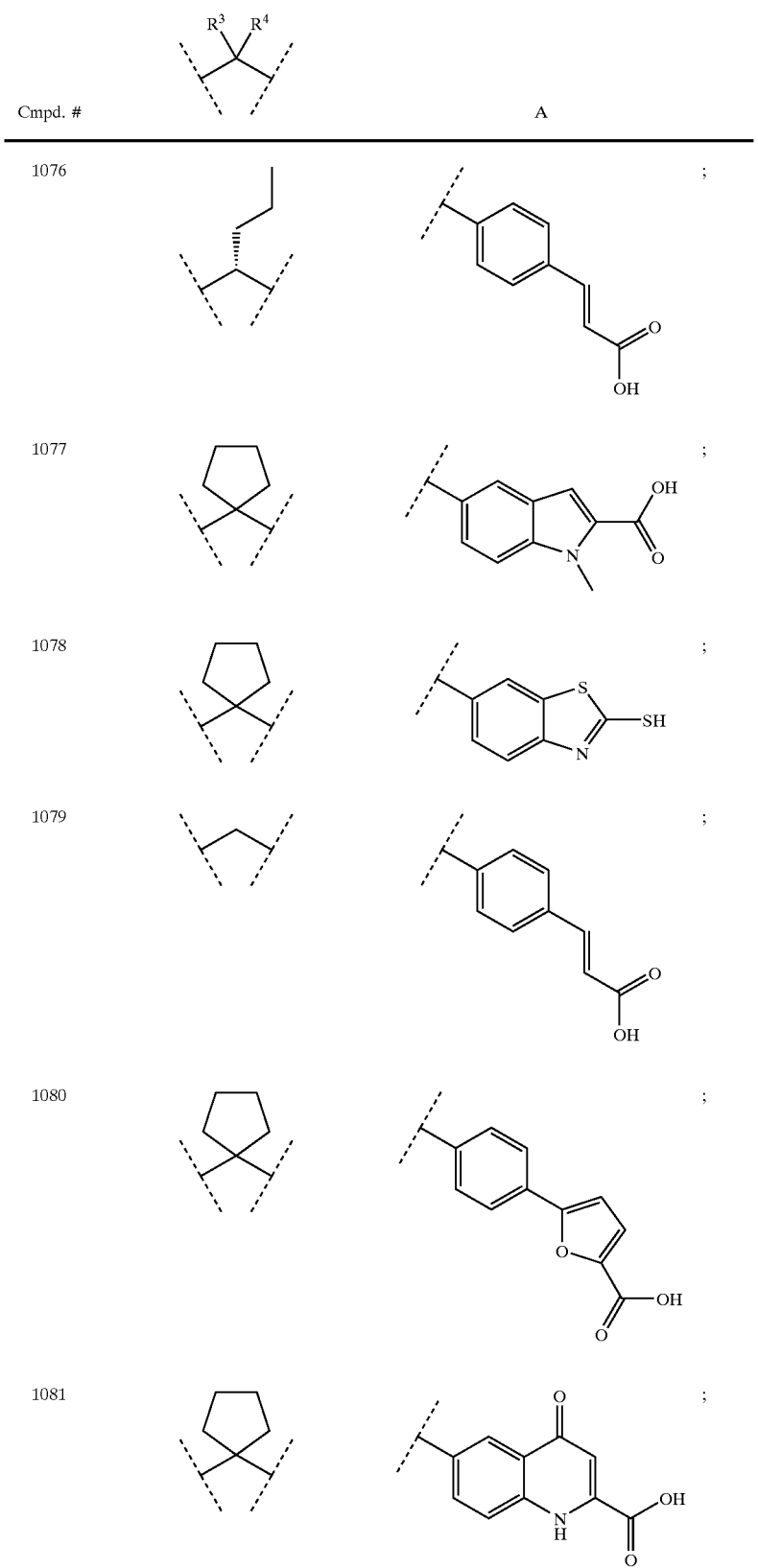

-continued
| Cmpd. # | 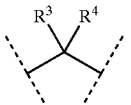 | A |
|---|---|---|
| 1082 | 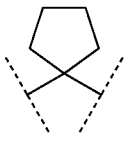 | 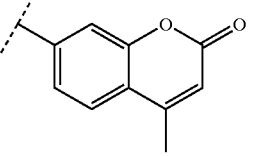 ; |
| 1083 | 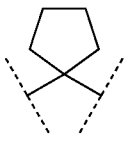 | 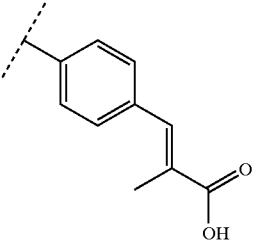 ; |
| 1084 | 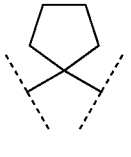 | 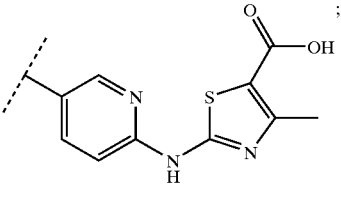 ; |
| 1085 | 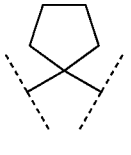 | 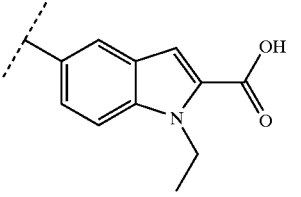 ; |
| 1086 | 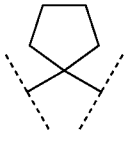 | 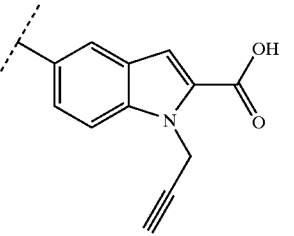 ; |
| 1087 | 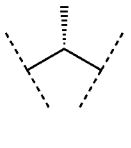 | 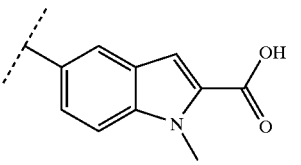 ; |

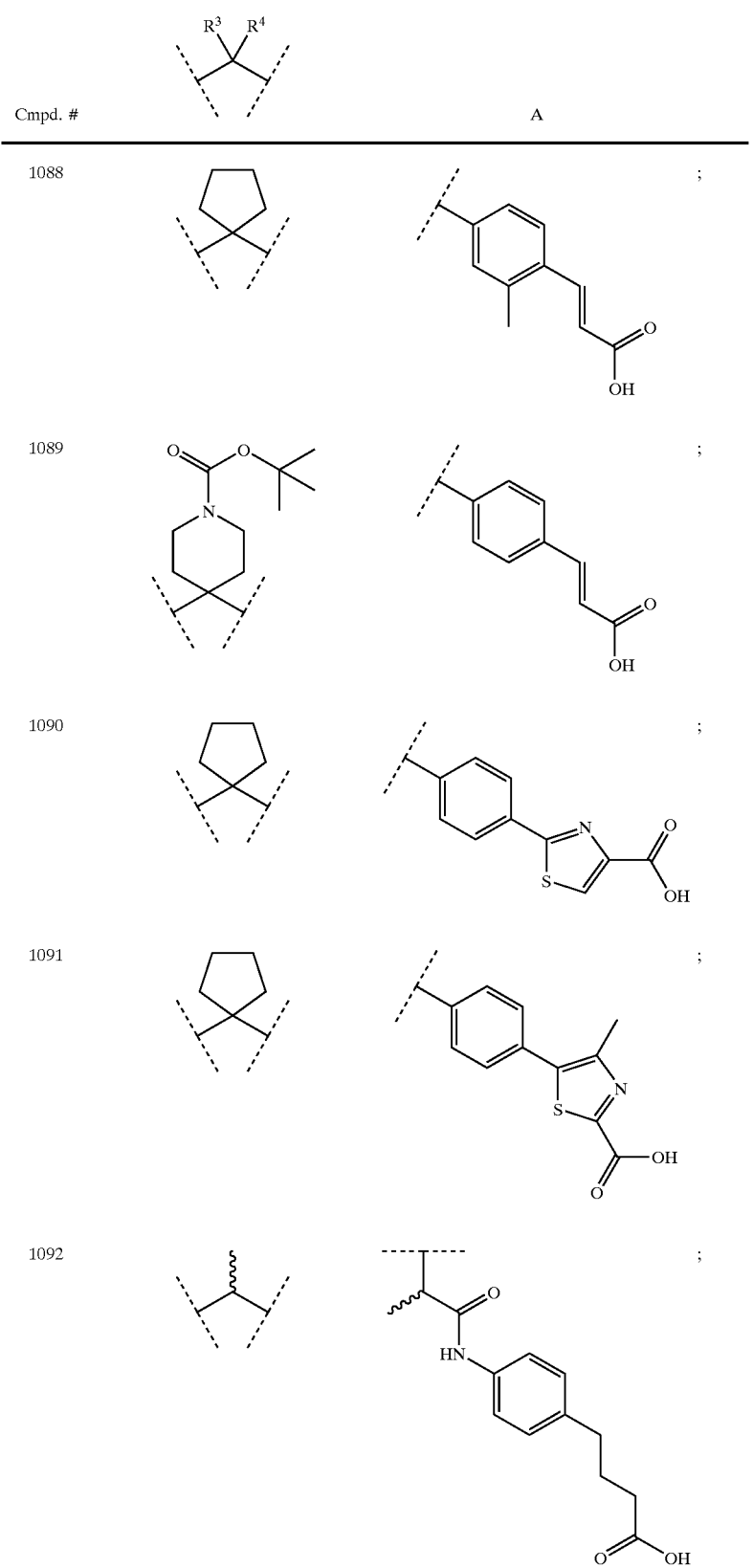

-continued
| Cmpd. # | R³ R⁴ | A |
|---|---|---|
| 1093 | 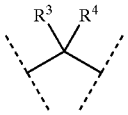 |  ; |
| 1094 | 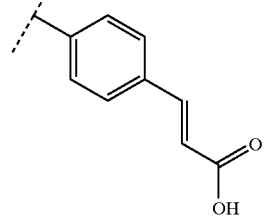 | 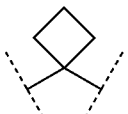 ; |
| 1095 | 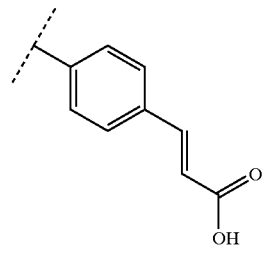 | 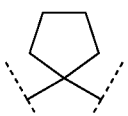 ; |
| 1096 | 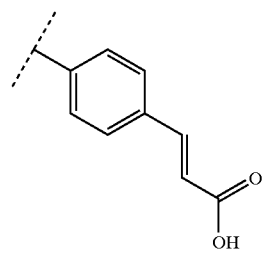 | 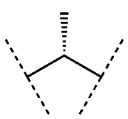 ; |
| 1097 | 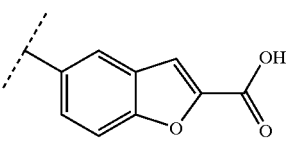 | 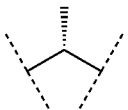 ; |

| Cmpd. # | R³ R⁴ | A |
|---|---|---|
| 1098 | 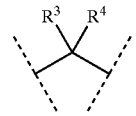 | 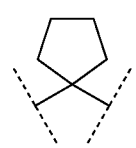 ; |
| 1099 | 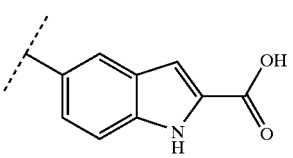 | 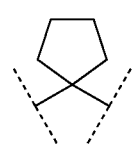 ; |
| 1100 | 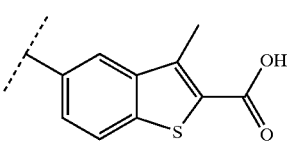 | 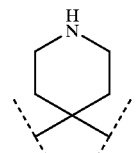 ; |
| 1101 | 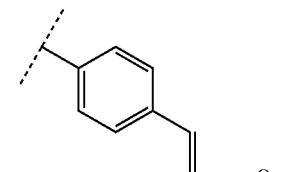 |  ; |
| 1102 | 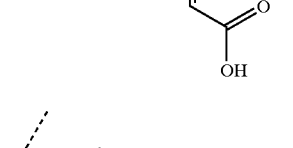 | 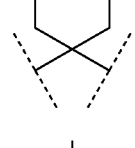 ; |
| 1103 | 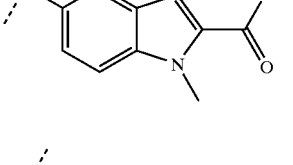 | 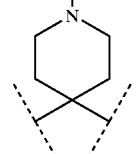 ; |
| 1104 | 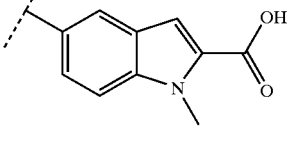<br>(+) enantiomer | 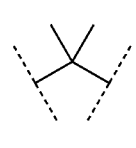 ; |

-continued
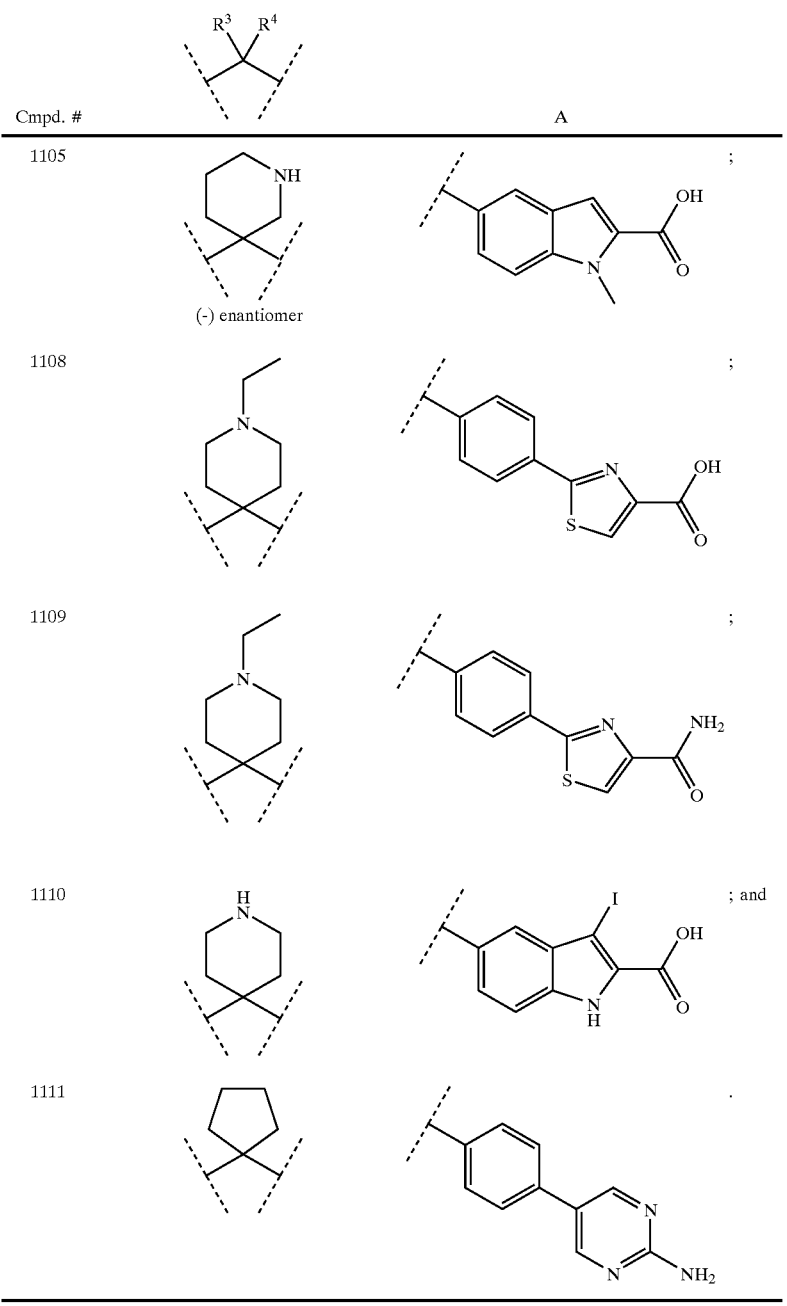
46. A compound according to claim 1 having the following formula:
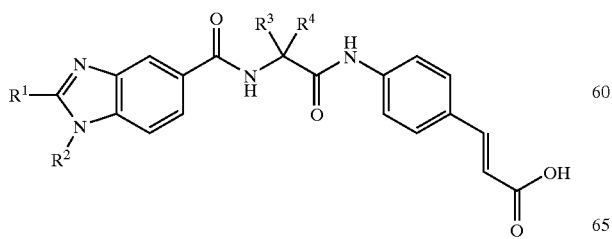
wherein $R^1$, $R^2$, $R^3$, and $R^4$ are as defined below:

| Cmpd. # | R¹ | R² | 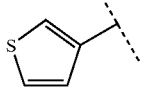 |
|---|---|---|---|
| 2001 | 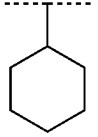 | 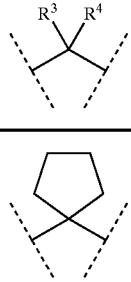 | 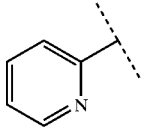 ; |
| 2002 | 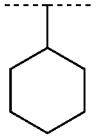 | 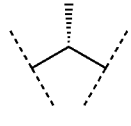 | 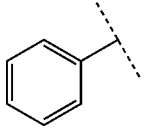 ; |
| 2003 | 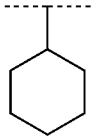 | 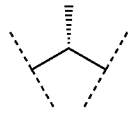 | 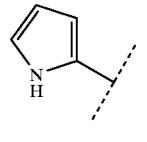 ; |
| 2004 | 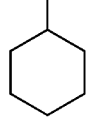 | 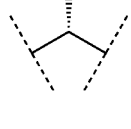 | 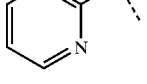 ; |
| 2005 | 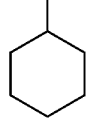 | 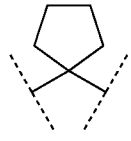 | 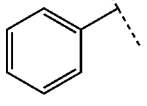 ; |
| 2006 | 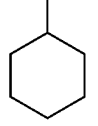 | 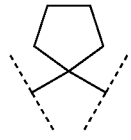 | 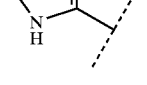 ; |
| 2007 | 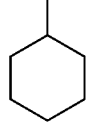 | 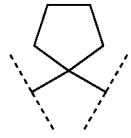 | 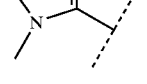 ; |
| 2008 | 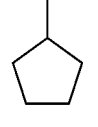 | 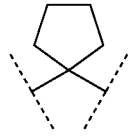 | 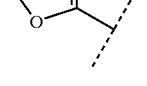 ; |
| 2009 | 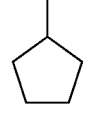 | 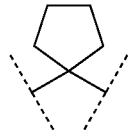 |  ; |

-continued
| Cmpd. # | R¹ | R² | R³ R⁴ |
|---|---|---|---|
| 2010 | 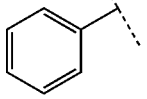 | 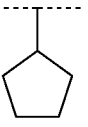 | 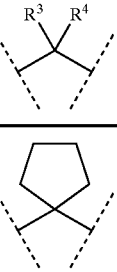 ; |
| 2011 | 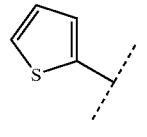 |  | 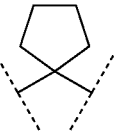 ; |
| 2012 | 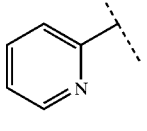 | 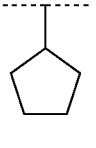 | 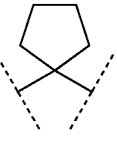 ; |
| 2013 | 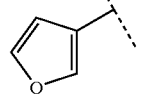 |  |  ; |
| 2014 | 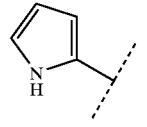 | 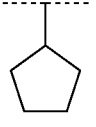 | 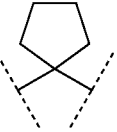 ; |
| 2015 | 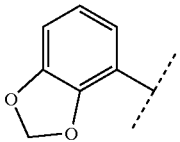 | 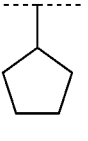 | 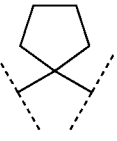 ; |
| 2016 | 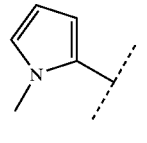 | 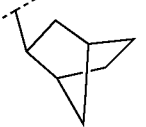<br>Racemic mixture | 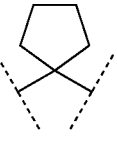 ; |
| 2017 | 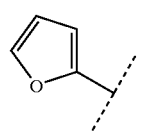 | 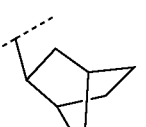<br>Racemic mixture | 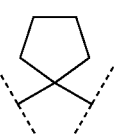 ; |
| 2018 | 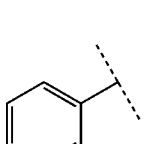 | 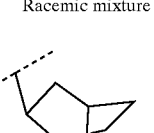<br>Racemic mixture | 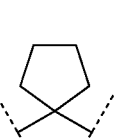 ; |

-continued

| Cmpd. # | R¹ | R² | R³ R⁴ (gem-disubstituent) |
|---|---|---|---|
| 2019 | 2-thienyl-CH< | norbornyl (Racemic mixture) | cyclopentyl (spiro) ; |
| 2020 | 2-pyridyl-CH< | norbornyl (Racemic mixture) | cyclopentyl (spiro) ; |
| 2021 | 3-furyl-CH< | norbornyl (Racemic mixture) | cyclopentyl (spiro) ; |
| 2022 | 2-pyrrolyl(NH)-CH< | norbornyl (Racemic mixture) | cyclopentyl (spiro) ; |
| 2023 | benzo[1,3]dioxol-4-yl-CH< | norbornyl (Racemic mixture) | cyclopentyl (spiro) ; |
| 2024 | 1-methyl-2-pyrrolyl-CH< | cyclobutyl | cyclopentyl (spiro) ; |
| 2025 | 2-furyl-CH< | cyclobutyl | cyclopentyl (spiro) ; |
| 2026 | phenyl-CH< | cyclobutyl | cyclopentyl (spiro) ; |

-continued
| Cmpd. # | R¹ | R² | 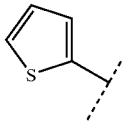 |
|---|---|---|---|
| 2027 | 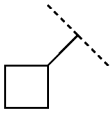 | 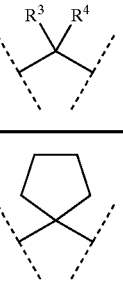 | 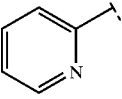 ; |
| 2028 | 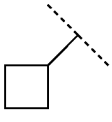 | 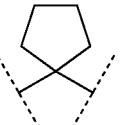 | 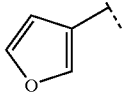 ; |
| 2029 | 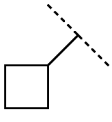 | 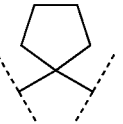 | 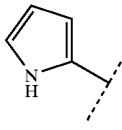 ; |
| 2030 | 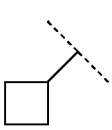 | 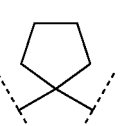 | 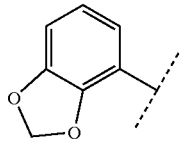 ; |
| 2031 | 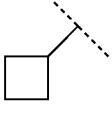 | 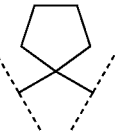 | 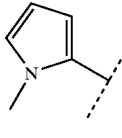 ; |
| 2032 | 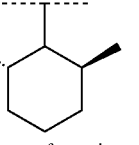 | 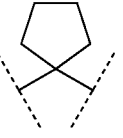<br>Mixture of enantiomers/diastereoisomers | 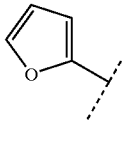 ; |
| 2033 | 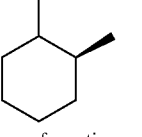 | 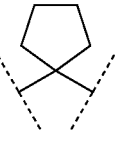<br>Mixture of enantiomers/diastereoisomers | 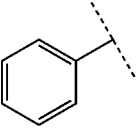 ; |
| 2034 | 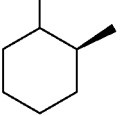 | 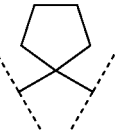<br>Mixture of enantiomers/diastereoisomers | 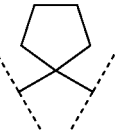 ; |

-continued
| Cmpd. # | R¹ | R² | $\begin{array}{cc}R^3 & R^4\end{array}$ |
|---|---|---|---|
| 2035 | 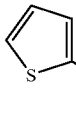 | 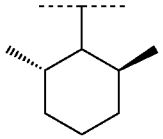<br>Mixture of enantiomers/<br>diastereoisomers | 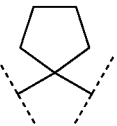 ; |
| 2036 |  | 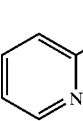<br>Mixture of enantiomers/<br>diastereoisomers | 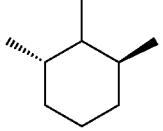 ; |
| 2037 | 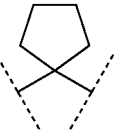 | <br>Mixture of enantiomers/<br>diastereoisomers | 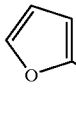 ; |
| 2038 | 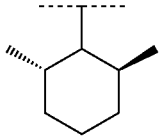 | 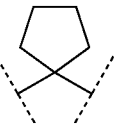<br>Mixture of enantiomers/<br>diastereoisomers |  ; |
| 2039 | 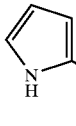 | 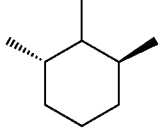<br>Mixture of enantiomers/<br>diastereoisomers | 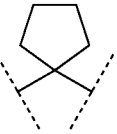 ; |
| 2040 |  | 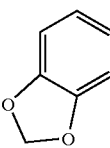<br>Racemic mixture | 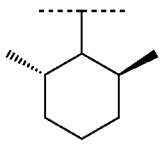 ; |
| 2041 | 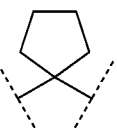 | <br>Racemic mixture | 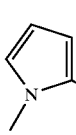 ; |

-continued

| Cmpd. # | R¹ | R² | R³ R⁴ |
|---|---|---|---|
| 2042 | phenyl | cyclohexyl (Racemic mixture) | cyclopentyl ; |
| 2043 | 2-thienyl | cyclohexyl (Racemic mixture) | cyclopentyl ; |
| 2044 | 2-pyridyl | cyclohexyl (Racemic mixture) | cyclopentyl ; |
| 2045 | 3-furyl | cyclohexyl (Racemic mixture) | cyclopentyl ; |
| 2046 | 2-pyrrolyl | cyclohexyl (Racemic mixture) | cyclopentyl ; |
| 2047 | benzo[1,3]dioxol-4-yl | cyclohexyl (Racemic mixture) | cyclopentyl ; |

-continued
| Cmpd. # | R¹ | R² | 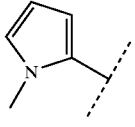 |
|---|---|---|---|
| 2048 | 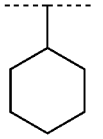 | 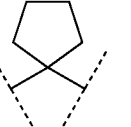 | 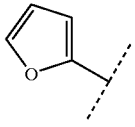 ; |
| 2049 | 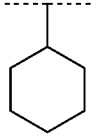 | 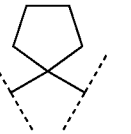 | 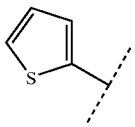 ; |
| 2050 | 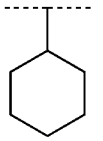 | 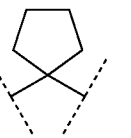 | 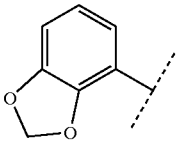 ; |
| 2051 | 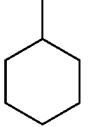 | 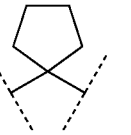 | 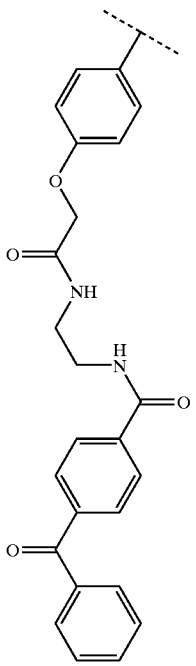 ; |
| 2052 | 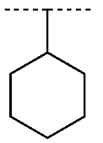 | 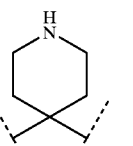 | ; and |

-continued

| Cmpd. # | R¹ | R² | R³ R⁴ |
|---|---|---|---|
| 2053 | 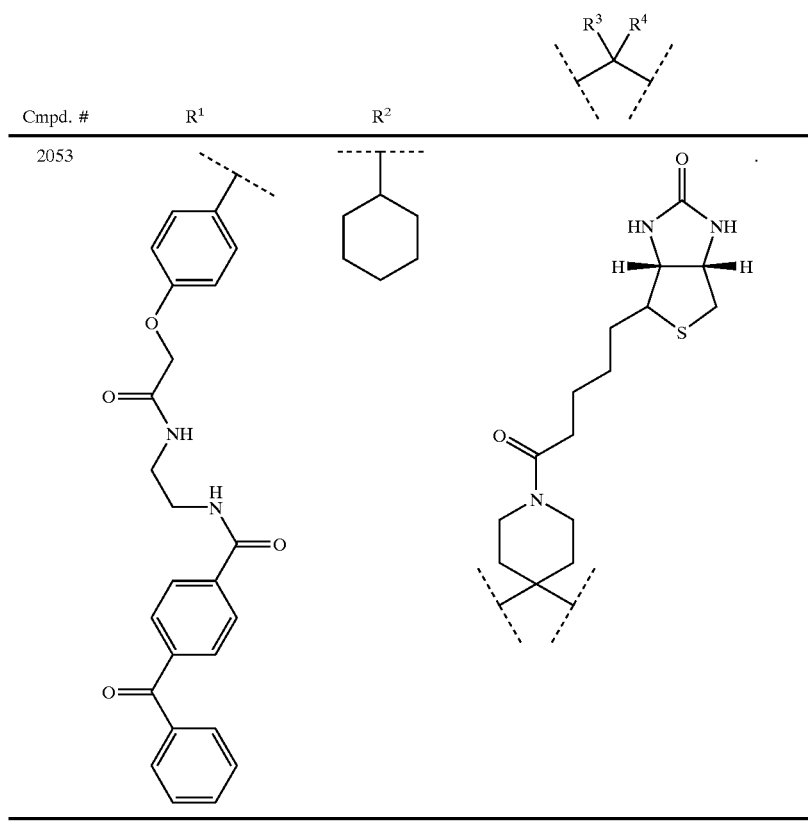 | | |

47. A compound to according to claim 1 having the following formula:

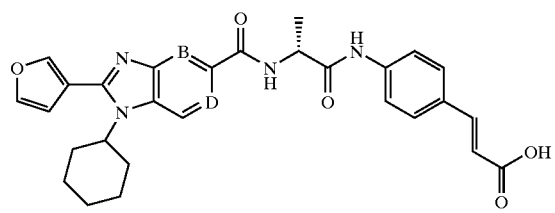

wherein B and D are defined below:

| Compound entry # | B | D |
|---|---|---|
| 3002 | CH | CMe; and |
| 3003 | CMe | CH. |

48. A pharmaceutical composition for the treatment of HCV infection, comprising an effective amount of a compound of formula I according to claim 1, or a pharmaceutically acceptable salt thereof, and a pharmaceutically acceptable carrier.

49. A composition according to claim 48, further comprising an immunomodulatory agent.

50. A composition according to claim 49, wherein said immunomodulatory agents is selected from: α-, β-, δ-γ-, and ω-interferon.

51. A composition according to claim 48, further comprising another antiviral agent.

52. A composition according to claim 51, wherein said antiviral agent is selected from: ribavirin and amantadine.

53. A composition according to claim 48, further comprising another inhibitor of HCV polymerase.

54. A composition according to claim 48, further comprising an inhibitor of HCV selected from: HCV helicase, HCV protease, HCV metalloprotease or HCV IRES.

55. A compound of the formula I, according to claim 1, or a pharmaceutically acceptable salt thereof, as an inhibitor of HCV replication.

56. An intermediate compound of formula (i):

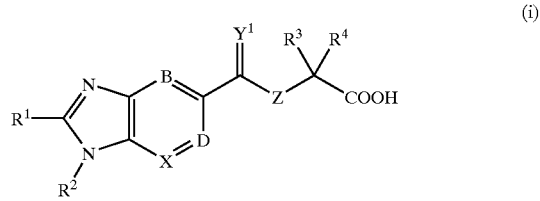

(i)

wherein $R^1$, $R^2$, $R^3$, $R^4$, B, D, X, $Y^1$, and Z are as defined in claim 1, or a derivative thereof.

57. An intermediate compound of formula I(ii):

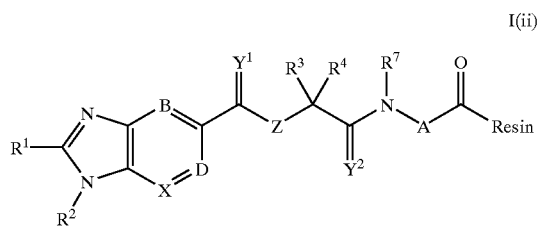

wherein $R^1$, $R^2$, $R^3$, $R^4$, $R^7$, A, B, D, X, $Y^1$, $Y^2$ and Z are as defined in claim 1, or a derivative thereof.

58. A process for producing compounds of formula I,

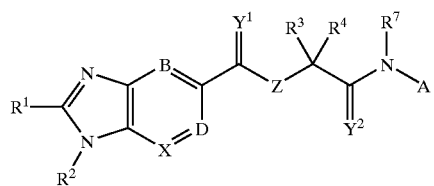

wherein $R^1$, $R^2$, $R^3$, $R^4$, $R^7$, A, B, D, X, $Y^1$, $Y^2$ and Z are as defined in claim 1, comprising:
 a) removing, in a mixture of an aqueous base or an aqueous acid in a co-solvent, the protecting group (PG) from:

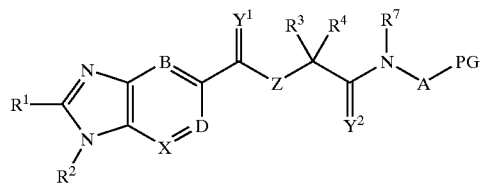

wherein $R^1$, $R^2$, $R^3$, $R^4$, $R^7$, A, B, D, X, $Y^1$, $Y^2$ and Z are as defined in claim 1, and wherein PG is a carboxylic acid protecting group, so as to produce compounds of formula I.

59. A process for producing compounds of formula I,

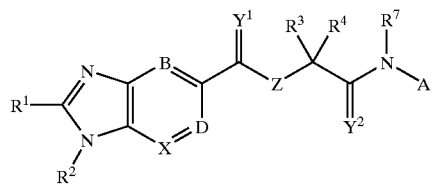

wherein $R^1$, $R^2$, $R^3$, $R^4$, $R^7$, A, B, D, X, $Y^1$, $Y^2$ and Z are as defined in claim 1, comprising:

a) cleaving, under acidic conditions, intermediate compound I (ii)

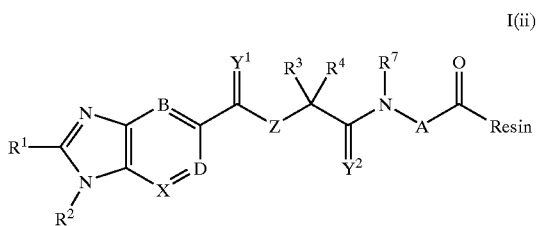

so as to produce compounds of formula I, where $R^1$, $R^2$, $R^3$, $R^4$, $R^7$, A, B, D, X, $Y^1$ and $Y^2$ are as defined in claim 1.

60. A process for producing compounds of formula I,

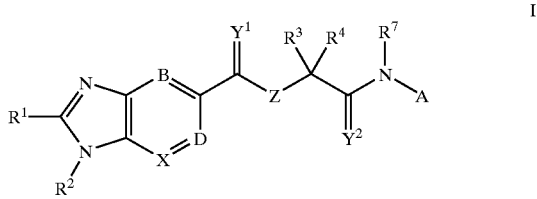

wherein $R^1$, $R^2$, $R^3$, $R^4$, $R^7$, A, B, D, X, and Z are as defined in claim 1, comprising:
 i) coupling intermediate compound of formula (i):

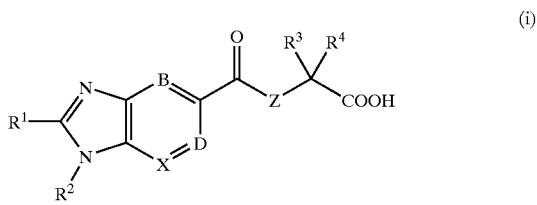

wherein $R^1$, $R^2$, $R^3$, $R^4$, B, D, X, and Z are as defined in claim 1, or a derivative thereof, with $HN(R^7)$—A wherein $R^7$ and A are as defined in claim 1, to produce a compound of formula I.

61. A method of treating HCV infection in a mammal, comprising administering to the mammal an effective amount of a compound of formula I, according to claim 1, or a pharmaceutically acceptable salt thereof.

62. A method of treating HCV infection in a mammal, comprising administering to the mammal an effective amount of a compound of formula I, according to claim 1, or a pharmaceutically acceptable salt thereof, in combination with another anti-HCV agent.

* * * * *

SEQUENCE LISTING

<160> NUMBER OF SEQ ID NOS: 4

<210> SEQ ID NO 1
<211> LENGTH: 621
<212> TYPE: PRT
<213> ORGANISM: HCV NS5B

<400> SEQUENCE: 1

```
Met Ser Tyr Tyr His His His His His His Asp Tyr Asp Ile Pro Thr
 1               5                  10                  15

Thr Glu Asn Leu Tyr Phe Gln Gly Ala Met Asp Pro Glu Phe Ser Met
            20                  25                  30

Ser Tyr Thr Trp Thr Gly Ala Leu Ile Thr Pro Cys Ala Ala Glu Glu
        35                  40                  45

Ser Gln Leu Pro Ile Asn Ala Leu Ser Asn Ser Leu Val Arg His Arg
    50                  55                  60

Asn Met Val Tyr Ser Thr Thr Ser Arg Ser Ala Ala Leu Arg Gln Lys
65                  70                  75                  80

Lys Val Thr Phe Asp Arg Leu Gln Val Leu Asp His Tyr Arg Asp
                85                  90                  95

Val Leu Lys Glu Met Lys Ala Lys Ala Ser Thr Val Lys Ala Lys Leu
            100                 105                 110

Leu Ser Val Glu Glu Ala Cys Lys Leu Thr Pro Pro His Ser Ala Lys
        115                 120                 125

Ser Lys Phe Gly Tyr Gly Ala Lys Asp Val Arg Asn Leu Ser Ser Lys
    130                 135                 140

Ala Val Asp His Ile Arg Ser Val Trp Lys Asp Leu Leu Glu Asp Thr
145                 150                 155                 160

Glu Thr Pro Ile Asp Thr Thr Ile Met Ala Lys Asn Glu Val Phe Cys
                165                 170                 175

Val Gln Pro Glu Lys Gly Gly Arg Lys Pro Ala Arg Leu Ile Val Phe
            180                 185                 190

Pro Asp Leu Gly Val Arg Val Cys Glu Lys Met Ala Leu Tyr Asp Val
        195                 200                 205

Val Ser Thr Leu Pro Gln Ala Val Met Gly Ser Ser Tyr Gly Phe Gln
    210                 215                 220

Tyr Ser Pro Lys Gln Arg Val Glu Phe Leu Val Asn Ala Trp Lys Ser
225                 230                 235                 240

Lys Lys Cys Pro Met Gly Phe Ser Tyr Asp Thr Arg Cys Phe Asp Ser
                245                 250                 255

Thr Val Thr Glu Ser Asp Ile Arg Val Glu Glu Ser Ile Tyr Gln Cys
            260                 265                 270

Cys Asp Leu Ala Pro Glu Ala Arg Gln Ala Ile Lys Ser Leu Thr Glu
        275                 280                 285

Arg Leu Tyr Ile Gly Gly Pro Leu Thr Asn Ser Lys Gly Gln Asn Cys
    290                 295                 300

Gly Tyr Arg Arg Cys Arg Ala Ser Gly Val Leu Thr Thr Ser Cys Gly
305                 310                 315                 320

Asn Thr Leu Thr Cys Tyr Leu Lys Ala Ser Ala Ala Cys Arg Ala Ala
                325                 330                 335

Lys Leu Gln Asp Cys Thr Met Leu Val Asn Gly Asp Asp Leu Val Val
            340                 345                 350

Ile Cys Glu Ser Ala Gly Thr Gln Glu Asp Ala Ala Asn Leu Arg Val
```

```
                 355                 360                 365
        Phe Thr Glu Ala Met Thr Arg Tyr Ser Ala Pro Pro Gly Asp Leu Pro
            370                 375                 380

Gln Pro Glu Tyr Asp Leu Glu Leu Ile Thr Ser Cys Ser Ser Asn Val
        385                 390                 395                 400

Ser Val Ala His Asp Ala Ser Gly Lys Arg Val Tyr Leu Thr Arg
                        405                 410                 415

Asp Pro Thr Thr Pro Leu Ala Arg Ala Ala Trp Glu Thr Ala Arg His
                        420                 425                 430

Thr Pro Ile Asn Ser Trp Leu Gly Asn Ile Ile Met Tyr Ala Pro Thr
                        435                 440                 445

Leu Trp Ala Arg Met Val Leu Met Thr His Phe Phe Ser Ile Leu Leu
            450                 455                 460

Ala Gln Glu Gln Leu Glu Lys Ala Leu Asp Cys Gln Ile Tyr Gly Ala
        465                 470                 475                 480

Cys Tyr Ser Ile Glu Pro Leu Asp Leu Pro Gln Ile Ile Glu Arg Leu
                        485                 490                 495

His Gly Leu Ser Ala Phe Ser Leu His Ser Tyr Ser Pro Gly Glu Ile
                        500                 505                 510

Asn Arg Val Ala Ser Cys Leu Arg Lys Leu Gly Val Pro Pro Leu Arg
                        515                 520                 525

Val Trp Arg His Arg Ala Arg Ser Val Arg Ala Lys Leu Leu Ser Gln
            530                 535                 540

Gly Gly Arg Ala Ala Thr Cys Gly Lys Tyr Leu Phe Asn Trp Ala Val
        545                 550                 555                 560

Arg Thr Lys Leu Lys Leu Thr Pro Ile Pro Ala Ala Ser Arg Leu Asp
                        565                 570                 575

Leu Ser Gly Trp Phe Val Ala Gly Tyr Asn Gly Gly Asp Ile Tyr His
                        580                 585                 590

Ser Leu Ser Arg Ala Arg Pro Arg Trp Phe Met Leu Cys Leu Leu Leu
                        595                 600                 605

Leu Ser Val Gly Val Gly Ile Tyr Leu Leu Pro Asn Arg
            610                 615                 620

<210> SEQ ID NO 2
<211> LENGTH: 30
<212> TYPE: DNA
<213> ORGANISM: Artificial Sequence
<220> FEATURE:
<223> OTHER INFORMATION: Forward Primer

<400> SEQUENCE: 2
acgcagaaag cgtctagcca tggcgttagt                                         30

<210> SEQ ID NO 3
<211> LENGTH: 30
<212> TYPE: DNA
<213> ORGANISM: Artificial Sequence
<220> FEATURE:
<223> OTHER INFORMATION: Reverse Primer

<400> SEQUENCE: 3
tcccggggca ctcgcaagca ccctatcagg                                         30

<210> SEQ ID NO 4
<211> LENGTH: 26
<212> TYPE: DNA
<213> ORGANISM: Artificial Sequence
```

```
-continued

<220> FEATURE:
<223> OTHER INFORMATION: PUTR probe

<400> SEQUENCE: 4
tggtctgcgg aaccggtgag tacacc                                          26
1
3
```